United States Patent
Sørensen et al.

(10) Patent No.: US 11,168,074 B2
(45) Date of Patent: Nov. 9, 2021

(54) POTASSIUM CHANNEL INHIBITORS

(71) Applicant: ACESION PHARMA ApS, Copenhagen (DK)

(72) Inventors: Ulrik Svane Sørensen, Copenhagen (DK); Antonio Mete, Leicestershire (GB)

(73) Assignee: ACESION PHARMA ApS, Copenhagen (DK)

( * ) Notice: Subject to any disclaimer, the term of this patent is extended or adjusted under 35 U.S.C. 154(b) by 38 days.

(21) Appl. No.: 16/639,214

(22) PCT Filed: Aug. 22, 2018

(86) PCT No.: PCT/EP2018/072621
§ 371 (c)(1),
(2) Date: Feb. 14, 2020

(87) PCT Pub. No.: WO2019/038315
PCT Pub. Date: Feb. 28, 2019

(65) Prior Publication Data
US 2020/0255409 A1    Aug. 13, 2020

(30) Foreign Application Priority Data

Aug. 23, 2017 (EP) .................................. 17020378

(51) Int. Cl.
| C07D 403/12 | (2006.01) |
| C07D 235/30 | (2006.01) |
| C07D 401/12 | (2006.01) |
| C07D 405/12 | (2006.01) |
| C07D 413/12 | (2006.01) |

(52) U.S. Cl.
CPC ......... *C07D 403/12* (2013.01); *C07D 235/30* (2013.01); *C07D 401/12* (2013.01); *C07D 405/12* (2013.01); *C07D 413/12* (2013.01)

(58) Field of Classification Search
CPC .. C07D 403/12; C07D 235/30; C07D 401/12; C07D 405/12; C07D 413/12
See application file for complete search history.

(56) References Cited

U.S. PATENT DOCUMENTS

| 6,569,880 | B2 * | 5/2003 | Jensen | C07C 279/18 514/388 |
| 7,737,167 | B2 * | 6/2010 | Sorensen | A61P 11/00 514/395 |
| 7,842,817 | B2 * | 11/2010 | Sorensen | A61P 1/00 548/307.4 |
| 7,960,561 | B2 * | 6/2011 | Sorensen | A61P 1/10 548/307.4 |
| 2020/0216398 | A1 * | 7/2020 | Sorensen | A61P 9/00 |

FOREIGN PATENT DOCUMENTS

| WO | 2013/104577 A1 | 7/2013 |
| WO | 2006/074991 A1 | 7/2016 |
| WO | 2017/144183 A1 | 8/2017 |

OTHER PUBLICATIONS

Diness; Journal of Cardiovascular Pharmacology 2015, 66, 441-448. doi: 10.1097/FJC.0000000000000249 (Year: 2015).*
Skibsbye; Cardiovascular Research (2014) 103, 156-167. doi:10.1093/cvr/cvu121 (Year: 2014).*
Zhu; British Journal of Pharmacology, 2015, 172, 3495-3509. DOI:10.1111/bph.13140 (Year: 2015).*
International Search Report dated Oct. 18, 2018, in corresponding International application No. PCT/EP2018/072621; 5 pages.
Sørensen et al., "Synthesis and Structure-Activity Relationship Studies of 2-(N-Substituted)-aminobenzimidazoles as Potent Negative Gating Modulators of Small Conductance Ca21-Activated Kr Channels", J. Med. Chem., 2008, vol. 51, pp. 7625-7634, 10 pages.

* cited by examiner

*Primary Examiner* — Daniel R Carcanague
(74) *Attorney, Agent, or Firm* — Maier & Maier, PLLC

(57) ABSTRACT

A compound of the general formula (I). The compounds of formula I are useful for treatment of a cardiac disease, disorder or condition in a mammal.

32 Claims, No Drawings

POTASSIUM CHANNEL INHIBITORS

FIELD

The present invention relates to novel compounds, the use of said compounds as medicament and for the manufacture of a medicament for the treatment of a cardiac disease, disorder or condition in mammals. The invention also relates to pharmaceutical compositions comprising said novel compounds.

BACKGROUND

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment, or electrolyte imbalances. Such disturbances in the impulse are called arrhythmia or dysrythmia and they may lead to unease, emboli, syncope or sudden death. In its simplest form, an arrhythmia covers everything different from a normal cardiac sinus rhythm. Disturbances can cover anything from simple palpitations to devastating ventricular fibrillation including bradycardia and tachycardia.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore evident targets for anti-arrhythmic cardiac drugs, and many anti-arrhythmic drugs on the market do exert their effect by interacting with ion channels.

Anti-arrhythmic drugs are usually divided into four main classes according to the so-called Singh Vaughan Williams classification: Class I compounds all inhibit the cardiac voltage-dependent sodium channel. Some Class I compounds do have additional effects influencing the cardiac action potential being the basis for a further subdivision into three subclasses:

Class IA compounds are sodium channel inhibitors such as Quinidine, Procainamide or Disopyramid, which prolong the action potential;

Class IB compounds are sodium channel inhibitors such as Lidocaine, Mexiletine, Tocainide or Phenytoine, which shorten the action potential; and Class IC compounds are sodium channel inhibitors such as Flecainide, Moricizine or Propafenone, which do not change the action potential duration.

Class I compounds interact with the sodium channel during its open or inactivated state and are dissociated from the channels during its closed state (during diastole). The rate of dissociation determines whether they show a frequency-dependent channel inhibition. Some of the class I compounds also inhibit subtypes of potassium or calcium permeable channels in addition to their sodium channel inhibiting effect.

Class II compounds are β-adrenoceptor inhibitors and include drugs like Atenolol, Metoprolol, Timolol or Propranolol. β-adrenoceptor inhibitors can be selective for cardiac β1-receptors or have affinity for β1- as well as β2-receptors. Some of the compounds also have an intrinsic β-stimulating effect.

Class III compounds are potassium channel inhibitors such as Amiodarone, Dronedarone, Sotalol, Ibutilide and Dofetilide, which prolong the action potential.

Class IV compounds are inhibitors of L-type calcium channels such as Verapamil.

Small-conductance calcium-activated potassium (SK) channels belongs to the family of $Ca^{2+}$-activated $K^+$ channels. Three SK channel subtypes have been cloned: SK1, SK2 and SK3 (corresponding to KCNN1-3 using the genomic nomenclature). The activity of these channels is determined by the concentration of free intracellular calcium ($[Ca^{2+}]i$) via calmodulin that is constitutively bound to the channels. SK channels are tightly regulated by $[Ca^{2+}]i$ in the physiological range being closed at $[Ca^{2+}]i$ up to around 0.1 μM but fully activated at a $[Ca^{2+}]i$ of 1 μM. Being selective for potassium, open or active SK channels have a hyperpolarizing influence on the membrane potential of the cell. SK channels are widely expressed in the central nervous system (CNS) and in peripheral tissue, including the heart.

The hyperpolarizing action of active SK channels plays an important role in the control of firing pattern and excitability of excitable cells. SK channel inhibitors such as apamin and N-methyl bicuculline, have been demonstrated to increase excitability, whereas the SK channel opener 1-EBIO is able to reduce electrical activity. In non-excitable cells, where the amount of $Ca^{2+}$ influx via voltage-independent pathways is highly sensitive to the membrane potential, an activation of SK channels will increase the driving force, whereas an inhibitor of SK channels will have a depolarizing effect, and thus diminish the driving force for calcium.

An SK channel inhibitor is a pharmaceutical agent that impairs the conduction of potassium ions ($K^+$) through $Ca^{2+}$-activated small conductance $K^+$ channels. The impairment can be obtained by any reduction in current resulting from e.g. a direct inhibition of ion conduction to a prevention of $Ca^{2+}$ binding, that is an obligate request for channel activation, or a reduction in calcium sensitivity.

A review of SK channels and SK channel modulators may be found in Wulff H et al.: "Modulators of Small- and Intermediate-Conductance Calcium-Activated Potassium Channels and their Therapeutic Indications", Current Medicinal Chemistry 2007 14 1437-1457; and in Liegeois J-F et al.: "Modulation of small conductance calcium-activated potassium (SK) channels: a new challenge in medicinal chemistry", Current Medicinal Chemistry 2003 10 625-647.

Based on the important role of SK channels in linking $[Ca^{2+}]i$ and membrane potential, SK channels are interesting targets for developing novel therapeutic agents, and the potential of inhibitors of SK channels for use in anti-arrhythmic treatment has recently been established, see e.g. Nattel S; J. Physiol. 2009 587 1385-1386; Diness J G, Sprønsen U S, Nissen J D, Al-Shahib B, Jespersen T, Grunnet M, Hansen R S; Circ. Arrhythm. Electrophysiol. 2010 3 380-90; and Diness et al; Hypertension 2011 57 1129-1135.

WO 2006/013210 describes certain 2-amino benzimidazole derivatives and their use as modulators of small-conductance calcium-activated potassium channels.

SUMMARY

The compounds of the present invention are inhibitors or negative modulators of the small-conductance calcium activated potassium (SK) channel and have an IC50 value of below 100 µM as demonstrated in the Automated patch clamping system described herein, and are considered potent drug candidates. A certain selection of these compounds have a strongly improved IC50 value of below 10 µM. Some of these compounds also have physicochemical properties suitable for a drug substance and important for making pharmaceutical formulations. Further, some of these compounds have pharmacokinetic properties making them suitable for using as pharmaceutical drugs.

In a broad aspect the present invention relates to a compound of formula (I)

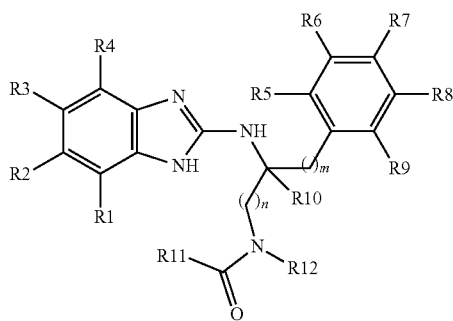

wherein n is an integer selected from 1, 2, 3, and 4;

when n is 1, 2, 3 or 4, the methylene, ethylene, propylene or butylene chain is optionally substituted with a group selected from $C_{1-6}$ alkyl optionally substituted with a halogen, such as F; and halogen;

m is an integer selected from 0 and 1;

R1-R4 are independently a group selected from H, halogen, CN, $C_{1-6}$ alkyl, $C_{1-6}$alkylene-OH, $C_{1-6}$alkoxy, $OCF_3$, $C_{1-6}$alkylene-O—$C_{1-6}$alkyl, $C_{1-6}$alkylene-S—$C_{1-6}$ alkyl, $C_{3-7}$cycloalkyl, $NR^cC(=O)$—$C_{1-6}$alkyl wherein $R^c$ is selected from H and $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$ alkylene-O—$C_{1-6}$ alkyl, C(=O)—$C_{1-6}$alkyl, C(=O)—$C_{1-6}$alkoxy, C(=O)—$C_{1-6}$alkyl-CN, C(=O)—$C_{1-6}$alkyl-OH, C(=O)—$C_{1-6}$alkylene-S—$C_{1-6}$ alkyl, C(=O)—O—$C_{1-6}$alkylene-O—$C_{1-6}$ alkyl, C(=O)—O—$C_{1-6}$alkyl-CN, C(=O)—O—$C_{1-6}$alkyl-OH, C(=O)—O—$C_{1-6}$alkylene-S—$C_{1-6}$ alkyl, C(=O)—$NHC_{1-6}$alkyl, C(=O)—$NHC_{1-6}$ alkylene-O—$C_{1-6}$ alkyl, C(=O)—$NHC_{1-6}$ alkylene-S—$C_{1-6}$ alkyl, C(=O)—$NHC_{1-6}$ alkyl-CN, C(=O)—$NHC_{1-6}$alkyl-OH, C(=O)—N($C_{1-6}$alkyl)$_2$, $SO_2$—$C_{1-6}$alkyl, $SO_2$—$C_{1-6}$ alkylene-O—$C_{1-6}$ alkyl, $SO_2$—$C_{1-6}$alkylene-S—$C_{1-6}$alkyl, $SO_2$—$C_{1-6}$alkyl-CN, $SO_2$—$C_{1-6}$alkyl-OH, and $SO_2$—$C_{1-6}$alkyl-N($C_{1-6}$ alkyl)$_2$;

R5-R9 are independently a group selected from H, halogen, $CH_2F$, $CHF_2$, $CF_3$, CN, $C_{1-6}$alkyl, $C_{1-6}$alkylene-OH, OH, $C_{1-6}$alkoxy, $C_{1-6}$alkylene-O—$C_{1-6}$alkyl, $C_{1-6}$ alkylene-S—$C_{1-6}$alkyl, $C_{3-7}$cycloalkyl, C(=O)—O—$C_{1-6}$alkyl, S—$C_{1-6}$alkyl, $SCF_3$, $OCF_3$, $OCF_2H$, $OCFH_2$, $OC_{3-7}$cycloalkyl, $SC_{3-7}$cycloalkyl;

R10 is a group selected from H, $C_{1-6}$alkyl, $C_{1-6}$alkyl substituted with 1 to 3 Fluorine atoms, and $C_{3-4}$cycloalkyl;

R11 is a group selected from $C_{1-6}$alkyl, $C_{1-6}$alkylene-OH; $C_{1-6}$alkylene-O—$C_{1-6}$ alkyl, wherein $C_{1-6}$ alkylene is optionally substituted with a phenyl, and wherein $C_{1-6}$ alkyl is optionally substituted with a halogen, such as F; $C_{1-6}$ alkylene-S—$C_{1-6}$ alkyl; $C_{1-6}$ alkylene-CN; $C_{1-6}$ alkylene-C(=O)—O—$C_{1-6}$ alkyl; $C_{1-6}$ alkylene-O—C(=O)—NH—$C_{1-6}$ alkyl; $C_{3-7}$cycloalkyl; an aryl optionally substituted with a group selected from $C_{1-6}$ alkyl, halogen, CN, OH, and $C_{1-6}$alkylene-OH; an aliphatic heterocycle optionally substituted with a group selected from $C_{1-6}$ alkyl, OH, and $C_{1-6}$ alkylene-OH; and a heteroaryl optionally substituted with a group selected from $C_{1-6}$ alkyl, halogen, CN, OH, and $C_{1-6}$ alkylene-OH;

R12 is a group selected from H, and $C_{1-6}$ alkyl; or

R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, wherein the monocyclic aliphatic heterocycle is optionally substituted at the two to six further carbon atoms with a group selected from $C_{1-6}$ alkyl; oxo; OH; $C_{1-6}$ alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR^mR^n$, wherein $R^m$ and $R^n$ are independently a group selected from H and $C_{1-6}$ alkyl; or a pharmaceutically acceptable salt thereof.

In an embodiment m is 0.

In a further embodiment n is selected from 1, 2 and 3. In a particular embodiment n is selected from 2 and a $C_{1-6}$ alkyl is attached to the ethylene chain.

In a still further embodiment R1 is selected from H and $C_{1-6}$ alkylene-OH. Typically, R1 is selected from H and $CH_2OH$.

In a further embodiment R2 is selected from H and halogen. Typically, R2 is selected from H and F.

In a still further embodiment R3 is selected from H and halogen. Typically, R3 is selected from H.

In a further embodiment R4 is selected from H and $C_{1-6}$ alkylene-OH. Typically, R4 is selected from H.

In a still further embodiment R5 is selected from H.

In a further embodiment R6 is selected from $CH_2F$, $CHF_2$, $CF_3$, and $OCF_3$. Typically, R6 is selected from $CF_3$ and $OCF_3$.

In a still further embodiment R7 is selected from H.

In a further embodiment R8 is selected from H, $CH_2F$, $CHF_2$, $CF_3$, and $OCF_3$. Typically, R8 is selected from H.

In a still further embodiment R9 is selected from H.

In a further embodiment R10 is a group selected from H and $C_{1-6}$ alkyl. Typically, R10 is selected from H and $CH_3$.

In a still further embodiment R11 is selected from $C_{1-6}$alkyl; $C_{1-6}$alkylene-OH; $C_{1-6}$alkylene-O—$C_{1-6}$alkyl; $C_{3-7}$cycloalkyl; an aryl optionally substituted with a group selected from halogen and CN; an aliphatic heterocycle; and a heteroaryl. Typically, R11 is selected from $CH_3$, $CH_2CH_3$, $CH_2$—OH; $CH_2$—O—$CH_3$; $C_{3-4}$cycloalkyl; a phenyl substituted with a group selected from flour and CN; a tetrahydropyranyl; an oxazolyl; an oxadiazolyl; a pyrimidyl; and a pyridyl.

In a further embodiment R12 is selected from H and $CH_3$.

In a still further embodiment R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, selected from a pyrrolidinyl-2-on.

In a further embodiment the compound of formula (I) is selected from:

N-{2-[(1H-1,3-benzodiazol-2-yl)amino]-2-[3-(trifluoromethyl)phenyl]ethyl}-1,2-oxazole-3-carboxamide, N-{2-[(1H-1,3-benzodiazol-2-yl)amino]-2-[3-(trifluoromethyl)phenyl]ethyl}-cyclobutanecarboxamide,
N-{2-[(1H-1,3-benzodiazol-2-yl)amino]-2-[3-(trifluoromethyl)phenyl]ethyl}-cyclopropanecarboxamide,
N-{2-[(1H-1,3-benzodiazol-2-yl)amino]-2-[3-(trifluoromethyl)phenyl]ethyl}-1,2,4-oxadiazole-3-carboxamide,
N-{2-[(1H-1,3-benzodiazol-2-yl)amino]-2-[3-(trifluoromethyl)phenyl]ethyl}-pyrimidine-4-carboxamide,
N-{2-[(1H-1,3-benzodiazol-2-yl)amino]-2-[3-(trifluoromethyl)phenyl]ethyl}-pyridine-2-carboxamide,
N-{2-[(1H-1,3-benzodiazol-2-yl)amino]-2-[3-(trifluoromethyl)phenyl]ethyl}-3-cyanobenzamide,
N-{2-[(1H-1,3-benzodiazol-2-yl)amino]-2-[3-(trifluoromethyl)phenyl]ethyl}-oxane-4-carboxamide,
N-{2-[(1H-1,3-benzodiazol-2-yl)amino]-2-[3-(trifluoromethyl)phenyl]ethyl}-3-fluorobenzamide,
N-{2-[(1H-1,3-benzodiazol-2-yl)amino]-2-[3-(trifluoromethyl)phenyl]ethyl}-propanamide,
(−)-N-{2-[(1H-1,3-benzodiazol-2-yl)amino]-2-[3-(trifluoromethyl)phenyl]-ethyl}propanamide,
(+)-N-{2-[(1H-1,3-benzodiazol-2-yl)amino]-2-[3-(trifluoromethyl)phenyl]-ethyl}propanamide,
1-{2-[(1H-1,3-benzodiazol-2-yl)amino]-2-[3-(trifluoromethyl)phenyl]ethyl}-pyrrolidin-2-one,
N-[(2R)-2-[(1H-1,3-benzodiazol-2-yl)amino]-2-[3-(trifluoromethyl)phenyl]-ethyl]-2-methoxyacetamide,
N-[(2R)-2-[(1H-1,3-benzodiazol-2-yl)amino]-2-[3-(trifluoromethyl)phenyl]-ethyl]-2-hydroxyacetamide,
N-{3-[(1H-1,3-benzodiazol-2-yl)amino]-3-[3-(trifluoromethyl)phenyl]-propyl}acetamide,
(−)-N-{3-[(1H-1,3-benzodiazol-2-yl)amino]-3-[3-(trifluoromethyl)phenyl]-propyl}acetamide,
(+)-N-{3-[(1H-1,3-benzodiazol-2-yl)amino]-3-[3-(trifluoromethyl)phenyl]-propyl}acetamide,
N-(3-{[4-(hydroxymethyl)-1H-1,3-benzodiazol-2-yl]amino}-3-[3-(trifluoromethyl)phenyl]propyl)-1,2-oxazole-3-carboxamide,
N-{3-[(1H-1,3-benzodiazol-2-yl)amino]-3-[3-(trifluoromethyl)phenyl]-propyl}-2,2,2-trifluoroacetamide,
N-{4-[(1H-1,3-benzodiazol-2-yl)amino]-4-[3-(trifluoromethyl)phenyl]butan-2-yl}acetamide,
N-{3-[(1H-1,3-benzodiazol-2-yl)amino]-3-[3-(trifluoromethyl)phenyl]-propyl}-N-methylacetamide,
(−)-N-{3-[(1H-1,3-benzodiazol-2-yl)amino]-3-[3-(trifluoromethyl)phenyl]-propyl}-N-methylacetamide,
(+)-N-{3-[(1H-1,3-benzodiazol-2-yl)amino]-3-[3-(trifluoromethyl)phenyl]-propyl}-N-methylacetamide,
N-{4-[(1H-1,3-benzodiazol-2-yl)amino]-4-[3-(trifluoromethyl)phenyl]-butyl}acetamide,
(−)-N-{4-[(1H-1,3-benzodiazol-2-yl)amino]-4-[3-(trifluoromethyl)phenyl]-butyl}acetamide,
(+)-N-{4-[(1H-1,3-benzodiazol-2-yl)amino]-4-[3-(trifluoromethyl)phenyl]-butyl}acetamide,
N-{4-[(5-fluoro-1H-1,3-benzodiazol-2-yl)amino]-4-[3-(trifluoromethyl)-phenyl]-butyl}-acetamide,
N-{3-[(1H-1,3-benzodiazol-2-yl)amino]-3-[3-(trifluoromethyl)phenyl]-butyl}acetamide,
N-{3-[(1H-1,3-benzodiazol-2-yl)amino]-3-[3-(trifluoromethoxy)phenyl]-propyl}acetamide,
(−)-N-{3-[(1H-1,3-benzodiazol-2-yl)amino]-3-[3-(trifluoromethoxy)phenyl]-propyl}-acetamide, and
(+)-N-{3-[(1H-1,3-benzodiazol-2-yl)amino]-3-[3-(trifluoromethoxy)phenyl]-propyl}-acetamide; or
a pharmaceutically acceptable salt thereof.

In a further aspect the present invention relates to a compound of formula (I) as defined above for use as a medicine.

In a still further aspect the present invention relates to a pharmaceutical composition comprising a compound of formula (I) as defined above and optionally a pharmaceutically acceptable additive, such as carrier or excipient.

In a further aspect the present invention relates to a compound of formula (I) as defined above for use in a method for treating a cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

In a further aspect the present invention relates to a method for treatment of a cardiac disease, disorder or condition in a mammal, such as a human, wherein a therapeutically effective amount of at least one compound of formula (I) as defined above is administered to a mammal in need of said treatment. In an embodiment the cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure, In a still further aspect the present invention relates to a process of preparing a compound of formula I or a pharmaceutically acceptable salt or solvate thereof comprising the steps:

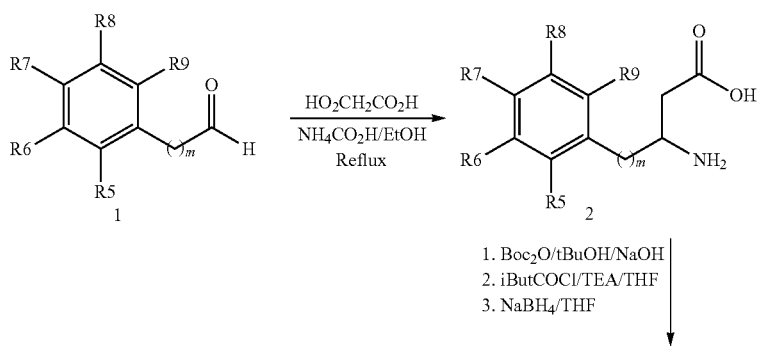

-continued
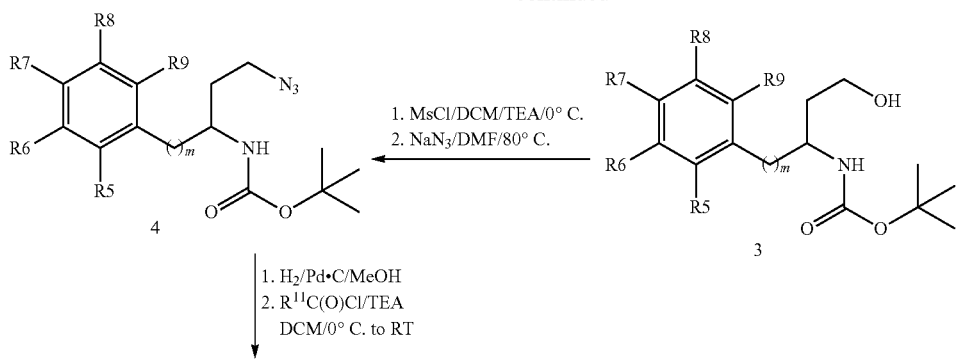
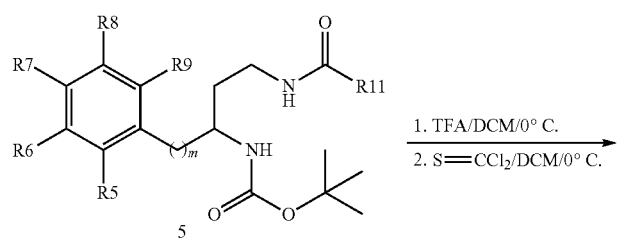
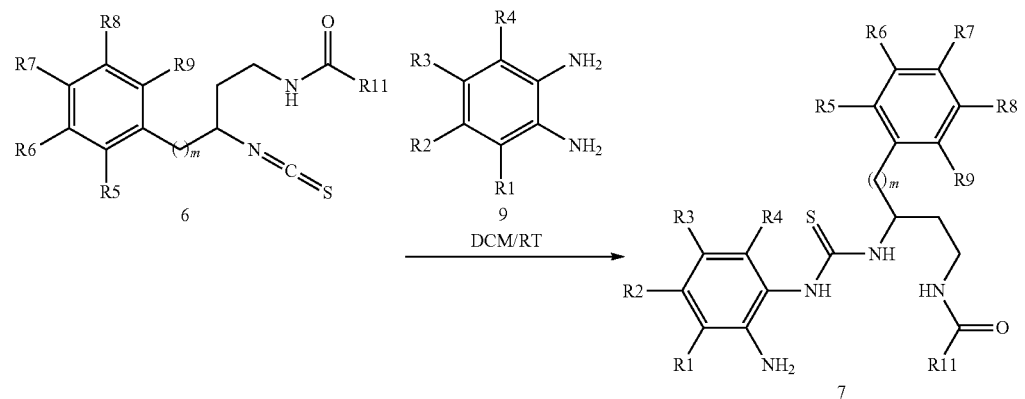
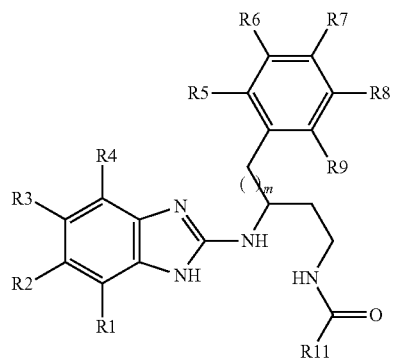

DETAILED DESCRIPTION

In a broad aspect the present invention relates to a compound of formula (I)

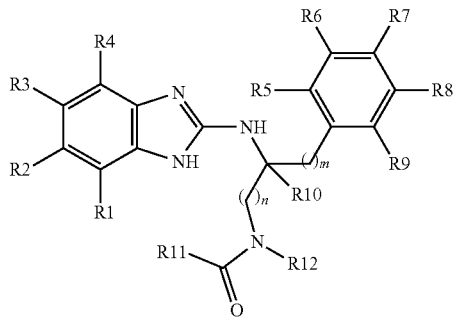

wherein n is an integer selected from 1, 2, 3, and 4;

when n is 1, 2, 3 or 4, the methylene, ethylene, propylene or butylene chain is optionally substituted with a group selected from $C_{1-6}$ alkyl optionally substituted with a halogen; and halogen;

m is an integer selected from 0 and 1;

R1-R4 are independently a group selected from H, halogen, CN, $C_{1-6}$ alkyl, $C_{1-6}$alkylene-OH, $C_{1-6}$alkoxy, $OCF_3$, $C_{1-6}$alkylene-O—$C_{1-6}$alkyl, $C_{1-6}$alkylene-S—$C_{1-6}$ alkyl, $C_{3-7}$cycloalkyl, $NR^cC(\!\!=\!\!O)$—$C_{1-6}$alkyl wherein $R^c$ is selected from H and $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$ alkylene-O—$C_{1-6}$ alkyl, $C(\!\!=\!\!O)$—$C_{1-6}$alkyl, $C(\!\!=\!\!O)$—$C_{1-6}$alkoxy, $C(\!\!=\!\!O)$—$C_{1-6}$alkyl-CN, $C(\!\!=\!\!O)$—$C_{1-6}$alkyl-OH, $C(\!\!=\!\!O)$—$C_{1-6}$alkylene-S—$C_{1-6}$alkyl, $C(\!\!=\!\!O)$—O—$C_{1-6}$alkylene-O—$C_{1-6}$ alkyl, $C(\!\!=\!\!O)$—O—$C_{1-6}$alkyl-CN, $C(\!\!=\!\!O)$—O—$C_{1-6}$alkyl-OH, $C(\!\!=\!\!O)$—O—$C_{1-6}$ alkylene-S—$C_{1-6}$ alkyl, $C(\!\!=\!\!O)$—$NHC_{1-6}$alkyl, $C(\!\!=\!\!O)$—$NHC_{1-6}$ alkylene-O—$C_{1-6}$alkyl, $C(\!\!=\!\!O)$—$NHC_{1-6}$alkylene-S—$C_{1-6}$alkyl, $C(\!\!=\!\!O)$—$NHC_{1-6}$alkyl-CN, $C(\!\!=\!\!O)$—$NHC_{1-6}$alkyl-OH, $C(\!\!=\!\!O)$—$N(C_{1-6}$alkyl$)_2$, $SO_2$—$C_{1-6}$alkyl, $SO_2$—$C_{1-6}$alkylene-O—$C_{1-6}$ alkyl, $SO_2$—$C_{1-6}$alkylene-S—$C_{1-6}$ alkyl, $SO_2$—$C_{1-6}$alkyl-CN, $SO_2$—$C_{1-6}$alkyl-OH, and $SO_2$—$C_{1-6}$ alkyl-$N(C_{1-6}$alkyl$)_2$;

R5-R9 are independently a group selected from H, halogen, $CH_2F$, $CHF_2$, $CF_3$, CN, $C_{1-6}$ alkyl, $C_{1-6}$ alkylene-OH, OH, $C_{1-6}$alkoxy, $C_{1-6}$alkylene-O—$C_{1-6}$ alkyl, $C_{1-6}$ alkylene-S—$C_{1-6}$alkyl, $C_{3-7}$cycloalkyl, $C(\!\!=\!\!O)$—O—$C_{1-6}$alkyl, S—$C_{1-6}$alkyl, $SCF_3$, $OCF_3$, $OCF_2H$, $OCFH_2$, $OC_{3-7}$cycloalkyl, $SC_{3-7}$cycloalkyl;

R10 is a group selected from H, $C_{1-6}$ alkyl, $C_{1-6}$alkyl substituted with 1 to 3 Fluorine atoms, and $C_{3-4}$cycloalkyl;

R11 is a group selected from $C_{1-6}$alkyl, $C_{1-6}$alkylene-OH; $C_{1-6}$alkylene-O—$C_{1-6}$ alkyl, wherein $C_{1-6}$alkylene is optionally substituted with a phenyl, and wherein $C_{1-6}$ alkyl is optionally substituted with a halogen, such as F; $C_{1-6}$ alkylene-S—$C_{1-6}$ alkyl; $C_{1-6}$alkylene-CN; $C_{1-6}$alkylene-C($\!\!=\!\!O$)—O—$C_{1-6}$ alkyl; $C_{1-6}$alkylene-O—C($\!\!=\!\!O$)—NH—$C_{1-6}$ alkyl; $C_{3-7}$cycloalkyl; an aryl optionally substituted with a group selected from $C_{1-6}$ alkyl, halogen, CN, OH, and $C_{1-6}$alkylene-OH; an aliphatic heterocycle optionally substituted with a group selected from $C_{1-6}$ alkyl, OH, and $C_{1-6}$alkylene-OH; and a heteroaryl optionally substituted with a group selected from $C_{1-6}$ alkyl, halogen, CN, OH, and $C_{1-6}$ alkylene-OH;

R12 is a group selected from H, and $C_{1-6}$ alkyl; or

R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, wherein the monocyclic aliphatic heterocycle is optionally substituted at the two to six further carbon atoms with a group selected from $C_{1-6}$ alkyl; oxo; OH; $C_{1-6}$ alkylene-OH; C($\!\!=\!\!O$)—$C_{1-6}$ alkyl; C($\!\!=\!\!O$)—O—$C_{1-6}$ alkyl; $SO_2$—$C_{1-6}$alkyl; $NR^kR^l$, wherein $R^k$ and $R^l$ are independently a group selected from H and $C_{1-6}$ alkyl; and $C_{1-6}$alkylene-$NR^mR^n$, wherein $R^m$ and $R^n$ are independently a group selected from H and $C_{1-6}$ alkyl; or a pharmaceutically acceptable salt thereof.

In an embodiment m is 0. In another embodiment m is 1.

In a further embodiment n is 1. In a still further embodiment n is 2. In a particular embodiment n is selected from 2 and a $C_{1-6}$ alkyl is attached to the ethylene chain, typically a methyl or ethyl, preferably methyl. In a further embodiment n is 3.

In a still further embodiment R1, R2 R3, and R4 are H.

In a further embodiment R1 is $C_{1-6}$ alkylene-OH, such as $C_{1-3}$ alkylene-OH, typically $CH_2OH$; and R2, R3, and R4 are H.

In a further embodiment R2 is selected from halogen, such as F or $C_1$, typically F; and R1, R3, and R4 are H.

In a still further embodiment R3 is selected from H and halogen. Typically, R3 is selected from H.

In a further embodiment R4 is selected from H and $C_{1-6}$ alkylene-OH. Typically, R4 is selected from H.

In a still further embodiment R5 is selected from H.

In a further embodiment R6 is selected from $CH_2F$, $CHF_2$, $CF_3$, and $OCF_3$; and R5, R7, R8 and R9 are H. Typically, R6 is selected from $CF_3$ and $OCF_3$; and R5, R7, R8 and R9 are H.

In a still further embodiment R7 is selected from H.

In a further embodiment R8 is selected from H, $CH_2F$, $CHF_2$, $CF_3$, and $OCF_3$. Typically, R8 is selected from H.

In a still further embodiment R9 is selected from H.

In a further embodiment R10 is H. In another embodiment R10 is $C_{1-6}$ alkyl, such as $CH_3$.

In a still further embodiment R11 is $C_{1-6}$ alkyl, such as $CH_3$ or $CH_2CH_3$. In another embodiment R11 is $C_{1-6}$ alkylene-OH, such as $CH_2$—OH. In a further embodiment R11 is $C_{1-6}$alkylene-O—$C_{1-6}$ alkyl, such as $CH_2$—O—$CH_3$. In a still further embodiment R11 is $C_{3-7}$cycloalkyl, such as cyclopropyl or cyclobutyl. In a further embodiment R11 is an aryl optionally substituted with a group selected from halogen and CN, such as a phenyl substituted with a group selected from halogen and CN, typically a phenyl substituted with a group selected from F and CN. In a still further embodiment R11 is an aliphatic heterocycle, such as a tetrahydropyranyl. In a further embodiment R11 is a heteroaryl, such as an oxazolyl, an oxadiazolyl, a pyrimidyl, or a pyridyl.

In a further embodiment R12 is H. In another embodiment R12 is $CH_3$.

In a still further embodiment R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, selected from a monocyclic 4-6 membered aliphatic heterocycle, such as a monocyclic 5 membered aliphatic heterocycle. Typically R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, which is pyrrolidinyl-2-on.

Cardiac Diseases

In the context of this invention a cardiac disease, disorder or condition is any cardiac disease, disorder or condition, including, but not limited to, an abnormal rhythm of the heart or variant and exercise induced angina.

In a more specific embodiment the cardiac disease, disorder or condition is any disease, disorder or condition associated with an abnormal rhythm of the heart or variant and exercise induced angina.

In a more specific embodiment the cardiac disease, disorder or condition is any disease, disorder or condition associated with an abnormal rhythm of the heart.

In a more specific embodiment the cardiac disease, disorder or condition associated with an abnormal rhythm of the heart is selected from cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In another embodiment a cardiac disease, disorder or condition of the invention is an abnormal rhythm caused by myocardial ischaemia, myocardial infarction, cardiac hypertrophy, or cardiomyopathy.

In another embodiment a cardiac disease, disorder or condition of the invention is an abnormal rhythm arising after cardiac surgery or a cardiac ablation procedure.

In a further specific embodiment, the cardiac disease, disorder or condition associated with an abnormal rhythm of the heart is a cardiac arrhythmia caused by a genetic disease.

In a still further preferred embodiment the cardiac disease, disorder or condition associated with an abnormal rhythm of the heart is cardiac arrhythmia.

In a preferred embodiment the cardiac disease, disorder or condition associated with an abnormal rhythm of the heart is atrial fibrillation.

In a particular embodiment the compound of formula (I) of the present invention is useful for treatment of atrial fibrillation by acute cardioversion to normal sinus rhythm.

In another particular embodiment the compound of formula (I) of the present invention is useful for treatment of atrial fibrillation by maintaining normal sinus rhythm and avoiding or reducing the occurrence of new episodes of atrial fibrillation.

Pharmacological Treatment of Atrial Fibrillation

In the context of this invention, and as understood by a person skilled in the art, treatment of atrial fibrillation is acute cardioversion or maintenance of sinus rhythm or both. Acute conversion is defined as application of compound that has the ability to convert atrial fibrillation to a normal cardiac sinus rhythm. Normal sinus rhythm is defined as regular stable heart beating at frequencies between 40 and 100 beats at rest in adults with normal regular p-wave on a standard 12-lead electrocardiogram. Maintenance of sinus rhythm is defined as the ability for a compound to preserve a normal stable sinus rhythm over time with no relapse to atrial fibrillation or the ability of a compound to significantly reduced the incidence of relapse from atrial fibrillation to normal sinus rhythm compared to non-treated controls.

Description of General Process

Scheme 1 summarises one of the synthetic approaches that can be used to prepare compounds of general formula (I).

Scheme 1

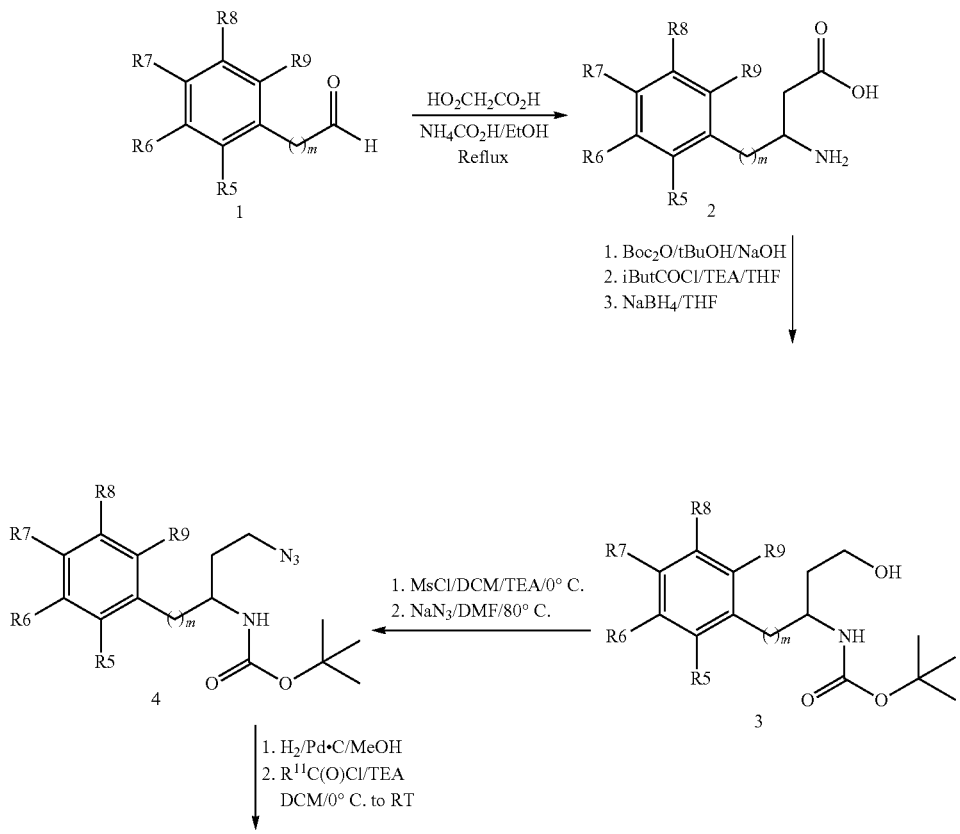

-continued

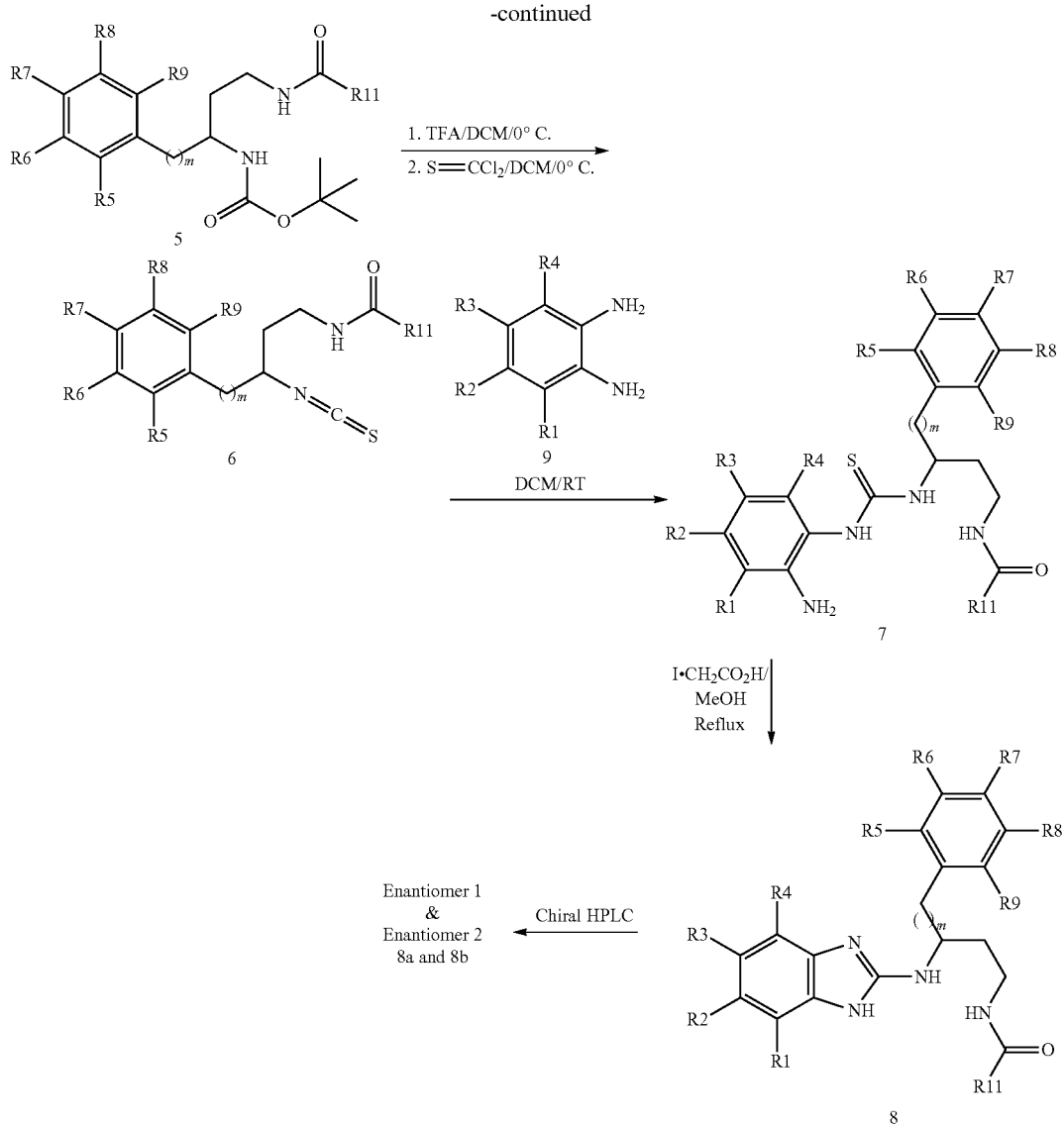

A large number of aldehydes (1) are commercially available or can be readily prepared by many routes described in the literature. The aldehydes (1) can be converted to the β-amino acids (2) by a wide range of methods, such as reaction of (1) with malonic acid derivatives under the influence of ammonium salts (e.g. ammonium formate) followed by subsequent decarboxylation upon heating. In addition, a large number of β-amino acids (2) and derivatives (such as their esters and amides) are also available from commercial sources. The β-amino acids (2) can be reduced to the alcohol derivatives (3) by converting to a mixed anhydride (e.g. with isobutylchloride) under the influence of a base (e.g. triethylamine) followed by reducing to the alcohol with hydride reducing agents (e.g. $NaBH_4$) in suitable solvents (e.g. THF). There are many other well-established methods for reducing acids to alcohols described in the literature. The alcohol derivative (3) can be converted to the azido derivatives (4) by reaction with methanesulphonyl chloride in a suitable solvent (e.g. dichloromethane) under the influence of a base (e.g. triethylamine), followed by reaction with sodium azide with heating in a suitable solvent (e.g. DMF). The azido derivative (4) can be converted to the N-acylated derivatives (5) by hydrogenation with hydrogen gas over a catalyst (e.g. Pd on carbon) in a suitable solvent (e.g. methanol), followed by reaction with an acid chloride in a suitable solvent (e.g. DCM) under the influence of a base (e.g. triethylamine) at 0° C. The N-acylated derivatives (5) can be converted to the isothiocyanate derivatives (6) by reaction with thiophosgene in a suitable solvent (e.g. dichloromethane) under the influence of a base (e.g. sodium hydrogen carbonate). The isothiocyanates (6) can react with a wide range of benzene-1,2-diamine derivatives (9) in a suitable solvent (e.g. dichloromethane) to afford the thiourea products (7). A wide range of benzene-1,2-diamine derivatives (9) are available commercially or can be readily prepared by well-established methods described in the literature (e.g. by nitration and subsequent reduction of commercial substituted benzene starting materials). The thiourea derivatives (7) can be converted to 2-aminobenzimidazole derivatives (8) by a ring forming reaction that occurs under the influence of iodoacetic acid and heating in a suitable solvent (such as methanol or acetonitrile). The cyclisation of (7) to afford (8) can also occur under the influence of mercury salts (e.g. mercuric oxide) with heating in a suitable solvent (e.g. acetonitrile). The 2-aminobenzimidazole derivatives (8) can be a racemic mixture, which can be separated into the two enantiomers (8a) and (8b) by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

The process described above is applicable to prepare compounds of general formula (1) in which m=0 or 1 by starting with the appropriate starting aldehyde (1). A large number of aldehydes (1) (m=0 or 1) are available commercially or can be readily prepared by many well-established methods described in the literature. Compounds of general formula (I) in which n=0 can also be made by the general process described above, by starting with an α-amino acid (2) (n=0). A large number of α-amino acids are available commercially or can be readily prepared by many well-established methods described in the literature.

Compounds of general formula (I) in which n=2 can also be made by the general process described above, by a chain extension reaction on the alcohol derivative (3). The alcohol derivative (3) is reacted with methanesulphonyl chloride in a suitable solvent (e.g. dichloromethane) under the influence of a base (e.g. triethylamine), followed by reaction with sodium cyanide with heating in a suitable solvent (e.g. DMF) to afford a cyano derivative. This cyano derivative can be hydrogenated to a primary amino derivative, (e.g. using Pd on carbon under acidic conditions and pressure of 355 Psi.) which on treatment with an acid chloride will afford the chain extended derivative (5).

The process is suitable for a wide range of derivatives bearing a variety of R1 to R9 groups. In some cases the R1 to R9 groups may need to carry a chemical protecting group (e.g. when R1 to R9 bear substituents such as: —OH, —NH$_2$, NHR, —SH, —CO$_2$H etc). The protecting groups can be removed by a suitable de-protection step. The skilled person will understand that it may be necessary to adjust or change the order of steps in the processes described above, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldiphenylsilyl or trimethylsilyl), AcO(acetoxy), TBS(t-butyldimethylsilyl), TMS(trimethylsilyl), PMB (p-methoxybenzyl), and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The compound of formula (I) have at least one asymmetric center, and may have further asymmetric centres and it is intended that any optical isomers (i.e. enantiomers or diastereomers), in the form of separated, pure or partially purified optical isomers and any mixtures thereof including racemic mixtures, i.e. a mixture of stereoisomeres, are included within the scope of the invention. In particular, the carbon atom of formula (I) wherein the 4 valence bonds are linked to R10, NH, (C)$_n$, and (C)$_m$ and is an asymmetric centre giving rise to two optical isomers, an R form and an S form. In one embodiment, the compounds of the present invention have the S form. In another embodiment, the compounds of the present invention have the R form. In a further embodiment, the compounds of the present invention are a racemic mixture.

In this context it is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In a still further embodiment the compound I is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "free form" as used herein means a compound of formula (I) which is a free base or free acid, as the case may be, and which is not in any salt form.

The term "$C_{1-X}$ alkyl" as used herein means an alkyl group containing 1 to x carbon atoms, e.g. $C_{1-3}$, $C_{1-4}$, $C_{1-5}$ or $C_{1-6}$, such as methyl, ethyl, propyl, butyl, pentyl or hexyl, and also includes branched $C_{3-6}$ alkyl, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl. When $C_{1-X}$ alkyl, such as $C_{1-6}$alkyl, is substituted with a group, such as halogen, such as a F, it means that such F, e.g. 3 F are attached to one carbon ($CF_3$) or two carbons ($CF_2$—CF) or even three carbons (CF—CF—CF).

The term "$C_{1-X}$ alkylene" as used herein means an alkylene group containing 1 to x carbon atoms, e.g. $C_{1-3}$, $C_{1-4}$, $C_{1-5}$ or $C_{1-6}$, such as methylene, ethylene, propylene, butylene, pentylene or hexylene, and also includes branched $C_{3-6}$ alkylene, such as isopropylene, isobutylene, tert-butylene, isopentylene, 3-methylbutylene, 2,2-dimethylpropylene, n-hexylene, 2-methylpentylene, 2,2-dimethylbutylene, 2,3-dimethylbutylene.

The term "$C_{2-6}$ alkenyl" as used herein means an alkenyl group containing 2 to 6 carbon atoms, e.g. $C_{2-3}$, $C_{2-4}$, $C_{2-5}$ or $C_{2-6}$, and a double bond, such as one double bond, such as ethenyl, propenyl, butenyl, pentenyl or hexenyl, and also includes branched $C_{3-6}$ alkenyl, such as isopropenyl, isobutenyl, tert-butenyl, isopentenyl.

The term "$C_{1-X}$ alkoxy" or "O—$C_{1-6}$alkyl" (used interchangeable) as used herein means one oxygen atom covalently linked to an alkyl group containing 1 to x carbon atoms, e.g. $C_{1-5}$ or $C_{1-6}$, such as methoxy, ethoxy, n-propoxy, iso-propoxy, n-butyloxy, n-pentyloxy, or n-hexyloxy.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "Oxo" as used herein means an oxygen atom with double bonds, also indicated as =O.

The term "CN" as used herein means a nitril (C and N linked by triple bond).

The term "C(=O)" as used herein means a carbonyl group.

When "$C_{1-6}$ alkyl" or "$C_{1-6}$alkylene" is linked to another group or atom, such as in $C_{1-6}$alkylene-OH, $C_{1-6}$alkylene-CN, $C_{1-6}$alkylene-$CF_3$, $C_{1-6}$alkylene-O—$C_{1-6}$ alkyl, $C_{1-6}$alkylene-S—$C_{1-6}$ alkyl, $C_{1-6}$alkylene-$NR^aR^b$, C(=O)—$C_{1-6}$ alkyl, C(=O)—$C_{1-6}$alkoxy, C(=O)—$C_{1-6}$alkyl-CN, C(=O)—$C_{1-6}$alkyl-OH, C(=O)—$C_{1-6}$ alkylene-S—$C_{1-6}$ alkyl, C(=O)—O—$C_{1-6}$ alkylene-O—$C_{1-6}$ alkyl, C(=O)—O—$C_{1-6}$alkyl-CN, C(=O)—O—$C_{1-6}$alkyl-OH, C(=O)—O—$C_{1-6}$ alkylene-S—$C_{1-6}$ alkyl, C(=O)—$NHC_{1-6}$alkyl, C(=O)—$NHC_{1-6}$ alkylene-O—$C_{1-6}$ alkyl, C(=O)—$NHC_{1-6}$alkylene-S—$C_{1-6}$ alkyl, C(=O)—$NHC_{1-6}$alkyl-CN, C(=O)—$NHC_{1-6}$alkyl-OH, C(=O)—N($C_{1-6}$alkyl)$_2$, $SO_2$—$C_{1-6}$alkyl, $SO_2$—$C_{1-6}$ alkylene-O—$C_{1-6}$ alkyl, $SO_2$—$C_{1-6}$alkylene-S—$C_{1-6}$ alkyl, $SO_2$—$C_{1-6}$alkyl-CN, $SO_2$—$C_{1-6}$alkyl-OH, $SO_2$—$C_{1-6}$alkyl-N($C_{1-6}$alkyl)$_2$, S—$C_{1-6}$alkyl, $OC_{3-7}$cycloalkyl, $SC_{3-7}$cycloalkyl, $C_{1-6}$alkylene-C(=O)—O—$C_{1-6}$ alkyl, $C_{1-6}$ alkylene-O—C(=O)—NH—$C_{1-6}$ alkyl, $C_{1-6}$ alkylene-NH—C(=O)—$C_{1-6}$ alkylene-O—$C_{1-6}$ alkyl, $C_{1-6}$ alkylene-NH—$SO_2$—$C_{1-6}$ alkyl, $C_{1-6}$ alkylene-NH—$SO_2$—$C_{1-6}$ alkylene-phenyl, $C_{1-6}$alkylene-$NR^cR^d$, $C_{1-6}$alkylene-C(=O)—$NR^eR^f$, $C_{1-6}$alkylene-$R^g$, $C_{1-6}$alkylene-$R^h$, $C_{1-6}$ alkylene-$R^j$, it means that one such group or atom may be linked covalently to any one of the carbon atoms of the $C_{1-6}$ alkyl or $C_{1-6}$ alkylene.

The term "halogen" as used herein means an atom selected from Chloro (Cl), Flouro (F), Iodo (I) and Bromo (Br).

The term "a heteroaryl" as used herein means a mono or bicyclic aromatic ring system containing one or more heteroatoms, such as 1-10, e.g. 1-6, selected from O, S, and N, including but not limited to oxazolyl, oxadiazolyl, thiophenyl, thiadiazolyl, thiazolyl, pyridyl, pyrimidinyl, pyridonyl, pyrimidonyl, quinolinyl, azaquionolyl, isoquinolinyl, azaisoquinolyl, quinazolinyl, azaquinazolinyl, bensozazoyl, azabensoxazoyl, bensothiazoyl, or azabensothiazoyl.

The term "an aryl" as used herein means a mono or bicyclic aromatic ring system containing at least 6 carbon atoms, such as 6, or 10, e.g. phenyl, or naphthyl.

The term "an aliphatic heterocycle" as used herein means a mono or bicyclic 3-10 membered aliphatic heterocycle containing one or more heteroatoms, such as 1-7, e.g. 1-5, selected from O, S, and N, including but not limited to aziridinyl, oxaziridinyl, azetidinyl, diazetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, tetrahydropyranyl, tetrahydrothipyranyl, piperidonyl, or 2-oxa-6-azaspiro[3.3]-heptanyl.

When "R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms" is substituted at the two to six further carbon atoms with a group selected from $C_{1-6}$ alkyl; oxo; OH; $C_{1-6}$alkylene-OH; C(=O)—$C_{1-6}$ alkyl; C(=O)—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$alkylene-$NR^mR^n$, wherein $R^m$ and $R^n$ are independently a group selected from H and $C_{1-6}$ alkyl; such group, e.g. one or two groups, may be linked to any of the two to six further carbon atoms of the aliphatic heterocycle, however not the nitrogen and the adjacent carbonyl, as long as such substitution does not provide an unstable heterocycle.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures
Automated Patch Clamping

Automated whole cell patch-clamp recordings were performed using a QPatch 16 HT system and single-hole Qplates (Biolin Scientific, Sophion, Denmark) on HEK-293 cells stably expressing the human SK3 channel (h$K_{Ca}$2.3). Cells were cultured and prepared for experiments using normal cell culturing procedures. A total of 4-5 million cells were used per experiment. The Qpatch automatically generates giga sealing, whole-cell formation, compound application and recording of current. h$K_{Ca}$2.3 currents were recorded in symmetrical $K^+$ solutions, with an intracellular solution consisting of in mM: KCl 108; KOH/EGTA (ethylene glycol-bis(2-aminoethylether)-N,N,N',N'-tetraacetic acid) 31.25/10; $CaCl_2$ 8.1; $MgCl_2$ 1.2; HEPES (2-[4-(2-hydroxyethyl)piperazin-1-yl]ethanesulfonic acid) 10; KOH 15, pH adjusted to pH=7.2 with HCl. The free calcium concentration was calculated to 400 nM. The extracellular solution consisted of in mM: KCl 150; $CaCl_2$ 0.1; $MgCl_2$ 3; HEPES 10; Glucose 10, pH=7.4 with KOH. The cells were held at 0 mV and h$K_{Ca}$2.3 currents were elicited by a linear voltage ramp from −80 mV to +80 mV (200 ms in duration) applied every 5th second. The compound application protocol consisted of 12 recording periods lasting from 50-200 s: 1) Baseline recordings in extracellular solution; 2) Application of the positive control N-methyl bicuculline (100 µM), which is characterized by full efficacy, fast on- and off-rate; 3-4) Wash-out; 5-9) Increasing concentrations of test compound to establish an IC50 value; 10-11) Wash-out; 12) positive control with compound NS8593 (N-[(1R)-1,2,3,4-tetrahydro-1-naphthalenyl]-1H-benzimidazol-2-amine) (1 µM). Data were sampled at 10 kHz, 4th order Bessel filter, cut-off frequency 3 kHz. Currents were compensated for run-down. Potency was quantified as the concentration needed to inhibit half of the SK channel activity and reported as an IC50 value. All effects of compounds of the present invention as tested were normalized to the observed inhibitory effect of N-methyl bicuculline.

Results

The examples described are potent inhibitors of the SK3 channel and have shown the following $IC_{50}$ in the Automated patch clamping assay described above:

Examples: 1, 2, 3, 4, 5, 6, 7, 8, 9, 10, 10a, 10b, 11, 12, 13, 14, 14a, 14b, 15, 16, 17, 18, 18a, 18b, 19, 19a, 19b, 20, 21, 22, 22a, 22b all have an $IC_{50}$ below 10 µM.

Materials and Methods

Commercial reagents were used without further purification unless otherwise stated. Analytical TLC was performed on silica gel 60-$F_{254}$ (Merck) with detection by fluorescence and by immersion in a $KMnO_4$ solution [$KMnO_4$ solution recipe: Dissolve 1.5 g $KMnO_4$, 10 g $K_2CO_3$, and 1.25 mL 10% NaOH in 200 mL of water] followed by charring. Purification of compound was carried out by column chromatography on silica gel (60-120 mesh, Swambe Chemicals, India). NMR spectra such as $^1H$, $^{13}C$ and 2D COSY were recorded with Bruker AV 400 MHz spectrometer (400 MHz for $^1H$, 100 MHz for $^{13}C$) at ambient temperature by using deuterated DMSO-d6, $CDCl_3$,$CD_3CO_2D$ (AcOH-d4) or $CD_3OD$ as a solvent for NMR. Chemical shifts are reported in δ parts per million (ppm). ESI-MS was recorded on Agilent LC1200 series MS single quadrupole 6130 mass spectrometer.

Abbreviations Used in Experimental Section

BOP=(Benzotriazol-1-yloxy)tris(dimethylamino)phosphonium hexafluorophosphate
PyBOP=(Benzotriazol-1-yloxy)tripyrrolidinophosphonium hexafluorophosphate
EDC.HCl=N-(3-Dimethylaminopropyl)-N'-ethylcarbodiimide hydrochloride
HBTU=N,N,N',N'-Tetramethyl-O-(1H-benzotriazol-1-yl) uronium hexafluorophosphate.
DCM=Dichloromethane; DMF=N,N-Dimethylformamide; TEA=Triethylamine
TFA=Trifluoroacetic acid; Boc-anhydride=Di-tert-butyl dicarbonate; THF=Tetrahydrofuran; t-BuOH=2-Methyl-propan-2-ol; DEA=Diethylamine; DIEA=Ethylbis(propan-2-yl)amine; IPA=Propan-2-ol; Pd/C=Palladium on Carbon; RT=Ambient Temperature; MeOH=Methanol.

Grace Flash Chromatography System:

The Grace REVELERIS® Prep Purification System was used to perform sample purification by flash chromatography, using Flash Cartridges pre-packed with silica:
Columns Used:
Hi-Purit Flash Columns Silica (Normal Phase);
12 g, 60 A, max pressure 350 psi (24 bar),
24 g, 60 A, max pressure 350 psi (24 bar),
40 g, 60 A, max pressure 350 psi (24 bar),
80 g, 60 A, max pressure 350 psi (24 bar).
Solvents: Hexane, EtOAc, $CHCl_3$ and MeOH.

Example 1: Preparation of N-{2-[(1H-1,3-benzodiazol-2-yl)amino]-2-[3-(trifluoromethyl)phenyl]ethyl}-1,2-oxazole-3-carboxamide

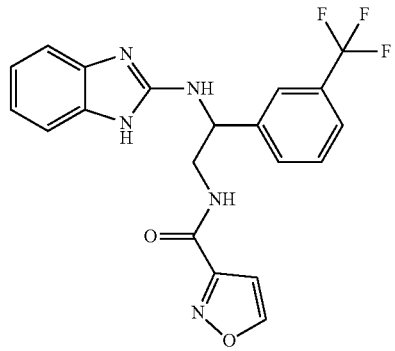 [SMILES: O=C(NCC(Nc1nc2ccccc2[nH]1)c1cccc(C(F)(F)F)c1)c1ccon1]

Step 1: Preparation of 2-{[(tert-butoxy)carbonyl]amino}-2-[3-(trifluoromethyl)phenyl]acetic acid

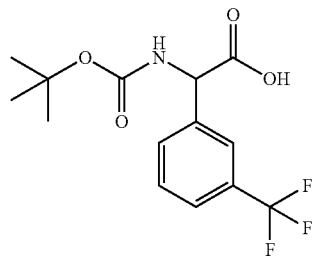 [SMILES: CC(C)(C)OC(=O)NC(C(=O)O)c1cccc(C(F)(F)F)c1]

To a suspension of 2-amino-2-(3-(trifluoromethyl) phenyl) acetic acid (commercially available) (200 g, 913 mmol) in t-BuOH (2500 mL) cooled to 0° C. was added sodium hydroxide pellets (36 g, 892 mmol) solution with water (1000 mL), this solution was stirred for 10 min and Boc anhydride (289.6 g, 1339 mmol) was added portionwise.

The mixture was then warmed to ambient temperature and stirred for 18 h. The reaction mixture was concentrated to remove t-Butanol and diluted with water and the pH was adjusted up to 5-6 with solid citric acid and extracted with ethyl acetate (3×1500 mL). The combined organic layer were dried over anhydrous sodium sulphate and evaporated to afford 2-{[(tert-butoxy)carbonyl]amino}-2-[3-(trifluoromethyl)phenyl]acetic acid (200 g) as a colourless gum which was used in the next step without further purification.

$^1$HNMR (400 MHz, DMSO-$d_6$) δ 12.98 (bs, 1H), 7.81 (d, 1H, J=9.20 Hz), 7.72 (dd, 2H, J=17.2, 7.60 Hz), 7.59 (t, 1H, J=8.00 Hz), 5.28 (d, 1H, J=8.40 Hz), 1.39 (s, 9H);

MS: m/z 318 ((M−1)).

Step 2: Preparation of tert-butyl N-{2-hydroxy-1-[3-(trifluoromethyl)phenyl]ethyl} carbamate

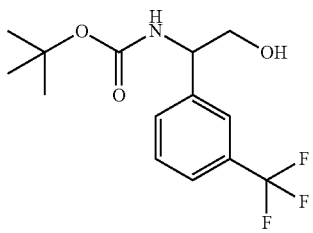 [SMILES: CC(C)(C)OC(=O)NC(CO)c1cccc(C(F)(F)F)c1]

To a suspension of 2-{[(tert-butoxy)carbonyl]amino}-2-[3-(trifluoromethyl)phenyl]acetic acid (from Step 1) (50 g, 157.70 mmol) in tetrahydrofuran (THF) (150 mL) was added triethyl amine (24.61 mL, d=0.726 g/cm$^3$, 175.40 mmol) and isobutyl chloroformate (20.49 g, 157.70 mmol) at 0° C. and stirred at same temperature for 4 h. The solid formed was filter off at 0° C. and the residue was washed with THF (50 mL). The combined filtrate was added to a cooled mixture of sodium borohydride (14.19 g, 383.50 mmol) in water (100 mL). The reaction mass was slowly warmed to ambient temperature for 30 h. The reaction mass was quenched with ice cold water (500 mL) and extracted with ethyl acetate (3×1000 mL) and the combined organic layer was washed with brine (50 mL). The organic layer was dried over sodium sulphate, filtered and concentrated to afford yellowish liquid (41 g) which was purified by column chromatography by using 35% ethyl acetate in petroleum ether to afford tert-butyl N-{2-hydroxy-1-[3-(trifluoromethyl)phenyl]ethyl}carbamate (28 g) as off-white solid.

$^1$H NMR (400 MHz, DMSO-$d_6$) δ 7.64 (s, 1H), 7.60-7.52 (m, 3H), 7.37 (d, 1H, J=8.00 Hz), 4.86 (t, 1H, J=6.00 Hz), 4.60 (d, 1H, J=6.80 Hz), 3.55-3.48 (m, 2H), 1.36 (s, 9H);

MS: m/z 206 [(M+1)-Boc].

Step 3: Preparation of tert-butyl N-[2-(methanesulfonyloxy)-1-[3-(trifluoromethyl)phenyl] ethyl] carbamate

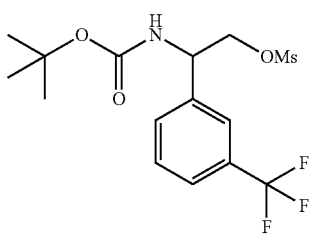 [SMILES: CC(C)(C)OC(=O)NC(COS(C)(=O)=O)c1cccc(C(F)(F)F)c1]

To a solution of tert-butyl N-{2-hydroxy-1-[3-(trifluoromethyl)phenyl]ethyl}carbamate (from Step 2) (10 g, 33.0 mmol) in dichloromethane (100 mL), was added TEA (13.69 ml, d=0.726 g/cm$^3$, 98.0 mmol) at 0° C., followed by mesyl chloride (6.72 mL, 49.0 mmol). The reaction mixture was allowed to attain ambient temperature and stirred for 2 h. The reaction mixture was diluted with water (200 mL) and extracted with dichloromethane (2×200 mL), dried over sodium sulphate, filtered and concentrated to afford tert-butyl N-[2-(methanesulfonyloxy)-1-[3-(trifluoromethyl)phenyl]ethyl]carbamate (15 g) as brown liquid which was used in the next step without further purification.

$^1$H NMR (400 MHz, DMSO-$d_6$) δ 7.86 (bs, 1H), 7.79 (d, 1H, J=11.8 Hz), 7.70 (t, 2H, J=8.2 Hz), 7.62 (t, 1H, J=8.00 Hz), 5.03 (d, 1H, J=6.92 Hz), 4.33-4.26 (m, 2H), 3.11 (s, 3H), 1.39 (s, 9H);

MS: m/z 284 [(M+1)-Boc].

Step 4: Preparation of tert-butyl N-{2-azido-1-[3-(trifluoromethyl)phenyl]ethyl}carbamate

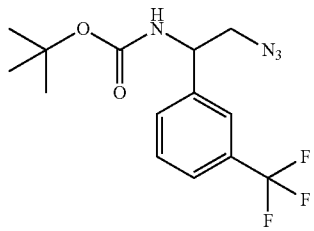 [SMILES: CC(C)(C)OC(=O)NC(CN=[N+]=[N-])c1cccc(C(F)(F)F)c1]

To a suspension of tert-butyl N-[2-(methanesulfonyloxy)-1-[3-(trifluoromethyl)phenyl]ethyl]carbamate (from Step 3) (7 g, 18.0 mmol) in DMF (70 mL) was added sodium azide (5.9 g, 91.0 mmol). The mixture was then heated to 50° C. and stirred for 5 h. The reaction mixture was concentrated to remove DMF and diluted with water (100 mL) and extracted with ethyl acetate (3×100 mL). Combined organic layer was dried over sodium sulphate, filtered and concentrated to afford a crude product (9 g) as a brownish gum, which was purified by silica gel (230-400 mesh) column chromatography eluted with 3% methanol in dichloromethane to afford tert-butyl N-{2-azido-1-[3-(trifluoromethyl)phenyl]ethyl}carbamate as (5.5 g) as an off-white solid.

$^1$H NMR (400 MHz, DMSO-$d_6$) δ 7.78 (d, 2H, J=10.40 Hz), 7.67 (dd, 2H, J=13.80, 7.60 Hz), 7.60 (t, 1H, J=7.60 Hz), 4.86 (dd, 1H, J=14.80, 8.00 Hz), 3.50 (d, 2H, J=8.00 Hz), 1.39 (s, 9H);

MS: m/z 329 (M−1).

Step 5: Preparation of 2-azido-1-[3-(trifluoromethyl)phenyl]ethan-1-amine hydrochloride

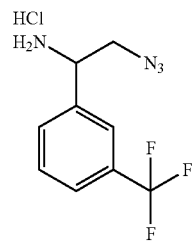

To a suspension of tert-butyl N-{2-azido-1-[3-(trifluoromethyl)phenyl]ethyl}carbamate (from Step 4) (3 g, 9.0 mmol) in DCM (30 mL) was added 4M HCl in dioxane (20 mL) at 0° C. and then allowed to warm to ambient temperature and stirred for 1 h. The reaction mixture was concentrated to afford 2-azido-1-[3-(trifluoromethyl)phenyl]ethan-1-amine hydrochloride desired product (2.2 g) as white solid which was used in the next step without further purification.

1H-NMR (400 MHz, DMSO-d$_6$/D$_2$O): δ 7.93 (s, 1H), 7.81 (t, 2H, J=9.2 Hz), 7.70 (t, 1H, J=7.60 Hz), 4.66 (t, 1H, J=8.0 Hz), 3.91 (dd, 1H, J=7.2 Hz), 3.81 (dd, 1H, J=9.6 Hz); MS: m/z 231 (M+1).

Step 6: Preparation of 1-(2-azido-1-isothiocyanatoethyl)-3-(trifluoromethyl)benzene

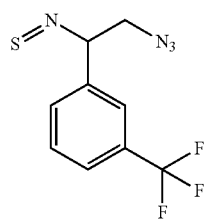 [SMILES: [N-]=[N+]=NCC(N=S)c1cccc(C(F)(F)F)c1]

To a suspension of 2-azido-1-[3-(trifluoromethyl)phenyl] ethan-1-amine hydrochloride (from Step 5) (2.2 g, 8.0 mmol) in dichloromethane (30 mL) was added thiophosgene (1.7 mL, d=1.5 g/cm$^3$, 10.0 mmol) at 0° C. followed by 10% aqueous sodium bicarbonate solution (30 mL) and the reaction mixture was stirred at ambient temperature for 1 h. The organic layer was separated from reaction mass and further the aqueous layer was extracted with DCM (3×50 mL). The combined organic extracts were dried over anhydrous sodium sulphate, evaporated to dryness to afford 1-(2-azido-1-isothiocyanatoethyl)-3-(trifluoromethyl)benzene (2 g) as red gum which was used in the next step without further purification.

$^1$H NMR (400 MHz, DMSO-d$_6$) δ 7.79 (t, 2H, J=8.00 Hz), 7.72-7.64 (m, 2H), 5.56 (t, 1H, J=6.00 Hz), 3.90 (d, 2H, J=6.00 Hz);

Step 7: Preparation of 3-{2-azido-1-[3-(trifluoromethyl)phenyl]ethyl}-1-phenylthiourea

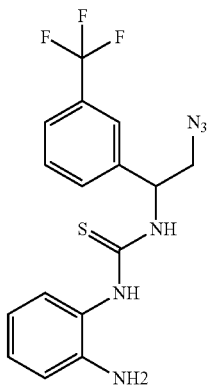 [SMILES: [N-]=[N+]=NCC(NC(=S)Nc1ccccc1N)c1cccc(C(F)(F)F)c1]

A mixture of 1-(2-azido-1-isothiocyanatoethyl)-3-(trifluoromethyl)benzene (from Step 6) (3 g, 11.0 mmol) and benzene-1, 2-diamine (1 g, 9.0 mmol) in dichloromethane (50 mL) was stirred at ambient temperature for 12 h. The reaction mixture was concentrated to afford a crude product (4.5 g) as a brownish gum, which was purified by silica gel (230-400 mesh) flash column chromatography eluted with 8% methanol in chloroform to afford 3-{2-azido-1-[3-(trifluoromethyl)phenyl]ethyl}-1-phenylthiourea (2.5 g) as brownish solid.

$^1$H NMR (400 MHz, DMSO-d$_6$) δ 9.06 (s, 1H, Exchangeable), 7.78 (s, 1H, Exchangeable), 7.72 (d, 1H, J=7.60 Hz), 7.67-7.55 (m, 3H), 7.01-6.95 (m, 2H), 6.77 (d, 1H, J=7.60 Hz), 6.58 (t, 1H, J=7.20 Hz), 5.86 (s, 1H), 4.83 (s, 2H, Exchangeable), 3.85 (dd, 1H, J=12.4, 7.6 Hz), 3.72 (dd, 1H, J=12.8, 4.8 Hz);

MS: m/z 381 (M+1).

Step 8: Preparation of N-{2-azido-1-[3-(trifluoromethyl)phenyl]ethyl}-1H-1,3-benzodiazol-2-amine

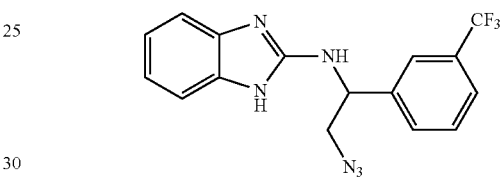

To a solution of 3-{2-azido-1-[3-(trifluoromethyl)phenyl]ethyl}-1-phenylthiourea (from Step 7) (2.5 g, 6.57 mmol) in methanol (10 mL) was added iodoacetic acid (1.2 g, 7.0 mmol) and the mixture was refluxed for 2 h. The reaction mixture was evaporated to afford the crude product (3 g) which was purified by silica gel (230-400 mesh) column chromatography using 5% methanol in dichloromethane as eluent to afford N-{2-azido-1-[3-(trifluoromethyl)phenyl]ethyl}-1H-1,3-benzodiazol-2-amine (1.5 g) as an off-brown solid.

$^1$HNMR (400 MHz, DMSO-d$_6$) δ 11.0 (br.s, 1H), 7.90 (s, 1H), 7.81 (d, 1H, J=7.40 Hz), 7.66-7.59 (m, 3H), 7.14 (dd, 2H, J=5.3, 3.6 Hz), 6.88 (dd, 2H, J=5.72, 3.16 Hz), 5.26 (d, 1H, J=5.60 Hz), 3.77 (dd, 1H, J=12.6, 8.0 Hz), 3.72 (dd, 1H, J=12.6, 8.0 Hz);

MS: m/z 347 (M+1).

Step 9: Preparation of N1-(1H-1,3-benzodiazol-2-yl)-1-[3-(trifluoromethyl)phenyl] ethane-1,2-diamine hydrochloride

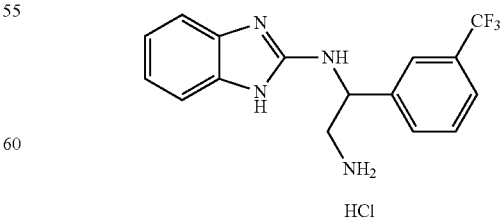

To a solution of N-{2-azido-1-[3-(trifluoromethyl)phenyl]ethyl}-1H-1,3-benzodiazol-2-amine (from Step 8) (1.5 g, 4.3 mmol) in methanol (50 mL) was added Pd/C (10%)

(0.50 g) and the reaction was placed in an autoclave under hydrogen atmosphere at 71.12 Psi pressure for 15 h. The reaction mixture was filtered through a bed of celite and washed with methanol. To the organic layer was added conc. HCl (3 drops) and evaporated to afford N1-(1H-1,3-benzodiazol-2-yl)-1-[3-(trifluoromethyl)phenyl]ethane-1,2-diamine hydrochloride (1 g) as brown solid which was used for next step without further purification.

$^1$H NMR (400 MHz, DMSO-$d_6$) δ 13.22 (br.s, 2H), 10.34 (br.s, 1H), 8.53 (s, 2H), 8.06 (s, 1H), 7.96 (d, 1H, J=7.64 Hz), 7.74 (d, 1H, J=7.8 Hz), 7.68 (t, 1H, J=7.7 Hz), 7.43-7.36 (m, 2H), 7.24-7.12 (m, 2H), 5.36 (bs, 1H), 3.38-3.33 (m, 2H);

MS: m/z 321 (M+1).

Example 1, Step 10: Preparation of N-{2-[(1H-1,3-benzodiazol-2-yl)amino]-2-[3-(trifluoromethyl)phenyl]ethyl}-1,2-oxazole-3-carboxamide

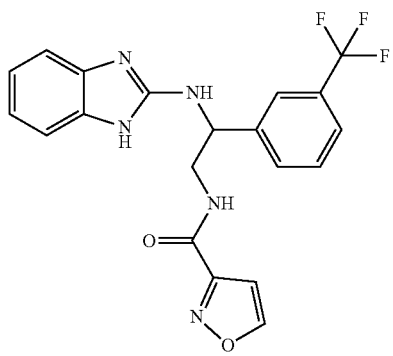 [SMILES: O=C(NCC(Nc1nc2ccccc2[nH]1)c1cccc(C(F)(F)F)c1)c1ccon1]

To a solution of N1-(1H-1,3-benzodiazol-2-yl)-1-[3-(trifluoromethyl)phenyl]ethane-1,2-diamine hydrochloride (from Step 9) (0.25 g, 0.701 mmol) in THF (20 mL) was added triethylamine (0.43 mL, d=0.726 g/cm$^3$, 2.102 mmol) followed by Py-BOP (0.548 g, 1.051 mmol) and the mixture was stirred at ambient temperature. After 15 minutes isoxazole-3-carboxylic acid was added (0.097 g, 0.858 mmol) and the reaction mass was stirred at ambient temperature for 16 h. Then the reaction mass was diluted with 10% aqueous sodium bicarbonate solution (25 mL) and the aqueous layer was extracted with ethyl acetate (3×100 mL). The combined organic layer were washed with saturated brine solution (30 mL), dried over sodium sulphate, filtered and concentrated to afford crude product (0.330 g) which was purified by Grace (24.0 g pre-packed cartridge was used) using 6% methanol in chloroform as eluent to afford N-{2-[(1H-1,3-benzodiazol-2-yl)amino]-2-[3-(trifluoromethyl)phenyl]ethyl}-1,2-oxazole-3-carboxamide (0.110 g) as an off-white solid.

$^1$H NMR (400 MHz, AcOH-$d_4$) δ 8.68 (d, 1H, J=1.2 Hz), 7.86 (t, 2H, J=7.2 Hz), 7.67 (d, 1H, J=7.6 Hz), 7.61 (t, 1H, J=7.6 Hz), 7.37 (dd, 2H, J=5.6, 2.8 Hz), 7.21 (dd, 2H, J=6.0, 3.2 Hz), 6.88 (d, 1H, J=1.6 Hz), 5.40 (dd, 1H, J=8.0, 4.8 Hz), 4.06 (dd, 1H, J=14.4, 4.8 Hz), 3.92 (dd, 1H, J=14.0, 8.8 Hz); MS: m/z 416.1 (M+1).

Example 2: Preparation of N-{2-[(1H-1,3-benzodiazol-2-yl)amino]-2-[3-(trifluoromethyl)phenyl]ethyl}cyclobutanecarboxamide

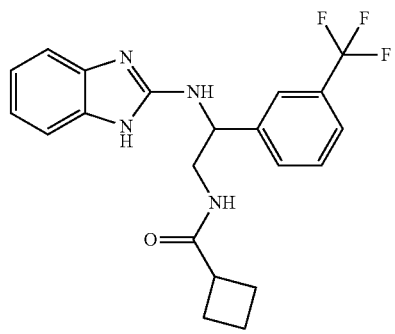 [SMILES: O=C(NCC(Nc1nc2ccccc2[nH]1)c1cccc(C(F)(F)F)c1)C1CCC1]

To a solution of N1-(1H-1,3-benzodiazol-2-yl)-1-[3-(trifluoromethyl)phenyl]ethane-1,2-diamine hydrochloride (from Example 1, Step 9) (0.25 g, 0.701 mmol) in THF (20 mL) was added triethylamine (0.3 mL, d=0.726 g/cm$^3$, 2.102 mmol) followed by Py-BOP (0.548 g, 1.051 mmol) and the mixture was stirred at ambient temperature. After 15 minutes, cyclobutane carboxylic acid (0.070 g, 0.590 mmol) was added and the stirring was continued for 16 h. The reaction mass was diluted with 10% aqueous sodium bicarbonate solution (25 mL) and the aqueous layer was extracted with ethyl acetate (3×100 mL). The combined organic layer was washed with brine solution (30 mL), dried over sodium sulphate, filtered and concentrated to afford crude product (0.300 g) which was purified by Grace (24.0 g pre-packed cartridge was used) using 6% methanol in chloroform as eluent to afford N-{2-[(1H-1,3-benzodiazol-2-yl)amino]-2-[3-(trifluoromethyl)phenyl]ethyl}cyclobutanecarboxamide (0.120 g) as an off-white solid.

$^1$H NMR (400 MHz, MeOH-$d_4$) δ 7.80 (s, 1H), 7.74 (d, J=7.2 Hz, 1H), 7.66-7.59 (m, 2H), 7.29-7.27 (m, 2H), 7.15-7.11 (m, 2H), 5.09 (t, 1H, J=6.8 Hz), 3.65 (d, 2H, J=6.8 Hz), 3.05 (t, 1H, J=8.4 Hz), 2.21-2.14 (m, 2H), 2.11-2.09 (m, 2H), 2.07-2.03 (m, 1H), 1.98-1.91 (m, 1H);

MS: m/z 403.1 (M+1)

Example 3: Preparation of N-{2-[(1H-1,3-benzodiazol-2-yl)amino]-2-[3-(trifluoromethyl)phenyl]ethyl}cyclopropanecarboxamide

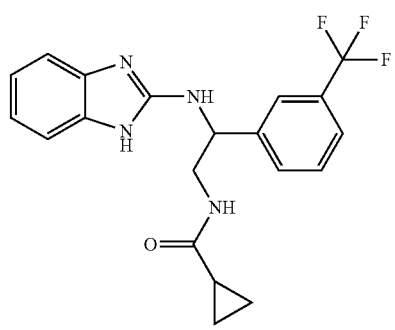 [SMILES: O=C(NCC(Nc1nc2ccccc2[nH]1)c1cccc(C(F)(F)F)c1)C1CC1]

To a solution of N1-(1H-1,3-benzodiazol-2-yl)-1-[3-(trifluoromethyl)phenyl]ethane-1,2-diamine hydrochloride (from Example 1, Step 9) (0.300 g, 0.841 mmol) in THF (20 mL) was added triethylamine (0.3 mL, d=0.726 g/cm³, 2.102 mmol) followed by Py-BOP (0.656 g, 1.261 mmol) and the mixture was stirred at ambient temperature. After 15 minutes, cyclopropanecarboxylic acid (0.065 g, 0.620 mmol) was added and the stirring was continued for 16 h. The reaction mass was diluted with 10% aqueous sodium bi-carbonate solution (25 mL) and the aqueous layer was extracted with ethyl acetate (3×100 mL). The combined organic layer were washed with brine solution (30 mL), dried over sodium sulphate, filtered and concentrated to afford crude product (0. 330 g) which was purified by Grace (24.0 g pre-packed cartridge was used) using 6% methanol in chloroform as eluent to afford N-{2-[(1H-1,3-benzodi-azol-2-yl)amino]-2-[3-(trifluoromethyl)phenyl]ethyl}cyclopropanecarboxamide (0.117 g) as a white solid.

¹H NMR (400 MHz, AcOH-d₄) δ 7.81 (t, 2H, J=7.48 Hz), 7.67 (d, 1H, J=7.7 Hz), 7.62 (d, 1H, J=7.8 Hz), 7.41 (dd, 2H, J=6.0, 3.2 Hz), 7.26 (dd, 2H, J=6.0, 3.2 Hz), 5.36 (dd, 1H, J=8.9, 4.7 Hz), 3.87 (dd, 1H, J=14.2, 9.4 Hz), 3.67 (dd, 1H, J=14.2, 9.1 Hz), 3.20 (dd, 1H, J=6.6, 2.9 Hz), 0.91 (d, 2H, J=4.4 Hz), 0.77-0.72 (m, 2H);

MS: m/z 389.0 (M+1).

Example 4: Preparation of N-{2-[(1H-1,3-benzodi-azol-2-yl)amino]-2-[3-(trifluoromethyl)phenyl]ethyl}-1,2,4-oxadiazole-3-carboxamide; trifluoro-acetic acid

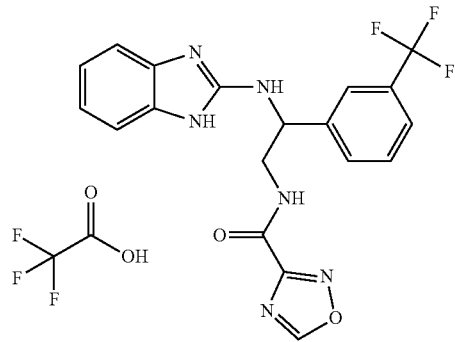 [SMILES: O=C(O)C(F)(F)F ; O=C(NCC(Nc1nc2ccccc2[nH]1)c1cccc(C(F)(F)F)c1)c1ncon1]

To a solution of N1-(1H-1,3-benzodiazol-2-yl)-1-[3-(tri-fluoromethyl)phenyl]ethane-1,2-diamine hydrochloride (from Example 1, Step 9) (0.280 g, 0.785 mmol) in THF (20 mL) was added triethylamine (0.33 mL, d=0.726 g/cm³, 2.355 mmol) followed by Py-BOP (0.613 g, 1.179 mmol) and the mixture was stirred at ambient temperature. After 15 minutes, 1, 2, 4-oxadiazole-3-carboxylic acid (0.090 g, 0.785 mmol) was added and the stirring was continued for 16 h. The reaction mass was diluted with 10% aqueous sodium bicarbonate solution (25 mL) and the aqueous layer was extracted with ethyl acetate (3×100 mL). The combined organic layer was washed with brine solution (30 mL), dried over sodium sulphate, filtered and concentrated to afford crude product (0.420 g) which was purified by preparative HPLC to afford N-{2-[(1H-1,3-benzodiazol-2-yl)amino]-2-[3-(trifluoromethyl)phenyl]ethyl}-1,2,4-oxadiazole-3-car-boxamide; trifluoroacetic acid (0.150 g) as an off-white solid.

¹H NMR (400 MHz, AcOH-d₄) δ 9.2 (s, 1H), 7.89 (t, 2H, J=14.8 Hz), 7.70 (d, 1H, J=8.0 Hz), 7.63 (t, 1H, J=7.6 Hz), 7.38 (dd, 2H, J=6.0, 3.2 Hz), 7.27-7.23 (m, 2H), 5.50 (dd, 1H, J=8.4, 4.4 Hz), 4.10 (dd, 1H, J=14.0, 4.4 Hz), 3.98 (dd, 1H, J=14.0, 8.8 Hz);

MS: m/z 417.1 (M+1).

Example 5: Preparation of N-{2-[(1H-1,3-benzodi-azol-2-yl)amino]-2-[3-(trifluoromethyl)phenyl]ethyl}pyrimidine-4-carboxamide; trifluoroacetic acid

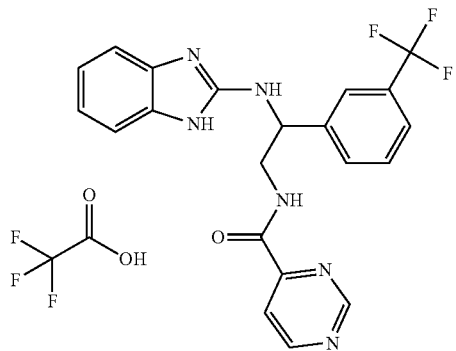

To a solution of N1-(1H-1,3-benzodiazol-2-yl)-1-[3-(tri-fluoromethyl)phenyl]ethane-1,2-diamine hydrochloride (from Example 1, Step 9) (0.25 g, 0.701 mmol) in THF (20 mL) was added triethylamine (0.3 mL, d=0.726 g/cm³, 2.102 mmol) followed by Py-BOP (0.548 g, 1.401 mmol) and the mixture was stirred at ambient temperature. After 15 minutes, pyrimidine-4-carboxylic acid (0.087 g, 0.701 mmol) was added and the stirring was continued for 16 h. The reaction mass was diluted with 10% aqueous sodium bi-carbonate solution (25 mL) and the aqueous layer was extracted with ethyl acetate (3×100 mL). The combined organic layer was washed with brine solution (30 mL), dried over sodium sulphate, filtered and concentrated to afford crude product (0.380 g) which was purified by preparative HPLC to afford N-{2-[(1H-1,3-benzodiazol-2-yl)amino]-2-[3-(trifluoromethyl)phenyl]ethyl}pyrimidine-4-carboxam-ide; trifluoroacetic acid (0.125 g) as an off-white solid.

¹H NMR (400 MHz, AcOH-d₄) δ 9.29 (s, 1H), 9.10 (d, 1H, J=5.12 Hz), 8.18 (d, 1H, J=5.0 Hz), 7.90 (d, 2H, J=7.5 Hz), 7.70 (d, 1H, J=7.7 Hz), 7.74 (t, 1H, J=7.4 Hz), 7.38 (dd, 2H, J=5.7, 3.4 Hz), 7.24 (dd, 2H, J=5.8, 3.0 Hz), 5.43 (s, 1H), 4.09 (d, 2H, J=5.7 Hz);

MS: m/z 427.0 (M+1).

Example 6: Preparation of N-{2-[(1H-1,3-benzodi-azol-2-yl)amino]-2-[3-(trifluoromethyl)phenyl]ethyl}pyridine-2-carboxamide; trifluoroacetic acid

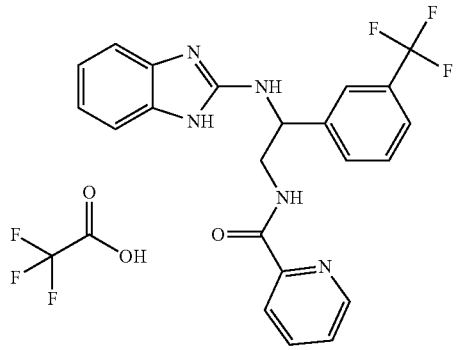 [SMILES: O=C(O)C(F)(F)F ; O=C(NCC(Nc1nc2ccccc2[nH]1)c1cccc(C(F)(F)F)c1)c1ccncn1]

To a solution of N1-(1H-1,3-benzodiazol-2-yl)-1-[3-(trifluoromethyl)phenyl]ethane-1,2-diamine hydrochloride (from Example 1, Step 9) (0.258 g, 0.785 mmol) in THF (20 mL) was added triethylamine (0.33 mL, d=0.726 g/cm$^3$, 2.354 mmol) followed by Py-BOP (0.613 g, 1.57 mmol) and the mixture was stirred at ambient temperature. After 15 minutes, picolinic acid (0.097 g, 0.785 mmol) was added and the stirring was continued for 16 h. Then the reaction mass was diluted with 10% aqueous sodium bi-carbonate solution (25 mL) and the aqueous layer was extracted with ethyl acetate (3×100 mL). The combined organic layer were washed with brine solution (30 mL), dried over sodium sulphate, filtered and concentrated to afford crude product (0.340 g) which was purified by preparative HPLC to afford N-{2-[(1H-1,3-benzodiazol-2-yl)amino]-2-[3-(trifluoromethyl)phenyl]ethyl}pyridine-2-carboxamide; trifluoroacetic acid (0.130 g) as a white solid.

$^1$H NMR (400 MHz, AcOH-d$_4$) δ 8.63 (d, 1H, J=4.4 Hz), 8.24 (d, 1H, J=7.6 Hz), 8.07 (t, 1H, J=7.6 Hz), 7.92 (bs, 1H), 7.89 (d, 1H, J=7.6 Hz), 7.69 (d, 1H, J=7.6 Hz), 7.63 (t, 2H, J=7.6 Hz), 7.38 (dd, 2H, J=6.0, 3.2 Hz), 7.26-7.21 (m, 2H), 5.46 (dd, 1H, J=8.0, 5.2 Hz), 4.14-4.00 (m, 2H);

MS: m/z 426.1 (M+1).

Example 7: Preparation of N-{2-[(1H-1,3-benzodiazol-2-yl)amino]-2-[3-(trifluoromethyl)phenyl]ethyl}-3-cyanobenzamide

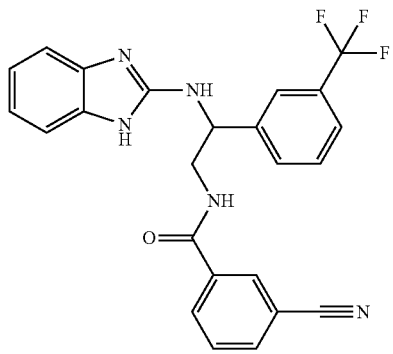 [SMILES: N#Cc1cccc(C(=O)NCC(Nc2nc3ccccc3[nH]2)c2cccc(C(F)(F)F)c2)c1]

To a suspension of N1-(1H-1,3-benzodiazol-2-yl)-1-[3-(trifluoromethyl)phenyl]ethane-1,2-diamine hydrochloride (from Example 1, Step 9) (0.350 g, 0.98 mmol) in dichloromethane (20 mL) was added triethylamine (0.4 mL, d=0.726 g/cm$^3$, 3.0 mmol), PyBop (0.77 g, 1.0 mmol) followed by 3-cyanobenzoic acid (0.28 g, 2.0 mmol) and stirring was continued for 5 h. The reaction mixture was quenched with water (20 mL), extracted with ethyl acetate (3×100 mL). The combined organic layer was dried over sodium sulphate, filtered and concentrated to afford a crude product (0.45 g) as a brownish gum, which was purified by silica gel (230-400 mesh) column chromatography eluting with 7% methanol in DCM to afford N-{2-[(1H-1,3-benzodiazol-2-yl)amino]-2-[3-(trifluoromethyl)phenyl]ethyl}-3-cyanobenzamide (0.21 g) as an off-white solid $^1$H NMR (400 MHz, AcOH-d4) δ 8.19-8.14 (m, 2H), 7.89-7.86 (m, 3H), 7.71-7.60 (m, 3H), 7.37 (dd, 2H, J=5.96, 3.08 Hz), 7.26-7.22 (m, 2H), 5.49 (dd, 1H, J=8.70, 4.64 Hz), 4.09 (dd, 1H, J=14.16, 4.68 Hz), 3.95 (dd, 1H, J=14.16, 8.84 Hz);

MS: m/z 450 (M+1).

Example 8: Preparation of N-{2-[(1H-1,3-benzodiazol-2-yl)amino]-2-[3-(trifluoromethyl)phenyl]ethyl}oxane-4-carboxamide

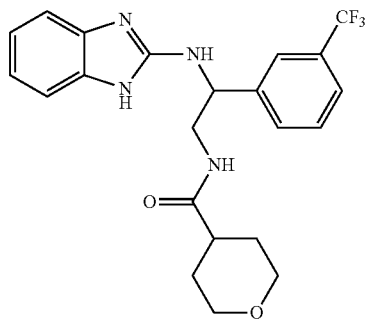 [SMILES: O=C(NCC(Nc1nc2ccccc2[nH]1)c1cccc(C(F)(F)F)c1)C1CCOCC1]

To a suspension of N1-(1H-1,3-benzodiazol-2-yl)-1-[3-(trifluoromethyl)phenyl]ethane-1,2-diamine hydrochloride (from Example 1, Step 9) (0.2 g, 0.56 mmol) in dichloromethane (20 mL) was added triethylamine (0.4 mL, d=0.726 g/cm$^3$, 2.0 mmol) and PyBop (0.43 g, 0.77 mmol) followed by tetrahydro-2H-pyran-4-carboxylic acid (0.10 g, 0.84 mmol) and the reaction mixture was stirred at ambient temperature for 5 h. The reaction mixture was quenched with water (50 mL), extracted with dichloromethane (3×100 mL). The combined organic layer was dried over sodium sulphate, filtered and concentrated to afford a crude product (0.3 g) as a brownish gum, which was purified by silica gel (230-400 mesh) column chromatography eluted with 7% methanol in dichloromethane to afford N-{2-[(1H-1,3-benzodiazol-2-yl)amino]-2-[3-(trifluoromethyl)phenyl]ethyl}oxane-4-carboxamide (0.09 g) as an off-white solid.

$^1$H NMR (400 MHz, AcOH-d$_4$) δ 7.81 (t, J=7.60 Hz, 2H), 7.69-7.59 (m, 2H), 7.40 (dd, 2H, J=5.80, 2.80 Hz), 7.28-7.23 (m, 2H), 5.39 (dd, 1H, J=4.80, 8.60 Hz), 4.02-3.95 (m, 2H), 3.86 (dd, 1H, J=14.20, 4.80 Hz), 3.70 (dd, 1H, J=14.00, 8.80 Hz), 3.44-3.36 (m, 2H), 2.59-2.53 (m, 1H), 1.74-1.63 (m, 4H);

MS: m/z 433.1 (M+1).

Example 9: Preparation of N-{2-[(1H-1,3-benzodiazol-2-yl)amino]-2-[3-(trifluoromethyl)phenyl]ethyl}-3-fluorobenzamide

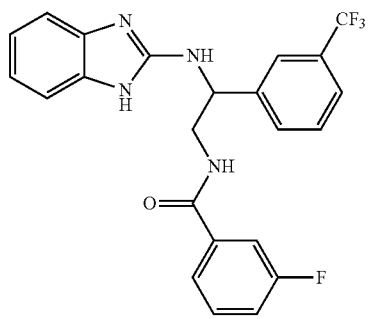 [SMILES: O=C(NCC(Nc1nc2ccccc2[nH]1)c1cccc(C(F)(F)F)c1)c1cccc(F)c1]

To a suspension of N1-(1H-1,3-benzodiazol-2-yl)-1-[3-(trifluoromethyl)phenyl]ethane-1,2-diamine hydrochloride (from Example 1, Step 9) (0.200 g, 0.56 mmol) in dichloromethane (20 mL) was added triethylamine (0.4 mL, d=0.726 g/cm³, 2.0 mmol) and PyBop (0.43 g, 0.84 mmol) followed by 3-fluorobenzoic acid (0.11 g, 0.78 mmol) and the reaction mixture was stirred at ambient temperature for 5 h. The reaction mixture was quenched with water (50 mL), extracted with dichloromethane (3×100 mL). The combined organic layer was dried over sodium sulphate, filtered and concentrated to afford a crude product (0.3 g) as a brownish gum, which was purified by silica gel (230-400 mesh) column chromatography eluting with 7% methanol in DCM to afford N-{2-[(1H-1,3-benzodiazol-2-yl)amino]-2-[3-(trifluoromethyl)phenyl]ethyl}-3-fluorobenzamide (0.09 g) as an off-white solid.

¹H NMR (400 MHz, AcOH-d₄) δ 7.90 (s, 1H), 7.86 (d, 1H, J=7.60 Hz), 7.70-7.58 (m, 4H), 7.47-7.42 (m, 1H), 7.37 (dd, 2H, J=6.00, 3.20 Hz), 7.28-7.23 (m, 3H), 5.50 (dd, J=8.40, 4.80 Hz, 1H), 4.06 (dd, J=14.00, 4.80 Hz, 1H), 3.92 (dd, 1H, J=8.80, 14.00 Hz);

MS: m/z 443.1 (M+1).

Example 10: Preparation of N-{2-[(1H-1,3-benzodiazol-2-yl)amino]-2-[3-(trifluoromethyl)phenyl]ethyl}propanamide

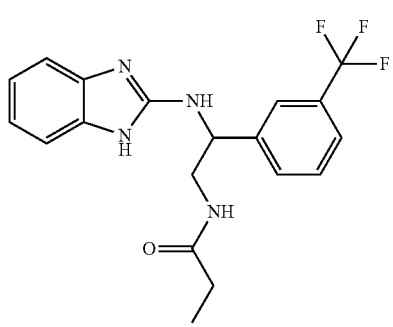 [SMILES: CCC(=O)NCC(Nc1nc2ccccc2[nH]1)c1cccc(C(F)(F)F)c1]

Step 1: Preparation of tert-butyl N-{2-amino-1-[3-(trifluoromethyl)phenyl]ethyl}carbamate

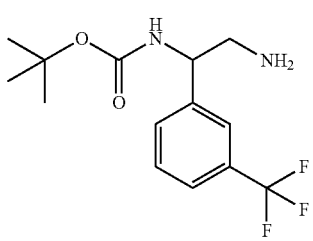 [SMILES: CC(C)(C)OC(=O)NC(CN)c1cccc(C(F)(F)F)c1]

To a solution of tert-butyl N-{2-azido-1-[3-(trifluoromethyl)phenyl]ethyl}carbamate (from Example 1, Step 4) (5 g, 15.147 mmol) in methanol (150 mL) was added Pd/C (10%) (0.100 g) and the mixture was placed in an autoclave under hydrogen atmosphere at 71.12 Psi pressure for 2 h. The reaction mixture was filtered through a bed of celite, washed with methanol (1000 mL) and the organic layer was evaporated to afford tert-butyl N-{2-amino-1-[3-(trifluoromethyl)phenyl]ethyl} carbamate (3.6 g) as beige-solid, which was used in the next step without further purification.

¹H NMR (400 MHz, DMSO-d₆) δ 7.60-7.53 (m, 4H), 7.45 (d, 1H, J=7.2 Hz), 4.50 (d, 1H, J=6.4 Hz), 2.71-2.67 (m, 2H), 1.56 (br.s, 2H), 1.36 (s, 9H);

MS: m/z 305.1 (M+1).

Step 2: Preparation of tert-butyl N-{2-propanamido-1-[3-(trifluoromethyl)phenyl]ethyl} carbamate

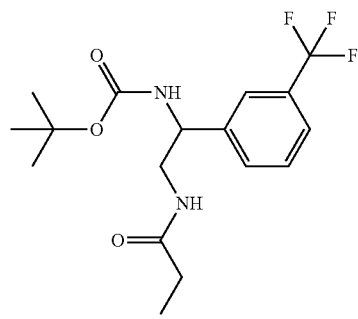 [SMILES: CCC(=O)NCC(NC(=O)OC(C)(C)C)c1cccc(C(F)(F)F)c1]

To a solution of tert-butyl N-{2-amino-1-[3-(trifluoromethyl)phenyl]ethyl} carbamate (from step 1) (2 g, 6.572 mmol) in DCM (100 mL) was added TEA (2.3 mL, d=0.726 g/cm³, 16.431 mmol) at 0° C., followed by propionyl chloride (0.55 mL, d=1.404 g/cm³, 7.886 mmol). The reaction mixture was allowed to attain ambient temperature and stirred for 2 h. The reaction mixture was diluted with water (200 mL) and extracted with dichloromethane (3×200 mL) and the combined organic layer was dried over sodium sulphate, filtered and concentrated to afford a crude product (2.4 g) as a brownish gum, which was purified by silica gel (230-400 mesh) column chromatography eluting with 7% ethyl acetate in hexane to afford tert-butyl N-{2-propanamido-1-[3-(trifluoromethyl)phenyl]ethyl}carbamate (1.3 g) as an off-white solid.

¹H NMR (400 MHz, DMSO-d₆) δ 7.83 (s, 1H), 7.57 (dd, 5H, J=34.4, 14.4 Hz), 4.73 (d, 1H, J=7.6 Hz), 3.21-3.24 (m, 2H), 1.99 (dd, 2H, J=15.2, 7.6 Hz), 1.36 (s, 9H), 0.91 (t, 3H, J=7.6 Hz);

MS: m/z 261.2 [(M+1)-Boc].

Step 3: Preparation of N-{2-amino-2-[3-(trifluoromethyl)phenyl]ethyl}propanamide; trifluoroacetic acid

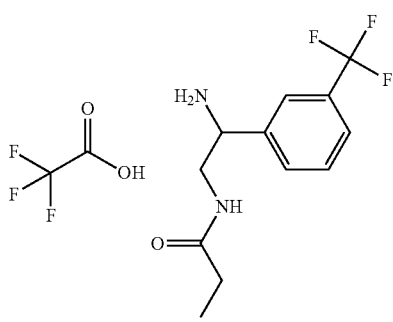 [SMILES: O=C(O)C(F)(F)F ; CCC(=O)NCC(N)c1cccc(C(F)(F)F)c1]

To a suspension tert-butyl N-{2-propanamido-1-[3-(trifluoromethyl)phenyl]ethyl}carbamate (from Step 2) (1.3 g, 3.60 mmol) in DCM (30 mL) was added TFA (6.3 mL, d=1.49 g/cm³, 82.463 mmol) at 0° C. and the reaction mixture was stirred at ambient temperature for 1 h. The reaction mixture was concentrated to afford N-{2-amino-2-[3-(trifluoromethyl)phenyl]ethyl}propanamide; trifluoroacetic acid (1.1 g) as a yellow gum, which was used in the next step without further purification.

¹H NMR (400 MHz, DMSO-d₆) δ 8.46 (bs, 3H), 7.96 (s, 1H), 7.85 (s, 1H), 7.77 (d, 1H, J=7.3 Hz), 7.71 (t, 2H, J=6.0 Hz), 4.56 (d, 1H J=7.6 Hz), 3.55 (d, 1H, J=6.8 Hz), 3.46 (d, 1H, J=6.9 Hz), 2.01 (dd, 2H, J=7.6, 15.2 Hz), 0.92 (t, 3H, J=7.6 Hz);

MS: m/z 261.2 (M+1).

Step 4: Preparation of N-{2-isothiocyanato-2-[3-(trifluoromethyl)phenyl]ethyl}propanamide

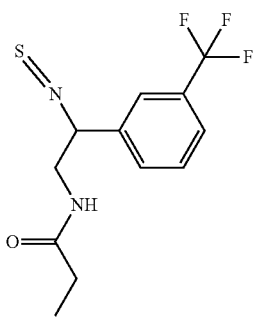 [SMILES: CCC(=O)NCC(N=S)c1cccc(C(F)(F)F)c1]

To a suspension of N-{2-amino-2-[3-(trifluoromethyl)phenyl]ethyl}propanamide; trifluoroacetic acid (from Step 3) (1.1 g, 3.64 mmol) in dichloromethane (30 mL) was added thiophosgene (0.5 mL, d=1.5 g/cm³, 6.33 mmol) followed by 10% aqueous sodium bicarbonate solution (15 mL) at 0° C. The reaction mixture was then stirred at ambient temperature. After 1 h, the reaction mixture was diluted with 10% aqueous sodium bicarbonate solution (20 mL) and extracted with dichloromethane (3×100 mL). The combined organic extracts were dried over anhydrous sodium sulphate, filtered and evaporated to dryness to afford N-{2-isothiocyanato-2-[3-(trifluoromethyl)phenyl]ethyl} propanamide (1.2 g) as a red gum, which was used in the next step without further purification.

¹H NMR (400 MHz, DMSO-d₆) δ 8.21 (d, 1H, J=5.6 Hz), 7.75 (d, 2H, J=6.4 Hz), 7.68 (t, 2H, J=6.8 Hz), 5.36 (dd, 1H, J=7.2, 5.2 Hz), 3.59-3.50 (m, 2H), 2.08 (dd, 2H, J=15.2, 7.6 Hz), 0.97 (t, 3H, J=7.6 Hz);

Step 5: Preparation of N-{2-[(phenylcarbamothioyl)amino]-2-[3-(trifluoromethyl)phenyl]ethyl}propanamide

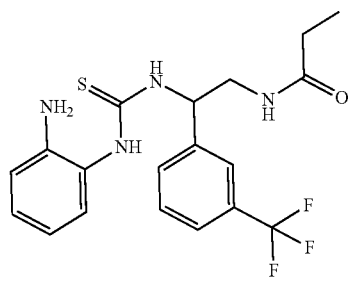 [SMILES: CCC(=O)NCC(NC(=S)Nc1ccccc1N)c1cccc(C(F)(F)F)c1]

A mixture of N-{2-isothiocyanato-2-[3-(trifluoromethyl)phenyl]ethyl}propanamide (from Step 4) (1.2 g, 3.969 mmol) and benzene-1, 2-diamine (0.430 g, 3.969 mmol) in DCM (50 mL) was stirred at ambient temperature for 12 h. The reaction mixture was concentrated to afford a crude product (1.7 g) as a brownish gum, which was purified by silica gel (230-400 mesh) column chromatography eluting with 8% methanol in chloroform to afford N-{2-[(phenylcarbamothioyl)amino]-2-[3-(trifluoromethyl)phenyl]ethyl}propanamide (0.9 g) as a brownish solid.

MS: m/z 411.5 (M+1).

Example 10, Step 6: N-{2-[(1H-1,3-benzodiazol-2-yl)amino]-2-[3-(trifluoromethyl)phenyl]ethyl}propanamide

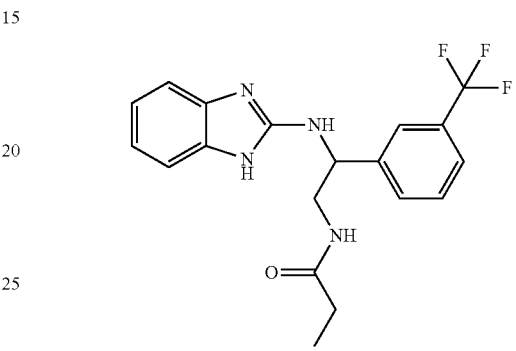

To a solution of N-{2-[(phenylcarbamothioyl)amino]-2-[3-(trifluoromethyl)phenyl]ethyl}propanamide (from Step 5) (0.9 g, 2.193 mmol) in methanol (20 mL) was added iodoacetic acid (0.510 g, 2.741 mmol) and the mixture was refluxed for 2 h. The reaction mixture was evaporated to afford the crude product (1 g) which was purified by silica gel (230-400 mesh) column chromatography using 5% methanol in dichloro methane as eluent to afford N-{2-[(1H-1,3-benzodiazol-2-yl)amino]-2-[3-(trifluoromethyl)phenyl]ethyl}propanamide (0.2 g) as a brown solid.

¹H NMR (400 MHz, DMSO-d₆/D₂O) δ 7.74 (s, 1H), 7.70 (d, 1H, J=7.2 Hz), 7.60-7.53 (m, 2H), 7.10 (d, 2H, J=8.8 Hz), 6.90-6.81 (m, 2H), 5.06 (t, 1H, J=7.2 Hz), 3.44 (d, 2H, J=6.8 Hz), 2.01 (dd, 2H, J=15.2, 7.2 Hz), 0.90 (t, 3H, J=7.6 Hz)

The above product was resolved into its enantiomers by Chiral SFC using Column: Lux C₄ and Co-Solvent: 20 mM Ammonia in IPA (Co-Solvent %:40) with CO₂.

Example 10a: N-{2-[(1H-1,3-benzodiazol-2-yl)amino]-2-[3-(trifluoromethyl)phenyl]ethyl}propanamide: Isomer 1

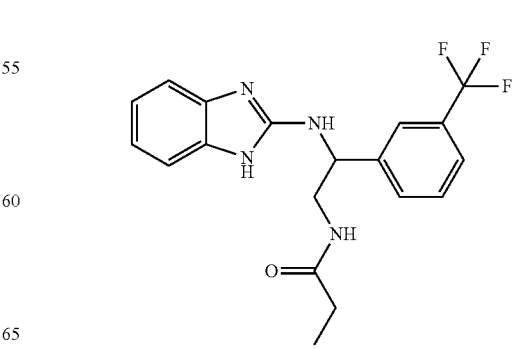

The first enantiomer to elute off the column:
¹H NMR (400 MHz, DMSO-d₆) δ 10.90 (s, 1H, exchangeable), 8.00 (t, 1H, J=5.6 Hz, exchangeable), 7.75 (s, 1H), 7.69 (d, 1H, J=7.2 Hz), 7.59-7.53 (m, 2H), 7.30 (d, 1H, J=8.4 Hz, exchangeable), 7.08 (d, 2H, J=8.0 Hz), 6.89-6.79 (m, 2H), 5.08 (dd, 1H, J=6.8, 14.8 Hz), 3.45 (t, 2H, J=6.8 Hz), 2.01 (dd, 2H, J=15.2, 7.6 Hz), 0.93 (t, 3H, J=7.6 Hz);
MS: m/z 377.2 (M+1).

Example 10b: N-{2-[(1H-1,3-benzodiazol-2-yl)amino]-2-[3-(trifluoromethyl)phenyl]ethyl}propanamide, Isomer 2

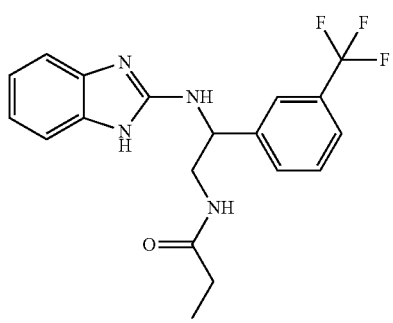 [SMILES: CCC(=O)NCC(Nc1nc2ccccc2[nH]1)c1cccc(C(F)(F)F)c1]

The second enantiomer to elute off the column.
¹H NMR (400 MHz, DMSO-d₆) δ 10.92 (s, 1H, exchangeable), 8.00 (t, 1H, J=6.0 Hz, exchangeable), 7.75 (s, 1H), 7.70 (d, 1H, J=6.8 Hz), 7.60-7.53 (m, 2H), 7.31 (d, 1H, J=8.4 Hz, exchangeable), 7.08 (d, 2H, J=7.6 Hz), 6.88-6.79 (m, 2H), 5.09 (dd, 1H, J=14.8, 7.2 Hz), 3.45 (t, 2H, J=6.8 Hz), 2.01 (dd, 2H, J=15.6, 7.6 Hz), 0.91 (t, 3H, J=6.8 Hz);
MS: m/z 377.2 (M+1).

Example 11: Preparation of 1-{2-[(1H-1,3-benzodiazol-2-yl)amino]-2-[3-(trifluoromethyl)phenyl]ethyl}pyrrolidin-2-one

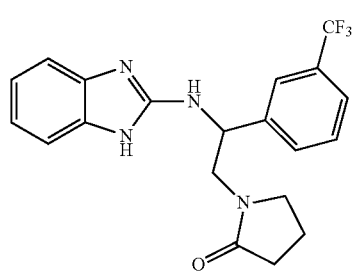 [SMILES: O=C1CCCN1CC(Nc1nc2ccccc2[nH]1)c1cccc(C(F)(F)F)c1]

Step 1: Preparation of tert-butyl N-{2-bromo-1-[3-(trifluoromethyl)phenyl]ethyl}carbamate

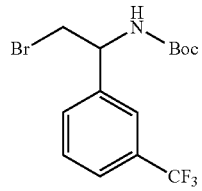

To a solution of tert-butyl N-{2-hydroxy-1-[3-(trifluoromethyl)phenyl]ethyl}carbamate (from Example 1, step 2) (27.5 g, 90.1 mmol) in dichloromethane (1250 mL), was added triphenylphosphine (35.43 g, 135.1 mmol) followed by tetrabromomethane (35.84 g, 108.1 mmol) at 0° C. and stirred at room temperature for 16 h. The reaction mixture was concentrated to afford a crude product as a yellowish liquid, which was purified by silica gel (60-120 mesh) column chromatography eluting with 80% chloroform in petroleum ether to afford tert-butyl N-{2-bromo-1-[3-(trifluoromethyl)phenyl]ethyl}carbamate (9.0 g) as a white solid.
¹H NMR (400 MHz, DMSO-d₆) δ 7.77-7.59 (m, 5H), 4.90 (s, 1H), 3.65 (dd, J=8.40, Hz, 2H), 1.37 (s, 9H);

Step 2: Preparation of tert-butyl N-[2-(2-oxopyrrolidin-1-yl)-1-[3-(trifluoromethyl)phenyl]ethyl]carbamate

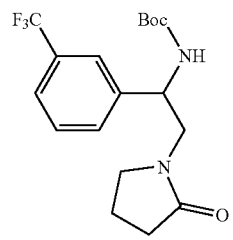

To a solution of pyrrolidin-2-one (2.42 g, 29 mmol) in N,N-dimethylformamide (50 mL) was added cesium carbonate (22.3 g, 68 mmol) and stirred at room temperature for 1.5 h. Then tert-butyl N-{2-bromo-1-[3-(trifluoromethyl)phenyl]ethyl}carbamate (from step 1)(4.2 g, 11 mmol) was added and the reaction mixture was heated at 80° C. for 16 h. The reaction mixture was filtered and concentrated to afford (5 g) of a reddish liquid, which was purified by preparative HPLC to afford tert-butyl N-[2-(2-oxopyrrolidin-1-yl)-1-[3-(trifluoromethyl)phenyl]ethyl]carbamate (0.55 g) as a white solid.
¹H NMR (400 MHz, DMSO-d₆) δ 7.73-7.57 (m, 5H), 5.26-4.85 (m, 1H), 3.53-3.29 (m, 4H), 2.26-2.11 (m, 2H), 1.84 (t, J=7.60 Hz, 2H), 1.34 (s, 9H);
MS: m/z 273.2 (M+1) (loss of Boc).

Step 3: Preparation of 1-{2-amino-2-[3-(trifluoromethyl)phenyl]ethyl}pyrrolidin-2-one; trifluoroacetic acid

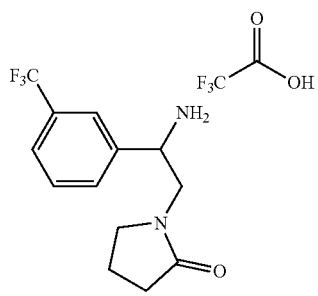

To a solution of tert-butyl N-[2-(2-oxopyrrolidin-1-yl)-1-[3-(trifluoromethyl)phenyl]ethyl]carbamate (from step 2)

(0.55 g, 1.47 mmol) in dichloromethane (15 mL), was added trifluoroacetic acid (1.13 mL, 14.7 mmol) and stirred at room temperature for 16 h. The reaction mass was concentrated to afford (550 mg) as an off-white gum, which was purified by preparative HPLC to afford 1-{2-amino-2-[3-(trifluoromethyl)phenyl]ethyl}pyrrolidin-2-one; trifluoroacetic acid (0.3 g) as a white solid.

¹H NMR (400 MHz, DMSO-d₆: D₂O) δ 7.93 (s, 1H), 7.79 (t, J=6.04 Hz, 2H), 7.67 (d, J=7.6 Hz, 1H), 4.65 (q, J=6.48 Hz, 1H), 3.73-3.69 (m, 1H), 3.51 (q, J=6.20 Hz, 1H), 3.28-3.21 (m, 2H), 2.09-2.17 (m, 2H), 1.91-1.83 (m, 2H);

MS: m/z 273.2 (M+1).

Step 4: Preparation of 1-{2-isothiocyanato-2-[3-(trifluoromethyl)phenyl]ethyl}pyrrolidin-2-one

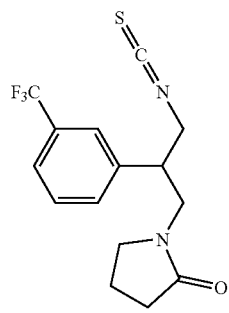 [SMILES: O=C1CCCN1CC(CN=C=S)c1cccc(C(F)(F)F)c1]

To a suspension of 1-{2-amino-2-[3-(trifluoromethyl)phenyl]ethyl}pyrrolidin-2-one; trifluoroacetic acid (from step 3) (0.3 g, 0.77 mmol) in dichloromethane (15 mL), cooled at 0° C., was added thiophosgene (0.18 ml, 2.3 g mmol) followed by 10% aqueous sodium bicarbonate solution (10 mL) and stirred at room temperature for 1 h. The reaction mixture was extracted with dichloromethane (2×0 mL). The combined organic extracts were dried over anhydrous sodium sulphate and concentrated to afford 1-{2-isothiocyanato-2-[3-(trifluoromethyl)phenyl]ethyl}pyrrolidin-2-one (0.24 g) as a reddish gum.

MS: m/z 315.2 (M+1).

Step 5: preparation of 1-(2-aminophenyl)-3-[2-(2-oxopyrrolidin-1-yl)-1-[3-(trifluoromethyl)phenyl]ethyl]thiourea

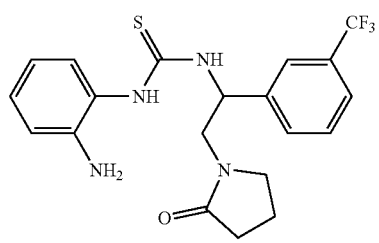 [SMILES: Nc1ccccc1NC(=S)NC(CN1CCCC1=O)c1cccc(C(F)(F)F)c1]

A mixture of 1-{2-isothiocyanato-2-[3-(trifluoromethyl)phenyl]ethyl}pyrrolidin-2-one (from step 4) (0.25 g, 0.79 mmol) and 1,2-phenylene diamine (86 mg, 0.79 mmol) in dichloromethane (60 ml) was stirred at room temperature for 12 h. The reaction mixture was concentrated to afford a crude product (350 mg) as a brownish gum, which was purified by silica gel (230-400 mesh) column chromatography eluting with 8% methanol in chloroform to afford 1-(2-aminophenyl)-3-[2-(2-oxopyrrolidin-1-yl)-1-[3-(trifluoromethyl)phenyl]ethyl]thiourea (300 mg) as a brownish gum.

MS: m/z 423.2 (M+1).

Example 11, Step 6: Preparation of 1-{2-[(1H-1,3-benzodiazol-2-yl)amino]-2-[3-(trifluoromethyl)phenyl]ethyl}pyrrolidin-2-one

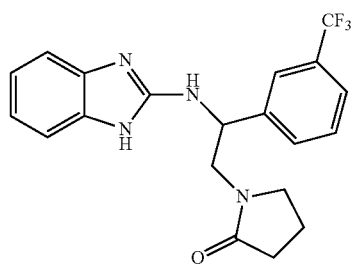 [SMILES: O=C1CCCN1CC(Nc1nc2ccccc2[nH]1)c1cccc(C(F)(F)F)c1]

To a solution of 1-(2-aminophenyl)-3-[2-(2-oxopyrrolidin-1-yl)-1-[3-(trifluoromethyl)phenyl]ethyl]thiourea (from step 5) (300 mg, 0.71 mmol) in methanol (10 mL) was added iodoacetic acid (0.2 g, 1 mmol) and the mixture refluxed for 2.5 h. The reaction mixture was evaporated to afford the crude product (350 mg), which was purified by silica gel (230-400 mesh) column chromatography using 10% methanol in chloroform as eluent to afford 1-{2-[(1H-1,3-benzodiazol-2-yl)amino]-2-[3-(trifluoromethyl)phenyl]ethyl}pyrrolidin-2-one (103 mg, 37%) as an off-white solid.

¹H NMR (400 MHz, DMSO-d₆) δ 10.83 (s, 1H), 7.84 (s, 1H), 7.77 (d, J=7.20 Hz, 1H), 7.59 (q, J=7.60 Hz, 2H), 7.29 (d, J=8.80 Hz, 1H), 7.09 (d, J=8.40 Hz, 2H), 6.84 (q, J=8.40 Hz, 2H), 5.25 (d, J=6.40 Hz, 1H), 3.63-3.49 (m, 2H), 3.39-3.27 (m, 2H), 2.14-2.10 (m, 2H), 1.80 (t, J=7.60 Hz, 2H);

MS: m/z 389.2 (M+1).

Example 12: Preparation of N-[(2R)-2-[(1H-1,3-benzodiazol-2-yl)amino]-2-[3-(trifluoromethyl)phenyl]ethyl]-2-methoxyacetamide

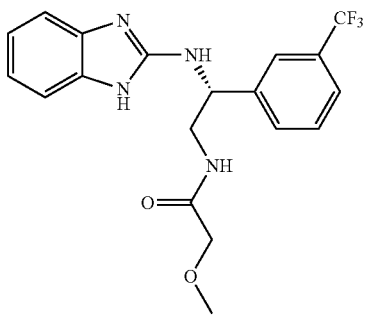 [SMILES: COCC(=O)NC[C@H](Nc1nc2ccccc2[nH]1)c1cccc(C(F)(F)F)c1]

Step 1: Preparation of (2R)-2-{[(tert-butoxy)carbonyl]amino}-2-[3-(trifluoromethyl)phenyl]acetic acid

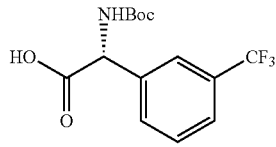 [SMILES: CC(C)(C)OC(=O)N[C@@H](C(=O)O)c1cccc(C(F)(F)F)c1]

To a solution of (2R)-2-amino-2-[3-(trifluoromethyl)phenyl]acetic acid (commercially available) (100 g, 456 mmol) in tert-butanol was added aqueous 2N sodium hydroxide solution (456 mL, 913 mmol). BOC anhydride was then added (129.4 mL, 593 mmol) and the reaction mixture was stirred at room temperature for 40 hrs. The reaction mass was concentrated under reduced pressure to remove the solvent t-butanol, the residue was acidified (pH=2) using a saturated aqueous solution of citric acid. The aqueous layer was extracted with ethyl acetate (2×250 mL). The combined organic layer was dried over sodium sulphate, filtered and concentrated to afford (2R)-2-{[(tert-butoxy)carbonyl]amino}-2-[3-(trifluoromethyl)phenyl]acetic acid (140 g) as an off-white solid.

MS: m/z 318.2 (M−1).

Step 2: Preparation of tert-butyl N-[(1R)-2-hydroxy-1-[3-(trifluoromethyl)phenyl]ethyl] carbamate

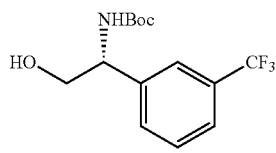

To a stirred solution of (2R)-2-{[(tert-butoxy)carbonyl]amino}-2-[3-(trifluoromethyl)phenyl]acetic acid (142 g, 445.1 mmol) (from Example 12, step 1) in THF (2400 mL), was added trimethylamine (81.26 mL, 578 mmol) followed by isobutyl chloroformate (63.63 mL, d=1.05 g/mL, 489 mmol) at 0° C. and stirred at same temperature for 6 h. The solid was formed in the reaction mass was filtered at 0° C. and the residue was washed with THF, the filtrate was added to a cooled mixture of NaBH$_4$ (33.65 g, 890 mmol) in water (100 mL). Then the reaction mass was stirred for 48 h. The reaction mixture was quenched with ice cold water (100 mL) and extracted with ethyl acetate (2×150 mL). The combined organic layer was washed with brine, dried over sodium sulphate, filtered and concentrated to afford yellowish liquid, which was purified by silica gel (60-120 mesh) column chromatography using 25% ethyl acetate in hexane to afford tert-butyl N-[(1R)-2-hydroxy-1-[3-(trifluoromethyl)phenyl]ethyl]carbamate (88.0 g) as off-white solid.

MS: m/z 206.2 (M+1, loss of Boc)

Step 3: Preparation of (tert-butyl N-[(1R)-2-(methanesulfonyloxy)-1-[3-(trifluoromethyl)phenyl]ethyl] carbamate

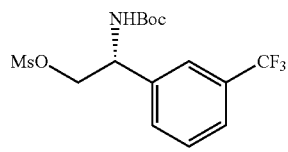 [SMILES: CC(C)(C)OC(=O)N[C@@H](COS(C)(=O)=O)c1cccc(C(F)(F)F)c1]

To a solution of tert-butyl N-[(1R)-2-hydroxy-1-[3-(trifluoromethyl)phenyl]ethyl]carbamate (from Example 12, step 2) (6.75 g, 22.10 mmol) in dichloromethane (70 mL), was added TEA (9.31 mL, 66.32 mmol) at 0° C., followed by mesylchloride (3.04 g, 26.53 mmol). The reaction mixture was allowed to attain RT and stirred to 2 h. The reaction mixture was diluted with water (50 mL) and extracted with DCM (2×50 mL) and evaporated to afford the product tert-butyl N-[(1R)-2-(methanesulfonyloxy)-1-[3-(trifluoromethyl)phenyl]ethyl]carbamate (6.20 g) as a brown liquid, used in the next step without further purification.

$^1$H NMR (400 MHz, DMSO-d$_6$) δ 7.80-7.59 (m, 5H), 5.01 (d, 1H, J=5.2 Hz), 4.33-4.24 (m, 2H), 3.18 (s, 3H), 1.37 (s, 9H);

MS: m/z 284.2 [(M+1)-Boc].

Step 4: Preparation of tert-butyl N-[(1R)-2-azido-1-[3-(trifluoromethyl)phenyl]ethyl] carbamate

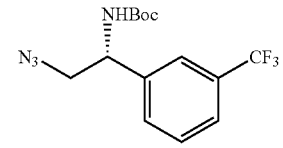 [SMILES: CC(C)(C)OC(=O)N[C@@H](CN=[N+]=[N-])c1cccc(C(F)(F)F)c1]

To a solution of tert-butyl N-[(1R)-2-(methanesulfonyloxy)-1-[3-(trifluoromethyl)phenyl]ethyl]carbamate (from Example 12, step 3) (9.0 g, 23.47 mmol) in DMF (90 mL), sodium azide (6.10 g, 93.90 mmol) was added at 0° C. and stirred for 12 h at 80° C. The reaction mixture was allowed to cool to ambient temperature and ice water (200 mL) was added. The reaction mixture was extracted with EtOAc (2×500 mL), dried over sodium sulphate and concentrated to afford a crude material as yellow colour solid, which was purified by column chromatography using 25% ethyl acetate in petroleum ether, as eluent, to afford tert-butyl N-[(1R)-2-azido-1-[3-(trifluoromethyl)phenyl]ethyl]carbamate (6.10 g) as a pale yellow solid.

$^1$H NMR (400 MHz, DMSO-d$_6$) δ 7.80-7.77 (m, 2H), 7.68-7.57 (m, 3H), 4.86 (br.s, 1H), 3.51 (d, 2H, J=7.88 Hz), 1.39 (s, 9H);

IR (Neat): 2099.6 cm$^{-1}$

Step 5: Preparation of tert-butyl N-[(1R)-2-amino-1-[3-(trifluoromethyl)phenyl]ethyl] carbamate

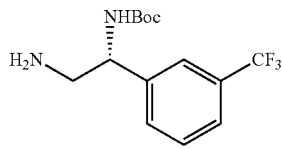

To a stirred solution of tert-butyl N-[(1R)-2-azido-1-[3-(trifluoromethyl)phenyl]ethyl]carbamate (from Example 12, step 4) (5.9 g, 17.86 mmol) in methanol (60 mL) was added Pd/C (1.90 g) (20% w/w) under an inert atmosphere. The mixture was then hydrogenated (under a balloon pressure) at ambient temperature for 12 h. Reaction mass was filtered through a celite bed and the residue was washed with methanol (3×100 mL). The combined filtrate was concentrated to afford tert-butyl N-[(1R)-2-amino-1-[3-(trifluoromethyl)phenyl]ethyl]carbamate (4.2 g) as brown liquid.

$^1$H NMR (400 MHz, DMSO-$d_6$) δ 7.59-7.43 (m, 4H), 7.44 (d, 1H, J=7.6 Hz), 4.49 (br.s, 0.5H), 4.09 (br.s, 0.5H), 3.17 (s, 2H), 2.70 (d, 2H, J=6.4 Hz), 1.36 (s, 9H);

MS: m/z 305.2 (M+1).

Step 6: Preparation of tert-butyl N-[(1R)-2-(2-methoxyacetamido)-1-[3-(trifluoromethyl)phenyl]ethyl]carbamate

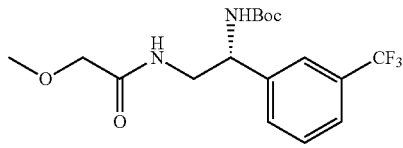 [SMILES: COCC(=O)NC[C@H](NC(=O)OC(C)(C)C)c1cccc(C(F)(F)F)c1]

To a solution of tert-butyl N-[(1R)-2-amino-1-[3-(trifluoromethyl)phenyl]ethyl]carbamate (from Example 12, step 5) (1.8 g, 5.91 mmol) and trimethylamine (2.49 mL, 17.74 mmol) in DCM (20 mL), 2-methoxyacetyl chloride (0.77 g, 7.09 mmol) was added drop wise at 0° C. and stirred for 2 h at RT. The reaction mixture was diluted with water (50 mL), extracted with DCM (2×50 mL), dried over sodium sulphate and evaporated to afford crude material which was purified by column chromatography with silica gel 60-120 mesh eluting with 2% MeOH in DCM to afford tert-butyl N-[(1R)-2-(2-methoxyacetamido)-1-[3-(trifluoromethyl)phenyl]ethyl]carbamate (1.6 g) as an off white solid.

$^1$H NMR (400 MHz, DMSO-$d_6$) δ 7.88 (s, 1H), 7.61-7.56 (m, 5H), 4.79 (q, 1H, J=6.68 Hz), 3.72 (s. 2H), 3.44-3.35 (m, 1H), 3.34-3.27 (m, 1H), 3.22 (s, 3H), 1.36 (s, 9H);

MS: m/z 277.2 [(M+1)-Boc].

Step 7: Preparation of N-[(2R)-2-amino-2-[3-(trifluoromethyl)phenyl]ethyl]-2-methoxyacetamide; trifluoroacetic acid

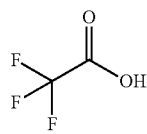

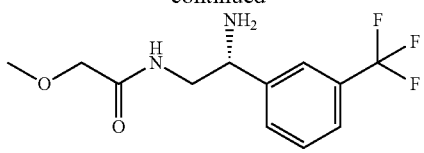

To a solution of tert-butyl N-[(1R)-2-(2-methoxyacetamido)-1-[3-(trifluoromethyl)phenyl]ethyl]carbamate (from Example 12, step 6) (0.5 g, 1.33 mmol) in DCM (5 mL), was added TFA (0.406 mL, d=1.49 g/mL, 5.31 mmol) at 0° C. and the reaction mass was slowly warmed to ambient temperature and stirred for 16 h. The reaction mass was evaporated to dryness to afford (N-[(2R)-2-amino-2-[3-(trifluoromethyl)phenyl]ethyl]-2-methoxyacetamide; trifluoroacetic acid (0.35 g) as a pale brown solid.

$^1$H NMR (400 MHz, DMSO-$d_6$) δ 8.50 (s, 3H), 8.03 (t, 1H, J=6.0 Hz), 7.87 (s, 1H), 7.77 (q, 2H, J=7.6 Hz), 7.69 (t, 1H, J=7.6 Hz), 4.56 (q, 1H, J=6.0 Hz), 3.76 (d, 2H, J=7.2 Hz), 3.67-3.62 (m, 1H), 3.59-3.54 (m, 1H), 3.22 (s, 3H);

MS: m/z 277.2 (M+1).

Step 8: Preparation of N-[(2R)-2-isothiocyanato-2-[3-(trifluoromethyl)phenyl]ethyl]-2-methoxyacetamide

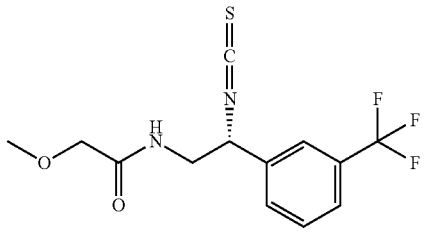 [SMILES: COCC(=O)NC[C@H](N=C=S)c1cccc(C(F)(F)F)c1]

To a suspension of N-[(2R)-2-amino-2-[3-(trifluoromethyl)phenyl]ethyl]-2-methoxyacetamide; trifluoroacetic acid (from Example 12, step 7) (1.8 g, 4.82 mmol) in dichloromethane (10 mL) cooled at 0° C. was added thiophosgene (1.11 mL, d=1.5 g/mL, 14.46 mmol) followed by 10% aqueous sodium bicarbonate solution (10 mL). The reaction mixture was then stirred at ambient temperature for 1 h, the reaction mixture was diluted with 10% aqueous sodium bicarbonate solution (10 mL) and extracted with dichloromethane (3×25 mL). The combined organic extracts were dried over anhydrous sodium sulphate and evaporated to afford N-[(2R)-2-isothiocyanato-2-[3-(trifluoromethyl)phenyl]ethyl]-2-methoxyacetamide (1.2 g) as a red gum.

$^1$H NMR (400 MHz, CDCl$_3$) δ 7.66-7.57 (m, 4H), 6.99 (s, 1H), 4.84 (br.s, 1H), 3.96 (s, 2H), 3.87-3.80 (m, 1H), 3.54-3.45 (m, 1H), 3.45 (s, 3H);

MS: m/z 319.2 (M+1).

Step 9: Preparation of N-[(2R)-2-{[(2-aminophenyl)carbamothioyl]amino}-2-[3-(trifluoromethyl)phenyl]ethyl]-2-methoxyacetamide

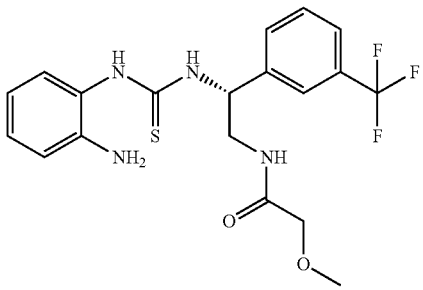 [SMILES: COCC(=O)NC[C@H](NC(=S)Nc1ccccc1N)c1cccc(C(F)(F)F)c1]

A mixture of N-[(2R)-2-isothiocyanato-2-[3-(trifluoromethyl)phenyl]ethyl]-2-methoxyacetamide (form Example 12, step 8) (0.35 g, 1.09 mmol) and 1, 2-phenylene diamine (0.119 g, 1.09 mmol) in dichloromethane (5 mL) was stirred at ambient temperature for 12 h. The reaction mixture was concentrated to afford a crude product (0.5 g) as a brownish gum, which was purified by silica gel (60-120 mesh) column chromatography eluting with 3% methanol in chloroform to afford N-[(2R)-2-{[(2-aminophenyl)carbamothioyl]amino}-2-[3-(trifluoromethyl)phenyl]ethyl]-2-methoxyacetamide (0.22 g) as a brown solid.

$^1$H NMR (400 MHz, DMSO-d$_6$) δ 8.96 (s, 1H), 7.92 (br.s, 2H), 7.64-7.56 (m, 5H), 6.98 (t, 2H, J=7.6 Hz), 6.75 (d, 1H, J=7.6 Hz), 6.57 (t, 1H, J=7.6 Hz), 5.70 (br.s, 1H), 4.81 (br.s, 1H), 3.75-3.74 (m, 2H), 3.55-3.40 (m, 2H), 3.24 (s, 3H);

MS: m/z 427.2 (M+1).

Example 12, Step 10: N-[(2R)-2-[(1H-1,3-benzodiazol-2-yl)amino]-2-[3-(trifluoromethyl)phenyl]ethyl]-2-methoxyacetamide

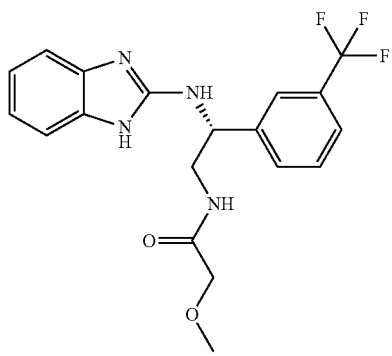 [SMILES: COCC(=O)NC[C@H](Nc1nc2ccccc2[nH]1)c1cccc(C(F)(F)F)c1]

To a solution of N-[(2R)-2-{[(2-aminophenyl)carbamothioyl]amino}-2-[3-(trifluoromethyl)phenyl]ethyl]-2-methoxyacetamide (0.22 g, 0.515 mmol) (from Example 12, step 9) in methanol (4 mL) was added iodoacetic acid (0.096 g, 0.515 mmol) and the mixture was refluxed for 2 h. The reaction mixture was evaporated to afford the crude product (0.4 g) which was purified by silica gel (60-120 mesh) column chromatography using 4% methanol in chloroform as eluent to afford N-[(2R)-2-[(1H-1,3-benzodiazol-2-yl)amino]-2-[3-(trifluoromethyl)phenyl]ethyl]-2-methoxyacetamide (0.125 g) as an off-white solid.

$^1$H NMR (400 MHz, DMSO-d$_6$) δ 10.86 (s, 1H), 8.02 (t, 1H, J=5.6 Hz), 7.76-7.70 (m, 2H), 7.60-7.54 (m, 2H), 7.30 (br.s, 1H), 7.09 (d, 2H, J=7.2 Hz), 6.88-6.81 (m, 2H), 5.15 (q, 1H, J=7.2 Hz), 3.74 (s, 2H), 3.52 (t, 2H, J=6.4 Hz), 3.19 (s, 3H);

MS: m/z 393.2 (M+1).

Example 13: Preparation of N-[(2R)-2-[(1H-1,3-benzodiazol-2-yl)amino]-2-[3-(trifluoromethyl)phenyl]ethyl]-2-hydroxyacetamide

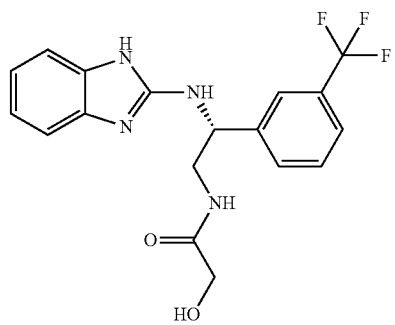 [SMILES: O=C(CO)NC[C@H](Nc1nc2ccccc2[nH]1)c1cccc(C(F)(F)F)c1]

Step 1: Preparation of tert-butyl N-[(1R)-2-(2-hydroxyacetamido)-1-[3-(trifluoromethyl)phenyl]ethyl]carbamate

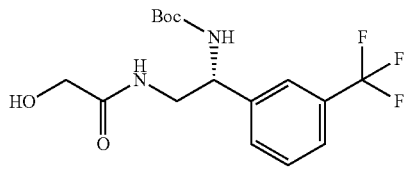 [SMILES: CC(C)(C)OC(=O)N[C@@H](CNC(=O)CO)c1cccc(C(F)(F)F)c1]

To a solution of 2-hydroxyacetic acid (0.375 g, 4.92 mmol), TEA (0.998 g, 9.85 mmol) in DMF (10 ml), BOP reagent (2.18 g, 4.92 mmol) was added, followed by the addition of tert-butyl N-[(1R)-2-amino-1-[3-(trifluoromethyl)phenyl]ethyl]carbamate (from Example 12, Step 5) (1 g, 3.28 mmol), and the reaction mixture was stirred at ambient temperature for 12 h. The reaction mass was concentrated, dissolved in ethyl acetate (50 ml) and washed with water (10 ml), dried over anhydrous sodium sulphate, filtered and concentrated to afford crude product (1.2 g) as brown gummy material, which was purified by silica gel (60-120 mesh) column chromatography eluting with 7% methanol in chloroform to afford N-[(2R)-2-amino-2-[3-(trifluoromethyl)phenyl]ethyl]-2-hydroxyacetamide; trifluoroacetic acid (0.55 g) as white gum.

$^1$H NMR (400 MHz, DMSO-de, D$_2$O) δ 7.56 (t, 4H, J=4.36 Hz), 4.69 (t, 1H, J=6.32 Hz), 3.74 (s, 2H), 3.41 (dd, 1H, J=6.00, 12.92 Hz), 3.26 (dd, 1H, J=8.60, 13.50 Hz), 1.36 (s, 9H);

MS: m/z 263.2 [(M+1)-Boc].

Step 2: Preparation of N-[(2R)-2-amino-2-[3-(trifluoromethyl)phenyl]ethyl]-2-hydroxyacetamide; trifluoroacetic acid

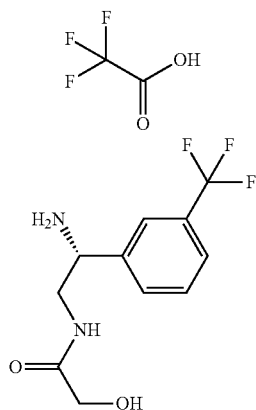

To a cooled (0° C.) solution of N-[(2R)-2-amino-2-[3-(trifluoromethyl)phenyl]ethyl]-2-hydroxyacetamide; trifluoroacetic acid (from step 1) (0.55 g, 1.5 mmol) in dichloromethane (10 ml), TFA (0.17 g, 1.5 mmol) was added, and the reaction was stirred at ambient temperature for 16 h. The reaction mass was concentrated to afford N-[(2R)-2-amino-2-[3-(trifluoromethyl)phenyl]ethyl]-2-hydroxyacetamide; trifluoroacetic acid (0.55 g) as a brown gum.

$^1$H NMR (400 MHz, DMSO-$d_6$) δ 8.45 (bs, 4H,$D_2O$ exchange), 7.87 (s, 1H), 7.78-7.66 (m, 3H), 4.55 (t, 1H, J=6.00 Hz), 3.78 (d, 2H, J=3.60 Hz), 3.67-3.62 (m, 1H), 3.56-3.52 (m, 1H);

MS: m/z 263.2 (M+1).

Step 3: Preparation of 2-hydroxy-N-[(2R)-2-isothiocyanato-2-[3-(trifluoromethyl)phenyl]ethyl]acetamide

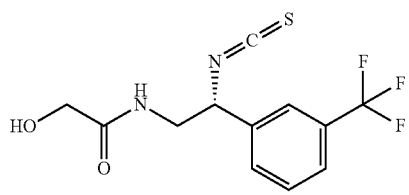 [SMILES: O=C(CO)NC[C@H](N=C=S)c1cccc(C(F)(F)F)c1]

To a stirred solution of N-[(2R)-2-amino-2-[3-(trifluoromethyl)phenyl]ethyl]-2-hydroxyacetamide; trifluoroacetic acid (from step 2) (0.35 g, 0.93 mmol) and thiophosgene (0.46 g, 2.79 mmol) in dichloromethane (10 ml) was added a saturated solution of sodium bicarbonate (10 ml) and the reaction mixture was stirred at 0° C. for an hour. The reaction mixture was slowly warmed to room temperature and stirred for 4 h. It was diluted with dichloromethane (20 ml) and the organic phase was separated. The aqueous phase was extracted with dichloromethane (25 ml). The combined organic phase was dried over anhydrous sodium sulphate, filtered and concentrated under reduced pressure to afford 2-hydroxy-N-[(2R)-2-isothiocyanato-2-[3-(trifluoromethyl)phenyl]ethyl]acetamide (0.38 g) as a yellow liquid.

$^1$H NMR (400 MHz, DMSO-$d_6$) δ 8.16 (br.s, 1H, $D_2O$ exchange), 7.78-7.69 (m, 4H), 5.76 (s, 1H), 5.42 (q, 1H, J=4.80 Hz), 3.82 (s, 2H), 3.69-3.64 (m, 1H), 3.52-3.50 (m, 1H).

Step 4: Preparation of N-[(2R)-2-{[(2-aminophenyl)carbamothioyl]amino}-2-[3-(trifluoromethyl)phenyl]ethyl]-2-hydroxyacetamide

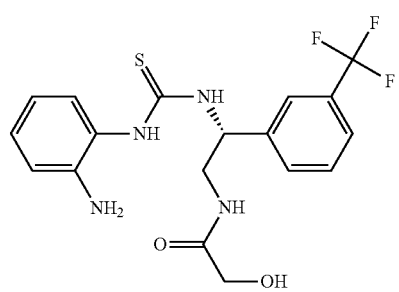 [SMILES: Nc1ccccc1NC(=S)N[C@@H](CNC(=O)CO)c1cccc(C(F)(F)F)c1]

To a solution of 2-hydroxy-N-[(2R)-2-isothiocyanato-2-[3-(trifluoromethyl)phenyl]ethyl]acetamide (from step 3) (0.35 g, 1.15 mmol) in dichloromethane (10 ml), benzene-1,2-diamine (0.124 g, 1.15 mmol) was added, and the reaction mixture was stirred at ambient temperature for 16 h. The reaction mixture was concentrated and triturated with hexane (5 ml) to afford N-[(2R)-2-{[(2-aminophenyl)carbamothioyl]amino}-2-[3-(trifluoromethyl)phenyl]ethyl]-2-hydroxyacetamide (0.35 g, 73%) as brown gum.

MS: m/z 412.7 (M+1).

Example 13, Step 5: Preparation of N-[(2R)-2-[(1H-1,3-benzodiazol-2-yl)amino]-2-[3-(trifluoromethyl)phenyl]ethyl]-2-hydroxyacetamide

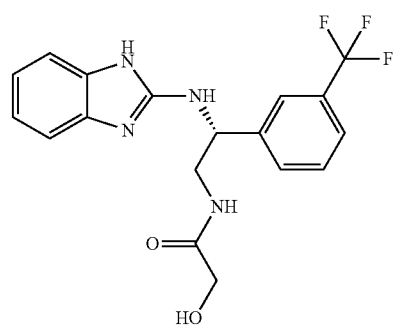 [SMILES: O=C(CO)NC[C@H](Nc1nc2ccccc2[nH]1)c1cccc(C(F)(F)F)c1]

To a solution of N-[(2R)-2-{[(2-aminophenyl)carbamothioyl]amino}-2-[3-(trifluoromethyl)phenyl]ethyl]-2-hydroxyacetamide (from step 4) (0.35 g, 0.85 mmol) in methanol (10 ml), iodo acetic acid (0.158 g, 0.85 mmol) was added, and the reaction was refluxed for 4 h. The reaction mixture was concentrated and purified by silica gel (60-120 mesh) column chromatography using 3% methanol in chloroform as eluent to afford a the product as the HI salt. This was dissolved in ethyl acetate and washed with 10% NaOH solution and the organic layer was evaporated to dryness to afford N-[(2R)-2-[(1H-1,3-benzodiazol-2-yl)amino]-2-[3-(trifluoromethyl)phenyl]ethyl]-2-hydroxyacetamide (0.09 g) as a white solid.

$^1$H NMR (400 MHz, DMSO-de, D$_2$O) 7.78 (s, 1H), 7.73 (d, 1H, J=7.20 Hz), 7.63-7.56 (m, 2H), 7.14-7.11 (m, 2H), 6.90-6.88 (m, 2H), 5.11 (q, 1H, J=8.00 Hz), 3.78 (d, 2H, J=4.00 Hz), 3.57-3.47 (m, 2H);

MS: m/z 379.2 (M+1).

Example 14: Preparation of N-{3-[(1H-1,3-benzodiazol-2-yl)amino]-3-[3-(trifluoromethyl)phenyl]propyl}acetamide

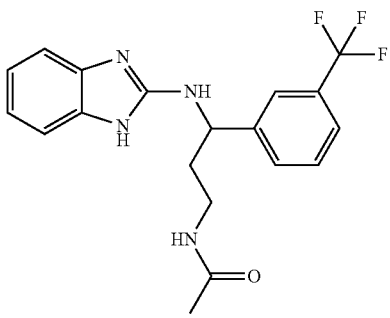 [SMILES: CC(=O)NCCC(Nc1nc2ccccc2[nH]1)c1cccc(C(F)(F)F)c1]

Step 1: Preparation of 3-amino-3-[3-(trifluoromethyl)phenyl]propanoic acid

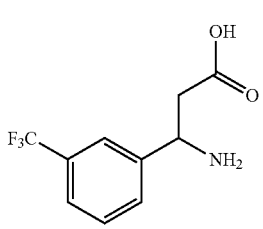 [SMILES: NC(CC(=O)O)c1cccc(C(F)(F)F)c1]

A mixture of malonic acid (298.82 g, 2872 mmol), ammonium formate (362.14 g, 5743 mmol) and 3-(trifluoromethyl)benzaldehyde (commercially available) (500 g, 2873 mmol) in ethanol (1000 mL) was refluxed for 12 h. The reaction mixture was evaporated to remove ethanol and the residue was triturated with acetone (2500 mL). The solid was filtered and dried to afford 3-amino-3-[3-(trifluoromethyl)phenyl]propanoic acid (255 g) as a white solid.

$^1$H NMR (400 MHz, AcOH-d$_4$) δ 7.87-7.81 (m, 2H), 7.74 (d, 1H, J=7.6 Hz), 7.66-7.62 (m, 1H), 4.98 (br. S, 1H), 3.36 (dd, 1H, J=16.0, 8.0 Hz), 3.13 (dd, 1H, J=17.6, 5.6 Hz);

MS: m/z 234 (M+1).

Step 2: Preparation of 3-{[(tert-butoxy)carbonyl]amino}-3-[3-(trifluoromethyl)phenyl] propanoic acid

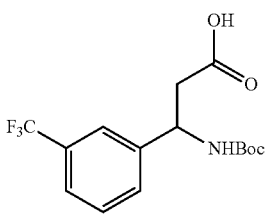 [SMILES: CC(C)(C)OC(=O)NC(CC(=O)O)c1cccc(C(F)(F)F)c1]

To a suspension of 3-amino-3-[3-(trifluoromethyl)phenyl]propanoic acid (from Step 1) (500 g, 2144 mmol) in t-BuOH (2500 mL) cooled to 0° C. was added NaOH (171.52 g, 4288 mmol) dissolved in water (1250 mL). The mixture was stirred for 10 min and Boc anhydride (561.56 g, 2573 mmol) was added drop wise and the mixture was then warmed to ambient temperature and stirred it for 18 h. The reaction was diluted with water and the mixture pH was adjusted up to 6 with citric acid and extracted with ethyl acetate (3×1000 mL). The combined organic extracts were dried over anhydrous sodium sulphate and evaporated to afford 3-{[(tert-butoxy)carbonyl]amino}-3-[3-(trifluoromethyl)phenyl]propanoic acid (595 g) as a colourless gum.

$^1$H NMR (300 MHz, DMSO-d$_6$) δ 7.78 (br.s, 1H), 7.63-7.54 (m, 3H), 6.14 (br.s, 1H), 4.90 (br.S, 1H), 2.50 (s, 2H), 1.35 (s, 9H);

MS: m/z 332 ((M−1)).

Step 3: Preparation of tert-butyl N-{3-hydroxy-1-[3-(trifluoromethyl)phenyl]propyl} carbamate

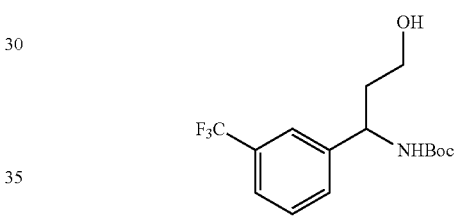

To a suspension of 3-{[(tert-butoxy)carbonyl]amino}-3-[3-(trifluoromethyl)phenyl]propanoic acid (from step 2) (50 g, 150.01 mmol) in THF (150 mL) was added TEA (24.61 mL, d=0.72 g/mL, 180.01 mmol) and isobutyl chloroformate (19.51 mL, d=1.05 g/mL, 150.01 mmol) at 0° C. and stirred at 0° C. temperature for 4 h. Solid formed was filter off at 0° C. and the residue was washed with THF (50 mL). The combined filtrate was added to a cooled mixture of NaBH$_4$ (14.19 g, 375.02 mmol) in water (100 mL). Then the reaction mass was slowly warmed to RT and stirred for 30 h. The reaction mixture was quenched with ice cold water (500 mL) and extracted with ethylacetate (2×500 mL). The combined organic layer was washed with brine, dried over Na$_2$SO$_4$, filtered and concentrated to afford a yellowish liquid (41 g) which was purified by column chromatography by using 35% ethyl acetate in petroleum ether as eluent to afford tert-butyl N-{3-hydroxy-1-[3-(trifluoromethyl)phenyl]propyl}carbamate (28.0 g) as a pale yellow liquid.

$^1$H NMR (400 MHz, DMSO-d$_6$) δ 7.63-7.50 (m, 5H), 4.70 (d, 1H, J=6.8 Hz), 4.56 (s, 1H), 3.40-3.31 (m, 1H), 3.28 (t, 1H, J=5.2 Hz), 1.83 (dd, 1H, J=12.0, 6.0 Hz), 1.72 (dd, 1H, J=12.8, 6.4 Hz), 1.38 (s, 9H);

MS: m/z 220.1 [(M+1)-Boc].

Step 4: Preparation of tert-butyl N-[3-(methanesulfonyloxy)-1-[3-(trifluoromethyl)phenyl]propyl] carbamate

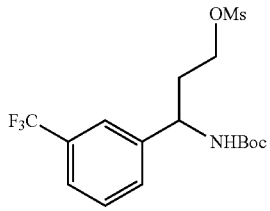 [SMILES: CC(C)(C)OC(=O)NC(CCOS(C)(=O)=O)c1cccc(C(F)(F)F)c1]

To a solution of tert-butyl N-{3-hydroxy-1-[3-(trifluoromethyl)phenyl]propyl}carbamate (from step 3) (100 g, 313.16 mmol) in dichloromethane (1000 mL), was added TEA (132.04 mL, 939.49 mmol) at 0° C., followed by mesyl chloride (31.50 mL, d=1.48 g/mL, 407.11 mmol). The reaction mixture was allowed to attain RT and stirred for 2 h. The mixture was diluted with water (500 mL) and extracted with dichloromethane (2×500 mL). The combined organic layer was washed with brine, dried over $Na_2SO_4$, filtered and concentrated to afford tert-butyl N-[3-(methanesulfonyloxy)-1-[3-(trifluoromethyl)phenyl]propyl]carbamate (112 g) as brown liquid, which was used in the next step without further purification.

$^1$H NMR (400 MHz, DMSO-$d_6$) δ 7.68-7.57 (m, 5H), 4.73 (q, 1H, J=8.48 Hz), 4.25 (dd, 1H, J=9.88, 6.92 Hz), 4.14 (dd, 1H, J=11.0, 5.72 Hz), 3.16 (s, 3H), 2.07 (q, 2H, J=5.76 Hz), 1.35 (s, 9H);

MS: m/z 298.0 [(M+1)-Boc].

Step 5: Preparation of tert-butyl N-{3-azido-1-[3-(trifluoromethyl)phenyl]propyl} carbamate

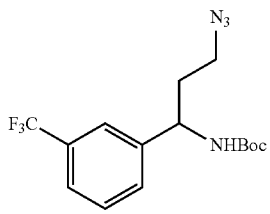 [SMILES: CC(C)(C)OC(=O)NC(CCN=[N+]=[N-])c1cccc(C(F)(F)F)c1]

To a solution of tert-butyl N-[3-(methanesulfonyloxy)-1-[3-(trifluoromethyl)phenyl]propyl]carbamate (from step 4) (105 g, 264.21 mmol) in DMF (1000 mL), sodium azide (68.69 g, 1056.8 mmol) was added at 0° C. and stirred for 12 h at 80° C. The reaction mixture was allowed to cool to ambient temperature, ice water (1000 mL) was added and the reaction mixture was extracted with EtOAc (2×500 mL), dried over sodium sulphate and concentrated to afford crude material as a yellow solid. This was purified by column chromatography by using 25% ethyl acetate in petroleum ether as eluent to afford the product tert-butyl N-{3-azido-1-[3-(trifluoromethyl)phenyl]propyl}carbamate (59 g) as a pale yellow solid.

$^1$H NMR (400 MHz, CDCl$_3$) δ 7.57-7.49 (m, 4H), 5.02 (br.s, 1H), 4.86 (br.s, 1H), 3.37 (q, 2H, J=6.4 Hz), 2.06-2.02 (m, 2H), 1.44 (s, 9H);

MS: m/z 245.1 [(M+1)-Boc];

IR (Neat): 2096.5 cm$^{-1}$

Step 6: Preparation of tert-butyl N-{3-amino-1-[3-(trifluoromethyl)phenyl]propyl} carbamate

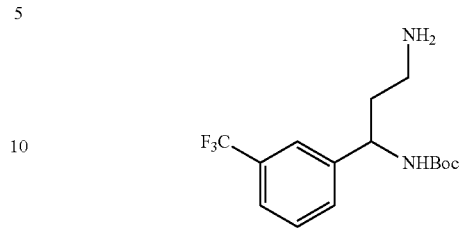

To a stirred solution of tert-butyl N-{3-azido-1-[3-(trifluoromethyl)phenyl]propyl}carbamate (from step 5) (60 g, 174.24 mmol) in methanol (600 mL) was added Pd/C (14.83 g) (20% w/w) under an inert atmosphere. The mixture was hydrogenated (under balloon pressure) at ambient temperature for 12 h. Reaction mass was filtered through a celite bed, the residue was washed with methanol (3×150 mL). The combined filtrate was concentrated to afford tert-butyl N-{3-amino-1-[3-(trifluoromethyl)phenyl]propyl}carbamate (48 g) as a brown liquid.

$^1$H NMR (400 MHz, DMSO-$d_6$) 7.66-7.55 (m, 5H), 4.71 (br.s, 1H), 3.50 (br.s, 2H), 2.51-2.47 (m, 2H), 1.73 (dd, 1H, J=13.76, 7.44 Hz), 1.66 (dd, 1H, J=14.08, 7.88 Hz), 1.36 (s, 9H);

MS: m/z 319.2 (M+1).

Step 7: Preparation of tert-butyl N-{3-acetamido-1-[3-(trifluoromethyl)phenyl]propyl} carbamate

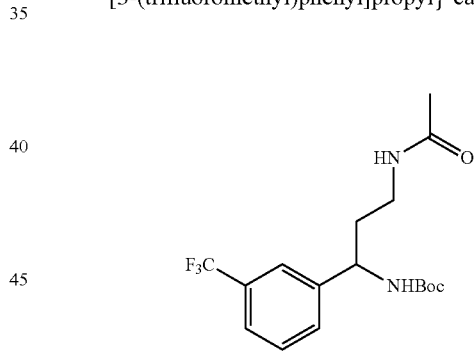

To a mixture of tert-butyl N-{3-amino-1-[3-(trifluoromethyl)phenyl]propyl}carbamate (from step 6) (70 g, 219.89 mmol) and trimethylamine (92.65 mL, d=0.72 g/mL, 659.67 mmol) in DCM (700 mL), acetic anhydride (25.98 mL, d=1.08 g/mL, 274.86 mmol) was added drop wise at 0° C. and stirred for 2 h at RT. The reaction mixture was diluted with water (250 mL), extracted with DCM (2×250 mL), dried over sodium sulphate and evaporated to dryness to afford a crude product. This was purified by column chromatography on silica gel (60-120 mesh) eluting with 2.5% MeOH in DCM to afford tert-butyl N-{3-acetamido-1-[3-(trifluoromethyl)phenyl]propyl}carbamate (55.00 g) as an off white solid.

$^1$H NMR (300 MHz, DMSO-$d_6$) 7.66-7.58 (m, 5H), 7.82 (br.s, 1H), 4.61 (d, 1H, J=7.5 Hz), 3.33-3.23 (m, 2H), 2.97 (t, 2H, J=5.7 Hz), 1.78 (s, 3H), 1.36 (s, 9H);

MS: m/z 260.8 [(M+1)-Boc]

Step 8: Preparation of N-{3-amino-3-[3-(trifluoromethyl)phenyl]propyl}acetamide; trifluoroacetic acid

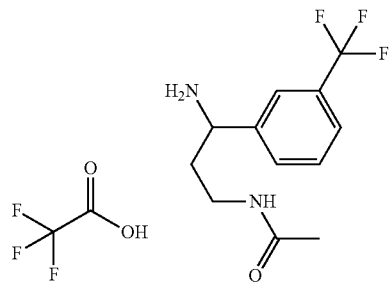 [SMILES: O=C(O)C(F)(F)F ; CC(=O)NCCC(N)c1cccc(C(F)(F)F)c1]

To a solution of tert-butyl N-{3-acetamido-1-[3-(trifluoromethyl)phenyl]propyl}carbamate (from step 7) (60.0 g, 166.49 mmol) in DCM (600 mL), was added TFA (105.47 mL, d=1.49 g/mL, 665.96 mmol) at 0° C., and then the reaction mass was slowly warmed to ambient temperature and stirred for 16 h. The reaction mass was evaporated to dryness to afford N-{3-amino-3-[3-(trifluoromethyl)phenyl]propyl}acetamide; trifluoroacetic acid (55.0 g) as a pale brown solid.

MS: m/z 261.1 (M+1).

Step 9: Preparation of N-{3-isothiocyanato-3-[3-(trifluoromethyl)phenyl]propyl}acetamide

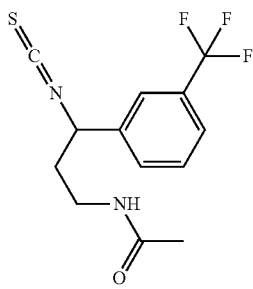 [SMILES: CC(=O)NCCC(N=C=S)c1cccc(C(F)(F)F)c1]

To a suspension of N-{3-amino-3-[3-(trifluoromethyl)phenyl]propyl}acetamide; trifluoroacetic acid (from step 8) (20.0 g, 55.97 mmol) in dichloromethane (200 mL) cooled at 0° C. was added thiophosgene (12.87 mL, d=1.5 g/mL, 167.93 mmol) followed by 10% aqueous sodium bicarbonate solution (100 mL). The reaction mixture was then stirred at ambient temperature. After 1 h, the reaction mixture was diluted with 10% aqueous sodium bicarbonate solution (100 mL) and extracted with dichloromethane (3×200 mL). The combined organic extracts were dried over anhydrous sodium sulphate and evaporated to dryness to afford of N-{3-isothiocyanato-3-[3-(trifluoromethyl)phenyl]propyl}acetamide (16.50 g) as a red gum.

$^1$H NMR (400 MHz, CDCl$_3$) δ 7.62-7.54 (m, 4H); 5.69 (br.s, 1H), 4.94 (t, 1H, J=4.0 Hz), 3.42 (t, 2H, J=6.0 Hz), 2.23-2.10 (m, 2H), 2.01 (s, 3H);

MS: m/z 303.0 (M+1).

Step 10: Preparation of N-(3-{[(2-aminophenyl)carbamothioyl]amino}-3-[3-(trifluoromethyl)phenyl]propyl)acetamide

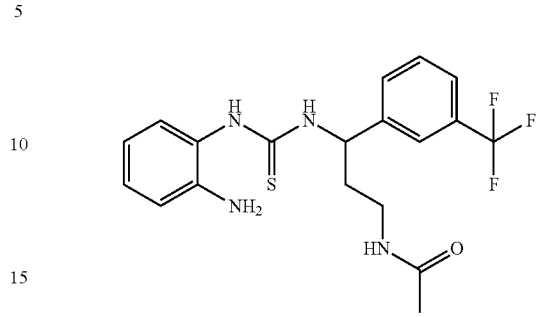

A mixture of N-{3-isothiocyanato-3-[3-(trifluoromethyl)phenyl]propyl}acetamide (from step 9) (16.50 g, 54.57 mmol) and 1,2-phenylene diamine (5.902 g, 54.57 mmol) in dichloromethane (1650 mL) was stirred at ambient temperature for 12 h. The reaction mixture was concentrated to afford a crude product (23 g) as a brownish gum, which was purified by silica gel (60-120 mesh) column chromatography with 3% methanol in chloroform as eluent, to afford N-(3-{[(2-aminophenyl)carbamothioyl]amino}-3-[3-(trifluoromethyl)phenyl]propyl)acetamide (16.0 g) as a brown solid.

$^1$H NMR (300 MHz, DMSO-d$_6$) δ 8.91-8.84 (m, 1H), 7.92-7.84 (m, 2H), 7.71-7.54 (m, 6H), 6.97 (t, 2H, J=7.5 Hz), 6.74 (d, 1H, J=7.8 Hz), 6.55 (t, 1H, J=7.2 Hz), 5.60 (br.s, 1H), 3.14-3.00 (m, 2H), 1.95-1.87 (m, 2H), 1.84 (s, 3H);

MS: m/z 411.0 (M+1).

Example 14, Step 11: Preparation of N-{3-[(1H-1,3-benzodiazol-2-yl)amino]-3-[3-(trifluoromethyl)phenyl]propyl}acetamide

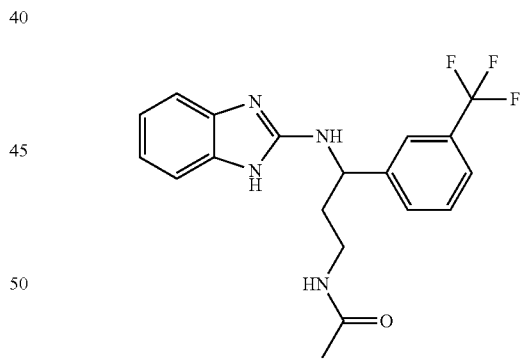

To a solution of N-(3-{[(2-aminophenyl)carbamothioyl]amino}-3-[3-(trifluoromethyl)phenyl]propyl)acetamide (from step 10) (11 g, 26.79 mmol) in methanol (110 mL) was added iodoacetic acid (4.98 g, 26.79 mmol) and the mixture was refluxed for 2 h. The reaction mixture was evaporated to afford the crude product (15.5 g) which was purified by silica gel (60-120 mesh) column chromatography using 4% methanol in chloroform as eluent to afford N-{3-[(1H-1,3-benzodiazol-2-yl)amino]-3-[3-(trifluoromethyl)phenyl]propyl}acetamide (6 g) as an off-white solid.

$^1$H NMR (400 MHz, DMSO-d$_6$) δ 10.71 (s, 1H), 7.92 (br.s, 1H), 7.81 (s, 1H), 7.73 (d, 1H, J=6.0 Hz), 7.55 (t, 2H, J=5.2 Hz), 7.33 (d, 1H, J=9.2 Hz), 7.08 (t, 2H, J=5.6 Hz), 6.87-6.78 (m, 2H), 4.97 (q, 1H, J=8.4 Hz), 3.13-3.06 (m, 2H), 1.99-1.96 (m, 1H), 1.89-1.85 (m, 1H), 1.79 (s, 3H);

MS: m/z 377.0 (M+1).

The above product was resolved into its two enantimers by chiral SFC. Method: Column: YMC Cellulose C; Mobile Phase 'A': 20 mM Ammonia in IPA; Flow: 3.0 mL/min.

Example 14a: (−)-N-{3-[(1H-1,3-benzodiazol-2-yl) amino]-3-[3-(trifluoromethyl)phenyl] propyl}acetamide (Isomer 1)

The (−) enantiomer was the first to elute off the column.

¹H NMR (400 MHz, CD₃OD): δ 7.78 (s, 1H), 7.70 (t, 1H, J=1.6 Hz), 7.57-7.51 (m, 2H), 7.19-7.17 (m, 2H), 6.98-6.94 (m, 2H), 5.01 (t, 1H, J=7.2 Hz), 3.38-3.33 (m, 1H), 3.33-3.30 (m, 1H), 2.08 (q, 2H, J=7.6 Hz), 1.95 (s, 3H);

MS: m/z 377.0 (M+1);

Chiral SFC: RT=2.62; $[\alpha]_D^{25.4}$=−79.8 (MeOH, c=0.10).

Example 14b: (+)-N-{3-[(1H-1,3-benzodiazol-2-yl) amino]-3-[3-(trifluoromethyl)phenyl] propyl}acetamide (Isomer 2)

The (+) enantiomer was the second to elute off the column.

¹H NMR (400 MHz, CD3OD): δ 7.78 (s, 1H), 7.70 (t, 1H, J=1.6 Hz), 7.57-7.51 (m, 2H), 7.19-7.17 (m, 2H), 6.98-6.94 (m, 2H), 5.01 (t, 1H, J=7.2 Hz), 3.38-3.33 (m, 1H), 3.33-3.30 (m, 1H), 2.08 (q, 2H, J=7.6 Hz), 1.95 (s, 3H);

MS: m/z 377.0 (M+1);

Chiral SFC: RT=3.35; $[\alpha]_D^{25.7}$=+77.14 (MeOH, c=0.14).

Example 15: Preparation of N-(3-{[4-(hydroxymethyl)-1H-1,3-benzodiazol-2-yl]amino}-3-[3-(trifluoromethyl)phenyl]propyl)-1,2-oxazole-3-carboxamide

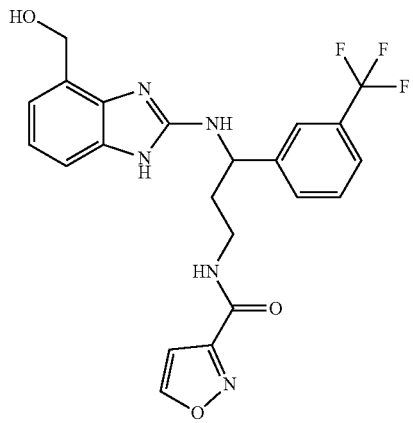 [SMILES: O=C(NCCC(Nc1nc2c(CO)cccc2[nH]1)c1cccc(C(F)(F)F)c1)c1ccon1]

Step 1: Preparation of tert-butyl N-[3-(1,2-oxazol-3-ylformamido)-1-[3-(trifluoromethyl)phenyl]propyl]carbamate

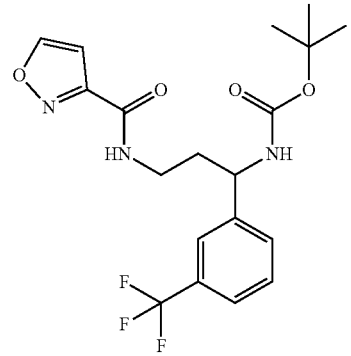 [SMILES: CC(C)(C)OC(=O)NC(CCNC(=O)c1ccon1)c1cccc(C(F)(F)F)c1]

To a stirred solution of tert-butyl N-{3-amino-1-[3-(trifluoromethyl)phenyl]propyl}carbamate (from Example 14, step 6) (3 g, 9.43 mmol) under nitrogen atmosphere in THF (30 mL) was added TEA (2.4 g, 17.25 mmol) at 0° C. followed by HBTU (7.1 g, 19 mmol). After 15 min, isoxazole-3-carboxylic acid (1.06 g, 9.38 mmol) was added portion wise and the reaction mixture was slowly warmed to ambient temperature and stirred for 18 h. The reaction mixture was quenched with water (50 mL) and extracted with ethyl acetate (3×50 mL). The combined organic layer was washed with brine solution (100 mL), dried over sodium sulphate, filtered and concentrated to afford a gum (2.0 g), which was purified by silica gel (60-120 mesh) column chromatography eluting with 7% methanol in chloroform to afford the desired product tert-butyl N-[3-(1,2-oxazol-3-ylformamido)-1-[3-(trifluoromethyl)phenyl]propyl]carbamate (1.2 g) as a colourless gum.

¹H NMR (400 MHz, DMSO-d₆/D₂O) δ 9.07 (d, 1H, J=1.60 Hz), 7.68-7.55 (m, 4H), 6.85 (d, 1H, J=1.60 Hz), 4.67 (q, 1H, J=7.60 Hz), 3.25 (d, 2H, J=6.40 Hz), 1.93 (d, 2H, J=7.20 Hz), 1.33 (s, 9H); MS: m/z 314.1 [(M+1)-Boc].

Step 2: Preparation of N-{3-amino-3-[3-(trifluoromethyl)phenyl]propyl}-1,2-oxazole-3-carboxamide hydrochloride

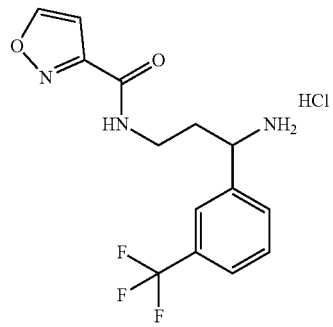 [SMILES: NC(CCNC(=O)c1ccon1)c1cccc(C(F)(F)F)c1 ; Cl]

To a stirred solution of tert-butyl N-[3-(1,2-oxazol-3-ylformamido)-1-[3-(trifluoromethyl)phenyl]propyl]carbamate (from step 1) (1.2 g, 3 mmol) under nitrogen atmosphere in DCM (15 mL) was added 4.0 M HCl in dioxane (7.25 mL, 14 mmol) at −20° C. and then it was slowly warmed to ambient temperature. After 4 h, the solid formed in the reaction mass was concentrated and the solid was washed with hexane and dried to afford N-{3-amino-3-[3-(trifluoromethyl)phenyl]propyl}-1,2-oxazole-3-carboxamide hydrochloride (0.95 g) as yellow gum, used in the next step without further purification.

$^1$H NMR (400 MHz, DMSO-$d_6$/$D_2O$) δ 9.08 (d, 1H, J=1.20 Hz), 8.01-7.61 (m, 4H), 6.88 (d, 1H, J=1.20 Hz), 4.44 (bs, 1H), 3.22 (dd, 1H, J=13.2, 6.4 Hz), 3.12 (dd, 1H, J=13.2, 6.4 Hz), 2.25 (dd, 1H, J=13.2, 6.8 Hz), 2.17 (dd, 1H, J=14.4, 7.2 Hz);

MS: m/z 314.1 (M+1).

Step 3: Preparation of N-{3-isothiocyanato-3-[3-(trifluoromethyl)phenyl]propyl}-1,2-oxazole-3-carboxamide

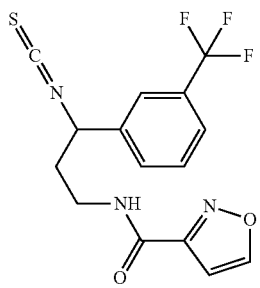 [SMILES: O=C(NCCC(N=C=S)c1cccc(C(F)(F)F)c1)c1ccon1]

To a suspension of N-{3-amino-3-[3-(trifluoromethyl)phenyl]propyl}-1,2-oxazole-3-carboxamide hydrochloride (from step 2) (0.95 g, 2.73 mmol) in dichloromethane (10 mL) cooled at 0° C. was added thiophosgene (0.21 mL, d=1.5 gm/mL, 2.73 mmol) followed by 10% aqueous sodium bicarbonate solution (10 mL). The reaction mixture was stirred at ambient temperature. After 1 h, the reaction mixture was diluted with 10% aqueous sodium bicarbonate solution (15 mL) and extracted with dichloromethane (3×25 mL). The combined organic extracts were dried over anhydrous sodium sulphate and evaporated to dryness to afford N-{3-isothiocyanato-3-[3-(trifluoromethyl)phenyl]propyl}-1,2-oxazole-3-carboxamide (0.54 g) as a red gum, used in the next step without further purification.

$^1$H NMR (400 MHz, DMSO-$d_6$/$D_2O$) δ 9.04 (d, 1H, J=1.60 Hz), 7.86-7.68 (m, 4H), 6.84 (d, J=1.60 Hz, 1H), 5.29 (dd, 1H, J=8.4, 5.2 Hz), 3.20-3.08 (m, 2H), 2.37-2.24 (m, 2H);

MS: m/z 356.1 (M+1)

Step 4: Preparation of 2,1,3-benzothiadiazol-4-ylmethanol

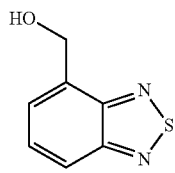

To a stirred solution of 4-(bromomethyl)-2,1,3-benzothiadiazole (commercially available) (5 g, 22 mmol) in 1:1 mixture of dioxane:water (60 mL) was added $K_2CO_3$ (15 g, 109 mmol) and refluxed. After 16 h, the above reaction mixture was quenched with water (25 mL) and was extracted with ethyl acetate (3×150 mL). The combined organic layer was washed with brine solution (25 mL), dried over sodium sulphate, filtered and concentrated to afford desired product (3.0 g) as yellow liquid. It was purified by flash column (230-400 silica gel), eluted with 30% ethyl acetate in hexane to afford 2,1,3-benzothiadiazol-4-ylmethanol (2.5 g) as yellow solid.

$^1$H NMR (400 MHz, DMSO-$d_6$) δ 7.96 (d, 1H, J=8.40 Hz), 7.75-7.68 (m, 2H), 5.51 (t, 1H, J=5.60 Hz), 5.02 (d, 2H, J=5.20 Hz);

MS: m/z 166 (M).

Step 5: Preparation of (2,3-diaminophenyl)methanol

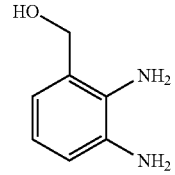

To a stirred solution of 2,1,3-benzothiadiazol-4-ylmethanol (2.5 g, 15 mmol) (from step 4) in methanol (150 mL) was added raney nickel (100% w/w, washed five times with methanol) and it was hydrogenated (under balloon pressure) at ambient temperature. After 16 h, the above reaction mass was filtered through a celite bed, the residue was washed with methanol (3×250 mL). The combined filtrate was concentrated to afford (2,3-diaminophenyl)methanol (1.6 g) as a gum.

$^1$H NMR (400 MHz, DMSO-$d_6$) δ 6.48 (d, 1H, J=7.20 Hz), 6.42 (d, 1H, J=7.20 Hz), 6.36 (t, 1H, J=7.20 Hz), 4.92 (br.s, 1H), 4.43 (s, 2H), 4.35 (d, 4H, J=14.80 Hz);

MS: m/z 139 (M+1).

Step 6: Preparation of N-[3-({[2-amino-3-(hydroxymethyl)phenyl]carbamothioyl}amino)-3-[3-(trifluoromethyl)phenyl]propyl]-1,2-oxazole-3-carboxamide

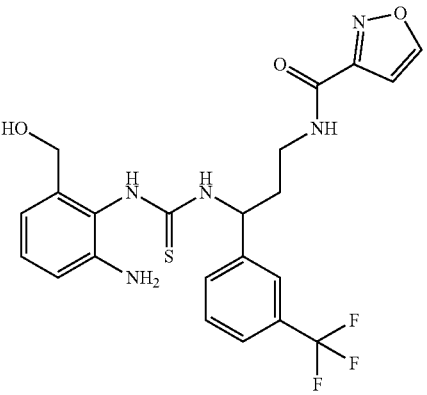 [SMILES: Nc1cccc(CO)c1NC(=S)NC(CCNC(=O)c1ccon1)c1cccc(C(F)(F)F)c1]

A mixture of (2,3-diaminophenyl)methanol (from step 5) (0.2 g, 1.45 mmol) and N-{3-isothiocyanato-3-[3-(trifluoromethyl)phenyl]propyl}-1,2-oxazole-3-carboxamide (from step 3) (0.54 g, 1.52 mmol) in dichloromethane (20 mL) was stirred at ambient temperature for 12 h. The reaction mixture was concentrated to afford a crude product (0.45 g) as a yellow gum, which was purified by silica gel (60-120 mesh) column chromatography eluted with 7% methanol in chloroform to afford the desired product N-[3-({[2-amino-3-(hydroxymethyl)phenyl]carbamothioyl}amino)-3-[3-(trifluoromethyl)phenyl]propyl]-1,2-oxazole-3-carboxamide (0.3 g) as a yellow solid.

MS: m/z 494.1 (M+1).

Example 15, Step 7: Preparation of N-(3-{[4-(hydroxymethyl)-1H-1,3-benzodiazol-2-yl]amino}-3-[3-(trifluoromethyl)phenyl]propyl)-1,2-oxazole-3-carboxamide

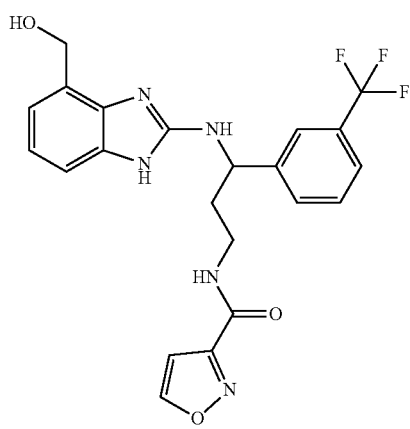 [SMILES: O=C(NCCC(Nc1nc2c(CO)cccc2[nH]1)c1cccc(C(F)(F)F)c1)c1ccon1]

To a stirred solution of N-[3-({[2-amino-3-(hydroxymethyl)phenyl]carbamothioyl}amino)-3-[3-(trifluoromethyl)phenyl]propyl]-1,2-oxazole-3-carboxamide (from step 6) (0.3 g, 0.6 mmol) in methanol (10 mL) was added iodoacetic acid (0.13 g, 0.7 mmol) and the mixture was refluxed for 2 h. The reaction mixture was evaporated to afford the crude product (0.15 g) which was purified by silica gel (60-120 mesh) column chromatography using 10% methanol in chloroform as eluent, to afford desired product N-(3-{[4-(hydroxymethyl)-1H-1,3-benzodiazol-2-yl]amino}-3-[3-(trifluoromethyl)phenyl]propyl)-1,2-oxazole-3-carboxamide (0.051 g) as a brown solid.

$^1$H NMR (400 MHz, AcOH-d$_4$) δ 8.71 (d, 1H, J=1.60 Hz), 7.83 (t, 2H, J=7.60 Hz), 7.63-7.56 (m, 2H), 7.38 (d, 1H, J=7.60 Hz), 7.23-7.16 (m, 2H), 6.90 (d, 1H, J=1.60 Hz), 5.22 (q, 1H, J=4.00 Hz), 4.87 (s, 2H), 3.81 (dd, 1H, J=8.4, 5.2 Hz), 3.67 (dd, 1H, J=11.6, 5.6 Hz), 2.42-2.32 (m, 2H);

MS: m/z 460.1 (M+1).

Example 16: Preparation of N-{3-[(1H-1,3-benzodiazol-2-yl)amino]-3-[3-(trifluoromethyl)phenyl]propyl}-2,2,2-trifluoroacetamide; formic acid

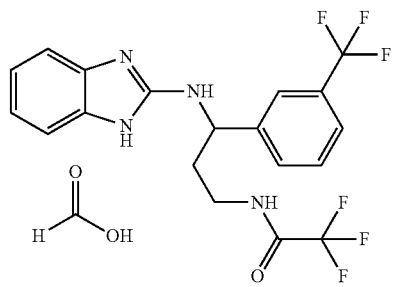

Step 1: Preparation of tert-butyl N-[3-(trifluoroacetamido)-1-[3-(trifluoromethyl)phenyl]propyl]carbamate

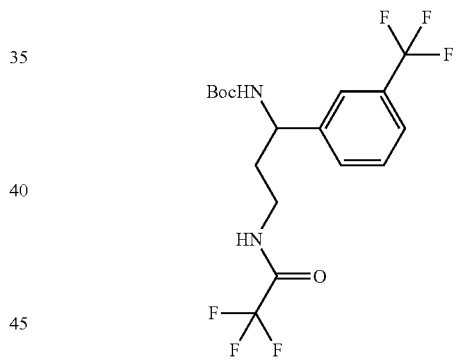

To a solution of tert-butyl N-{3-azido-1-[3-(trifluoromethyl)phenyl]propyl}carbamate (from Example 14, step 6) (1.5 g, 4.712 mmol) in dichloromethane (30 mL) was added TEA (2.65 mL, d=0.726 g/cm$^3$, 18.848 mmol) followed by 2,2,2-trifluoroacetic anhydride (3.2 mL, d=1.49 g/cm$^3$, 23.560 mmol) at 0° C. The reaction mixture was stirred at ambient temperature for 2 h. The reaction mixture was diluted with water (50 mL) and extracted with dichloromethane (3×200 mL) and the combined organic layer was dried over sodium sulphate, filtered and concentrated to afford tert-butyl N-[3-(trifluoroacetamido)-1-[3-(trifluoromethyl)phenyl]propyl]carbamate (1.9 g) as a brownish gum, which was used in the next step without further purification.

MS: m/z 315.3 [(M+1)-Boc].

Step 2: Preparation of N-{3-amino-3-[3-(trifluoromethyl)phenyl]propyl}-2,2,2-trifluoroacetamide hydrochloride

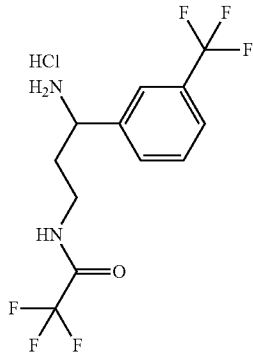

To a suspension tert-butyl N-[3-(trifluoroacetamido)-1-[3-(trifluoromethyl)phenyl]propyl]carbamate (from step 1) (2.0 g, 4.83 mmol) in DCM (40 mL) was added 4M HCl in dioxane (6.0 mL, 24.13 mmol) at 0° C. and the reaction mass was slowly warmed to ambient temperature and was stirred for 3 h. The reaction mixture was concentrated to afford N-{3-amino-3-[3-(trifluoromethyl)phenyl]propyl}-2,2,2-trifluoroacetamide hydrochloride (0.9 g) as a white solid, which was used in the next step without further purification.

MS: m/z 315.1 (M+1).

Step 3: Preparation of 2,2,2-trifluoro-N-{3-isothiocyanato-3-[3-(trifluoromethyl)phenyl]propyl}acetamide

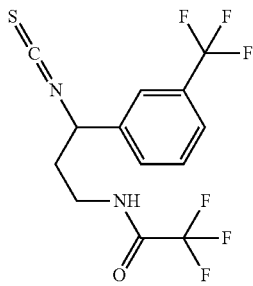 [SMILES: O=C(NCCC(N=C=S)c1cccc(C(F)(F)F)c1)C(F)(F)F]

To a suspension of N-{3-amino-3-[3-(trifluoromethyl)phenyl]propyl}-2,2,2-trifluoroacetamide hydrochloride (from step 2) (0.9 g, 2.86 mmol) in dichloromethane (30 mL) was added thiophosgene (0.6 mL, d=1.5 g/cm$^3$, 7.56 mmol) followed by 10% aqueous sodium bicarbonate solution (15 mL) cooled at 0° C. The reaction mixture was then stirred at ambient temperature for 1 h. The reaction mixture was diluted with 10% aqueous sodium bicarbonate solution (20 mL) and extracted with dichloromethane (3×100 mL). The combined organic extracts were dried over anhydrous sodium sulphate and evaporated to dryness to afford 2,2,2-trifluoro-N-{3-isothiocyanato-3-[3-(trifluoromethyl)phenyl]propyl}acetamide (0.9 g) as red gum, which was used in the next step without further purification.

MS: m/z 357.3 (M+1).

Step 4: Preparation of N-(3-{[(2-aminophenyl)carbamothioyl]amino}-3-[3-(trifluoromethyl)phenyl]propyl)-2,2,2-trifluoroacetamide

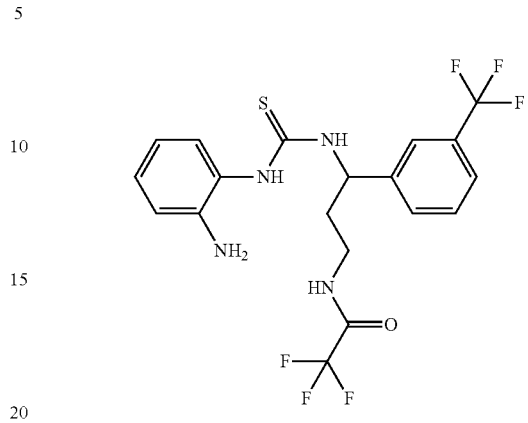

A mixture of 2,2,2-trifluoro-N-{3-isothiocyanato-3-[3-(trifluoromethyl)phenyl]propyl}acetamide (from step 3) (0.9 g, 2.53 mmol) and benzene-1,2-diamine (commercially available) (0.275 g, 2.53 mmol) in dichloromethane (30 mL) was stirred at ambient temperature for 12 h. The reaction mixture was concentrated to afford N-(3-{[(2-aminophenyl)carbamothioyl]amino}-3-[3-(trifluoromethyl)phenyl]propyl)-2,2,2-trifluoroacetamide (1.0 g) as a brownish gum, which was used in next step without any further purification.

MS: m/z 465.2 (M+1).

Example 16, Step 5: Preparation of N-{3-[(1H-1,3-benzodiazol-2-yl)amino]-3-[3-(trifluoromethyl)phenyl]propyl}-2,2,2-trifluoroacetamide; formic acid

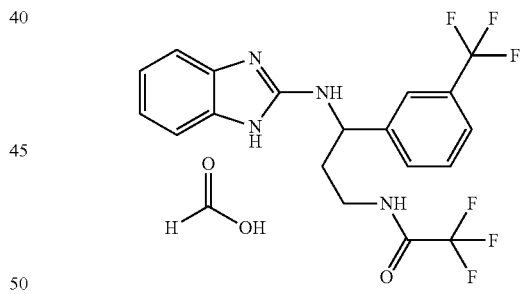

To a stirred solution of N-(3-{[(2-aminophenyl)carbamothioyl]amino}-3-[3-(trifluoromethyl)phenyl]propyl)-2,2,2-trifluoroacetamide (from step 4) (1.07 g, 2.30 mmol) in methanol (10 mL) was added iodoacetic acid (0.652 g, 3.45 mmol) and the mixture was refluxed for 2 h. The reaction mixture was evaporated to afford the crude product (1 g) which was purified by Preparative HPLC to afford N-{3-[(1H-1,3-benzodiazol-2-yl)amino]-3-[3-(trifluoromethyl)phenyl]propyl}-2,2,2-trifluoroacetamide; formic acid (0.150 g) as an off-white solid.

$^1$H NMR (400 MHz, AcOH-d$_4$) δ 8.11 (s, 1H, formate salt proton), 7.81 (t, 2H, J=15.6 Hz), 7.65-7.57 (m, 2H), 7.38 (dd, 2H, J=2.8, 5.6 Hz), 7.25-7.22 (m, 2H), 5.00 (dd, 1H, J=5.2, 9.2 Hz), 3.63 (t, 2H, J=6.4 Hz), 2.42-2.47 (m, 2H);

MS: m/z 431.1 (M+1).

Example 17: N-{4-[(1H-1,3-benzodiazol-2-yl)amino]-4-[3-(trifluoromethyl)phenyl]butan-2-yl}acetamide; trifluoroacetic acid

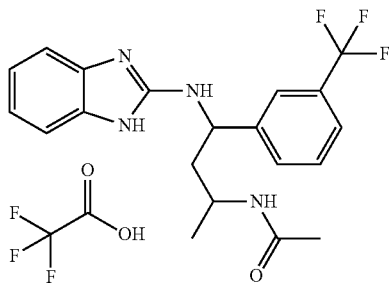

Step 1: Preparation of tert-butyl N-{2-[methoxy(methyl)carbamoyl]-1-[3-(trifluoromethyl)phenyl]ethyl}carbamate

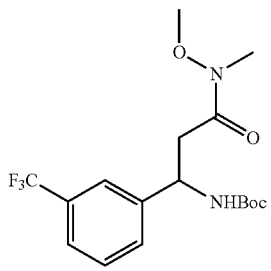 [SMILES: CON(C)C(=O)CC(NC(=O)OC(C)(C)C)c1cccc(C(F)(F)F)c1]

To a mixture of 3-{[(tert-butoxy)carbonyl]amino}-3-[3-(trifluoromethyl)phenyl]propanoic acid (from Example 14, step 2) (1.7 g, 5 mmol), N,O-dimethyl hydroxylamine (0.46 g, 8 mmol) and DIEA (1.97 g, 15 mmol) in DMF (50 mL) was added HBTU (2.32 g, 6 mmol) and stirred for 12 h at RT. The reaction mixture was poured into ice water (100 ml) and stirred for 4 h to form a precipitate. The precipitate was filtered and dried under vacuum to obtain 0.92 g of tert-butyl N-{2-[methoxy(methyl)carbamoyl]-1-[3-(trifluoromethyl)phenyl]ethyl}carbamate (0.92 g) as an off-white solid.

$^1$H NMR (400 MHz, DMSO-d$_6$) δ 7.64 (s, 1H), 7.60-7.50 (m, 4H), 5.01 (q, 1H, J=7.0 Hz), 3.58 (s, 3H), 3.03 (s, 3H), 2.86 (m, 1H), 2.78 (m, 1H), 1.34 (s, 9H);

MS: m/z 277 [(M+1)-Boc].

Step 2: Preparation of tert-butyl N-{3-oxo-1-[3-(trifluoromethyl)phenyl]butyl}carbamate

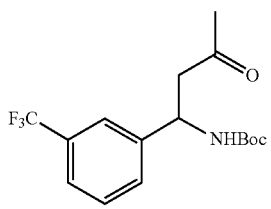 [SMILES: CC(=O)CC(NC(=O)OC(C)(C)C)c1cccc(C(F)(F)F)c1]

To a solution of tert-butyl N-{2-[methoxy(methyl)carbamoyl]-1-[3-(trifluoromethyl)phenyl]ethyl}carbamate (from step 1) (4.5 g, 12 mmol) in anhydrous THF (45 mL), methyl magnesium bromide (4.99 g, 2M solution in THF, 42 mmol) was added at 0° C. The reaction mixture was allowed to attain RT and stirred for 12 h. The mixture was diluted with saturated ammonium chloride solution (30 mL) at 0° C., extracted with DCM (2×30 mL) and evaporated to obtained a crude product. This was purified by silica gel (60-120 mesh) column chromatography eluting with 2% methanol in chloroform to afford tert-butyl N-{3-oxo-1-[3-(trifluoromethyl)phenyl]butyl}carbamate (2.9 g) as a pale yellow solid.

$^1$H NMR (400 MHz, CDCl$_3$) δ 7.56-7.52 (m, 3H), 7.48-7.47 (m, 1H), 5.60 (br.s, 1H), 5.12 (br.s, 1H), 3.08 (dd, 1H, J=16.8, 4.4 Hz), 2.96 (dd, 1H, J=16.8, 5.6 Hz), 2.13 (s, 3H), 1.46 (s, 9H);

MS: m/z 232 [(M+1)-Boc].

Step 3: Preparation of tert-butyl N-{3-amino-1-[3-(trifluoromethyl)phenyl]butyl}carbamate

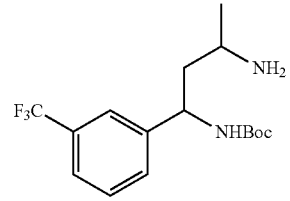 [SMILES: CC(N)CC(NC(=O)OC(C)(C)C)c1cccc(C(F)(F)F)c1]

A mixture of tert-butyl N-{3-oxo-1-[3-(trifluoromethyl)phenyl]butyl}carbamate (from step 2) (2.9 g, 9.0 mmol) in anhydrous methanol (40 mL), catalytic amount of acetic acid, powder molecular sieves (1 g) and ammonium acetate (2.69 g, 35.0 mmol) and palladium on carbon (0.93 g) were placed under an inert atmosphere. This reaction mixture was then stirred under a hydrogen atmosphere (with balloon pressure) for 12 h at ambient temperature. The reaction mixture was filtered through a bed of celite, washed with DCM (100 mL) and evaporated to dryness to afford tert-butyl N-{3-amino-1-[3-(trifluoromethyl)phenyl]butyl}carbamate (2.7 g) as a colourless gum.

MS: m/z 333.3 (M+1).

Step 4: Preparation of tert-butyl N-{3-acetamido-1-[3-(trifluoromethyl)phenyl]butyl} carbamate

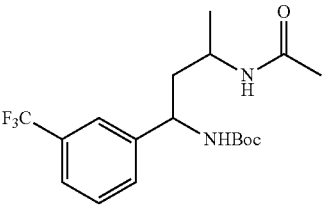 [SMILES: CC(=O)NC(C)CC(NC(=O)OC(C)(C)C)c1cccc(C(F)(F)F)c1]

To a mixture of tert-butyl N-{3-amino-1-[3-(trifluoromethyl)phenyl]butyl}carbamate (from step 3) (1 g, 3.0 mmol) and trimethylamine (0.912 g, 9.0 mmol) in DCM (50 mL), acetic anhydride (0.369 g, 3.6 mmol) was added dropwise at 0° C. and stirred for 2 h at RT. The reaction mixture was diluted with water (50 mL), extracted with DCM (2×30 mL), dried over sodium sulphate and evaporated to give the crude product, which was purified by column chromatography on silica gel (60-120 mesh) eluting with 1.5% MeOH in DCM to afford tert-butyl N-{3-acetamido-1-[3-(trifluoromethyl)phenyl]butyl}carbamate (0.75 g) as an off-white solid.

$^1$H NMR (400 MHz, CDCl$_3$) δ 7.56-7.48 (m, 4H), 4.75 (br.s, 1H), 3.95 (br.s, 1H), 2.13-2.11 (m, 2H), 1.95 (s, 3H), 1.59 (s, 3H), 1.45 (s, 9H);

MS: m/z 275.2 [(M+1)-Boc].

Step 5: Preparation of N-{4-amino-4-[3-(trifluoromethyl)phenyl]butan-2-yl}acetamide hydrochloride

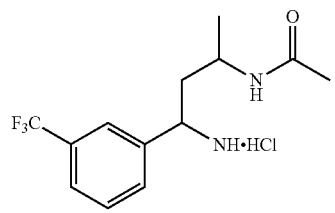

To a solution tert-butyl N-{3-acetamido-1-[3-(trifluoromethyl)phenyl]butyl}carbamate (from step 4) (0.75 g, 2.0 mmol) in DCM (10 mL), was added 4.0 M HCl in 1,4-dioxane (0.5 mL) at 0° C. and the reaction mixture was slowly warmed to ambient temperature and stirred for 16 h. The reaction mixture was filtered and dried to afford N-{4-amino-4-[3-(trifluoromethyl)phenyl]butan-2-yl}acetamide hydrochloride (0.58 g) as an off-white solid.

MS: m/z 275.2 (M+1).

Step 6: Preparation of N-{4-isothiocyanato-4-[3-(trifluoromethyl)phenyl]butan-2-yl}acetamide

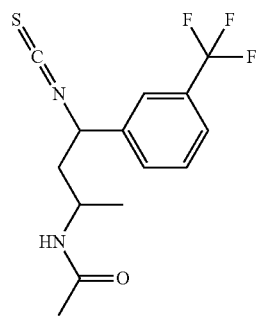 [SMILES: CC(=O)NC(C)CC(N=C=S)c1cccc(C(F)(F)F)c1]

To a suspension of N-{4-amino-4-[3-(trifluoromethyl)phenyl]butan-2-yl}acetamide hydrochloride (from step 5) (0.58 g, 1.9 mmol) in dichloromethane (20 mL) at 0° C. was added thiophosgene (0.286 mL, d=1.5 g/mL, 3.70 mmol) followed by 10% aqueous sodium bicarbonate solution (10 mL). The reaction mixture was then stirred at ambient temperature. After 1 h, the reaction mixture was diluted with 10% aqueous sodium bicarbonate solution (25 mL) and extracted with dichloromethane (3×20 mL). The combined organic extracts were dried over anhydrous sodium sulphate and evaporated to dryness to afford N-{4-isothiocyanato-4-[3-(trifluoromethyl)phenyl]butan-2-yl}acetamide (0.39 g) as a red gum.

MS: m/z 317.1.2 (M+1).

Step 7: Preparation of N-(4-{[(2-aminophenyl)carbamothioyl]amino}-4-[3-(trifluoromethyl)phenyl]butan-2-yl)acetamide

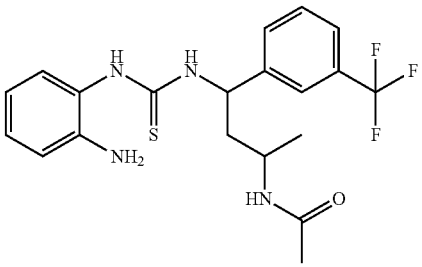 [SMILES: CC(=O)NC(C)CC(NC(=S)Nc1ccccc1N)c1cccc(C(F)(F)F)c1]

A mixture of N-{4-isothiocyanato-4-[3-(trifluoromethyl)phenyl]butan-2-yl}acetamide (from step 6) (0.39 g, 1.23 mmol) and 1,2-phenylene diamine (commercially available) (0.20 g, 1.85 mmol) in dichloromethane (20 mL) was stirred at ambient temperature for 12 h. The reaction mixture was concentrated to afford a crude product (0.45 g) as a brownish gum. This was purified by silica gel (60-120 mesh) column chromatography eluting with 3% methanol in chloroform to afford N-(4-{[(2-aminophenyl)carbamothioyl]amino}-4-[3-(trifluoromethyl)phenyl]butan-2-yl)acetamide (0.35 g) as a brown solid.

MS: m/z 425.3 (M+1).

Example 17, Step 8: N-{4-[(1H-1,3-benzodiazol-2-yl)amino]-4-[3-(trifluoromethyl)phenyl]butan-2-yl}acetamide; trifluoroacetic acid

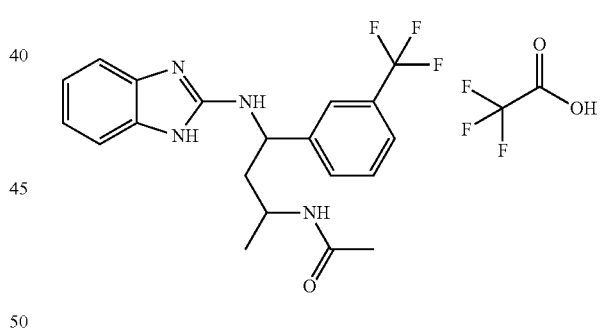

To a solution of N-(4-{[(2-aminophenyl)carbamothioyl]amino}-4-[3-(trifluoromethyl)phenyl]butan-2-yl)acetamide (from step 7) (0.35 g, 0.824 mmol) in methanol (5 mL) was added iodoacetic acid (0.184 g, 0.989 mmol) and the mixture was refluxed for 2 h. The reaction mixture was evaporated to afford the crude product (0.5 g) which was purified by preparative HPLC to afford N-{4-[(1H-1,3-benzodiazol-2-yl)amino]-4-[3-(trifluoromethyl)phenyl]butan-2-yl}acetamide; trifluoroacetic acid (0.11 g) as an off-white solid.

$^1$H NMR (400 MHz, DMSO-d$_6$) δ 12.73-12.67 (m, 1H), 9.73-9.60 (m, 1H), 7.85 (q, 2H, J=14.8, 8.8 Hz), 7.75-7.62 (m, 3H), 7.39-7.35 (m, 2H), 7.24-7.23 (m, 2H), 4.93-4.85 (m, 1H), 4.07 (br.s, 1H), 2.13-1.99 (m, 1H), 1.91-1.80 (m, 1H), 1.76 (s, 3H), 1.09 (d, 3H, J=6.8 Hz);

MS: m/z 391.2 (M+1).

Example 18: Preparation of N-{3-[(1H-1,3-benzodi-azol-2-yl)amino]-3-[3-(trifluoromethyl)phenyl]pro-pyl}-N-methylacetamide

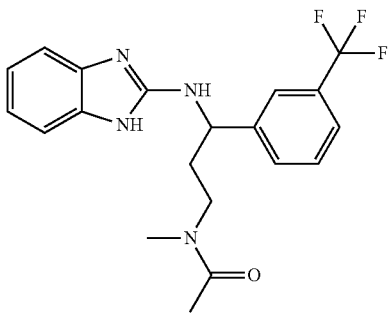 [SMILES: CC(=O)N(C)CCC(Nc1nc2ccccc2[nH]1)c1cccc(C(F)(F)F)c1]

Step 1: Preparation of tert-butyl N-[3-(methyl-amino)-1-[3-(trifluoromethyl)phenyl]propyl]carbam-ate

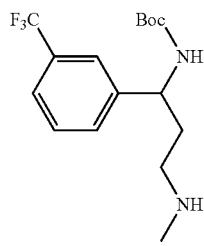

To a suspension of methylamine hydrochloride (2 g, 30 mmol) in acetonitrile (200 mL) was added potassium carbonate (5.2 g, 37.6 mmol) and stirred for 5 min. Then tert-butyl N-[3-(methanesulfonyloxy)-1-[3-(trifluoromethyl)phenyl]propyl]carbamate (from Example 14, step 4) (3 g, 7.6 mmol) was added at 0° C. and stirred at room temperature for 5 days. The reaction mixture was filtered and the filtrate was concentrated to afford tert-butyl N-[3-(methylamino)-1-[3-(trifluoromethyl)phenyl]propyl]carbamate (2.3 g) as a brown gum.

$^1$H NMR (400 MHz, DMSO-$d_6$) δ 7.66-7.56 (m, 5H), 4.70-4.60 (m, 1H), 2.60-2.50 (m, 1H), 2.44-2.40 (m, 1H), 2.20-2.30 (m, 2H), 2.07 (t, J=2.16 Hz, 3H), 1.65-1.75 (m, 1H), 1.35 (s, 9H);

MS: m/z 333.1 (M+1).

Step 2: Preparation of tert-butyl N-[3-(N-methylac-etamido)-1-[3-(trifluoromethyl)phenyl]propyl]car-bamate

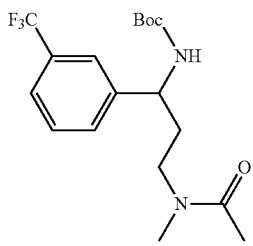

To a solution of tert-butyl N-[3-(methylamino)-1-[3-(tri-fluoromethyl)phenyl]propyl]carbamate (from step 1) (2.3 g, 7 mmol) in dichloromethane (60 mL) was added triethylamine (3.86 mL, 28 mmol) followed by acetic anhydride (0.98 mL, 10.3 mmol) at 0° C. and stirred at room temperature for 3 h. The reaction mixture was quenched with ice cold water and extracted with dichloromethane (300 mL), washed with brine solution, dried over sodium sulphate, filtered and concentrated to afford a brownish gum, which was purified by silica gel (230-400 mesh) column chromatography eluting with 4% methanol in chloroform to afford tert-butyl N-[3-(N-methylacetamido)-1-[3-(trifluoromethyl)phenyl]propyl]carbamate (1.6 g) as colourless gum.

$^1$H NMR (400 MHz, DMSO-$d_6$:$D_2O$) δ 7.73-7.57 (m, 5H), 5.69-4.52 (m, 1H), 3.30-3.21 (m, 2H), 2.88 (s, 1.6H), 2.75 (s, 1.4H), 1.96-1.80 (m, 5H), 1.34 (s, 9H);

MS: 275.2 m/z [(M+1)-Boc].

Step 3: Preparation of N-{3-amino-3-[3-(trifluorom-ethyl)phenyl]propyl}-N-methylacetamide hydro-chloride

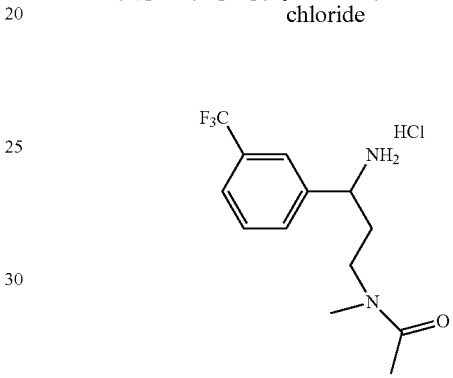

To a solution of tert-butyl N-[3-(N-methylacetamido)-1-[3-(trifluoromethyl)phenyl]propyl]carbamate (from step 2) (1.6 g, 4.27 mmol) in dichloromethane (300 mL) was added conc. HCl (12 mL) at 0° C. for 3 h. The reaction mixture was concentrated to afford N-{3-amino-3-[3-(trifluoromethyl)phenyl]propyl}-N-methylacetamide hydrochloride (1 g) as a yellowish gum.

$^1$H NMR (400 MHz, DMSO-$d_6$) δ 8.85 (s, 1H), 8.72 (s, 2H), 7.98 (d, J=10.96 Hz, 1H), 7.90 (t, J=7.92 Hz, 1H), 7.75 (d, J=7.48 Hz, 1H), 7.72-7.64 (m, 1H), 4.31 (bs, 1H), 3.27-3.21 (m, 2H), 2.88 (s, 2H), 2.71 (s, 1H), 2.20-2.00 (m, 2H), 1.96-1.84 (m, 3H);

MS: 275.2 m/z (M+1).

Step 4: Preparation of N-{3-isothiocyanato-3-[3-(trifluoromethyl)phenyl]propyl}-N-methylacetamide

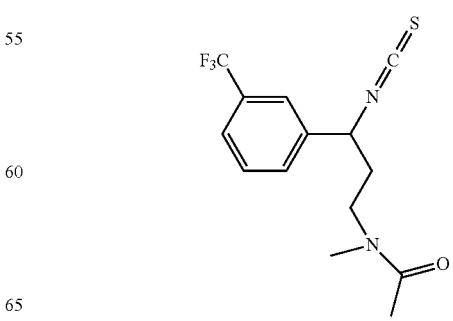

To a solution of N-{3-amino-3-[3-(trifluoromethyl)phenyl]propyl}-N-methylacetamide hydrochloride (from step 3) (1 g, 3.22 mmol) in dichloromethane (150 mL) was added 10% aqueous sodium bicarbonate solution (100 mL) followed by thiophosgene (0.42 mL, 5.4 mmol) at 0° C. and stirred at room temperature for 1 h. The reaction mixture was extracted with dichloromethane (150 mL) and dried over sodium sulphate, filtered and concentrated to afford N-{3-isothiocyanato-3-[3-(trifluoromethyl)phenyl]propyl}-N-methylacetamide (1 g) as a yellowish gum.

$^1$H NMR (400 MHz, DMSO-$d_6$) δ 7.76-7.64 (m, 4H), 5.33-5.22 (m, 1H), 3.39-3.21 (m, 2H), 2.93 (s, 2H) 2.78 (s, 1H), 2.19-2.05 (m, 2H), 1.96 (t, J=9.20 Hz, 3H) MS: 317.1 m/z (M+1).

Step 5: Preparation of N-(3-{[(2-aminophenyl)carbamothioyl]amino}-3-[3-(trifluoromethyl)phenyl]propyl)-N-methylacetamide

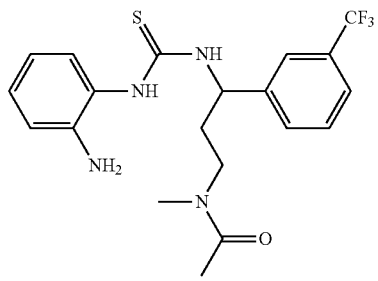 [SMILES: CC(=O)N(C)CCC(NC(=S)Nc1ccccc1N)c1cccc(C(F)(F)F)c1]

A mixture of N-{3-isothiocyanato-3-[3-(trifluoromethyl)phenyl]propyl}-N-methylacetamide (from step 4) (1 g, 3.16 mmol) and 1,2-phenylene diamine (commercially available) (0.34 g, 3.16 mmol) in dichloromethane (50 mL) was stirred at room temperature for 20 h. The reaction mixture was concentrated to afford a crude product (1.35 g) as a gum, which was purified by silica gel (230-400 mesh) column chromatography eluting with 3% methanol in chloroform to afford N-(3-{[(2-aminophenyl)carbamothioyl]amino}-3-[3-(trifluoromethyl)phenyl]propyl)-N-methylacetamide (1 g) as a brown gum.

MS: 425.2 m/z (M+1).

Example 18, Step 6: Preparation of N-{3-[(1H-1,3-benzodiazol-2-yl)amino]-3-[3-(trifluoromethyl)phenyl]propyl}-N-methylacetamide

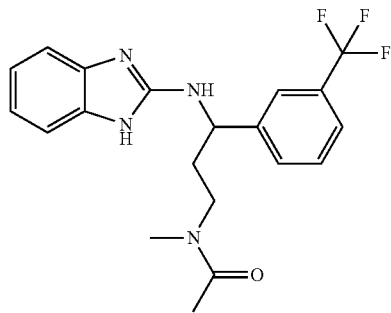 [SMILES: CC(=O)N(C)CCC(Nc1nc2ccccc2[nH]1)c1cccc(C(F)(F)F)c1]

To a solution of N-(3-{[(2-aminophenyl)carbamothioyl]amino}-3-[3-(trifluoromethyl)phenyl]propyl)-N-methylacetamide (from step 5) (1 g, 2.3 mmol) in methanol (30 mL) was added iodoacetic acid (0.87 g, 4.6 mmol) and refluxed for 1 h. The reaction mixture was evaporated to afford the crude product (1 g), which was purified by silica gel (230-400 mesh) column chromatography using 3% methanol in chloroform to afford N-{3-[(1H-1,3-benzodiazol-2-yl)amino]-3-[3-(trifluoromethyl)phenyl]propyl}-N-methylacetamide (0.4 g) as a yellowish solid.

$^1$H NMR (400 MHz, DMSO-$d_6$: $D_2O$) δ 7.80-7.71 (m, 2H), 7.56 (d, J=5.20 Hz, 2H), 7.10 (d, J=7.60 Hz, 2H), 6.87 (s, 2H), 4.88 (bs, 1H), 3.48-3.30 (m, 2H), 2.90 (s, 1.6H), 2.78 (s, 1.4H), 2.01-1.85 (m, 5H).

MS: m/z 391.2 (M+1).

The above compound was resolved into its two enantiomers by chiral SFC chromatography: (Condition: Chiral CEL OD-H; 30:70 [(IPA (0.5% DEA in IPA): $CO_2$; Flow rate: 70 mL/min).

Example 18a: (−)-N-{3-[(1H-1,3-benzodiazol-2-yl)amino]-3-[3-(trifluoromethyl)phenyl]propyl}-N-methylacetamide The (−) enantiomer was the first to elute off the column.

$^1$H NMR (400 MHz, DMSO-$d_6$: $D_2O$) δ 7.80-7.71 (m, 2H), 7.56 (d, J=5.20 Hz, 2H), 7.10 (d, J=7.60 Hz, 2H), 6.87 (s, 2H), 4.88 (bs, 1H), 3.48-3.30 (m, 2H), 2.90 (s, 1.6H), 2.78 (s, 1.4H), 2.01-1.85 (m, 5H);

MS: m/z 391.2 (M+1);

$[α]_D^{21.8}$ (−) 71.00, (MeOH, c=0.1).

Example 18b: (+)-N-{3-[(1H-1,3-benzodiazol-2-yl)amino]-3-[3-(trifluoromethyl)phenyl]propyl}-N-methylacetamide The (+) enantiomer was the second to elute off the column.

$^1$H NMR (400 MHz, DMSO-$d_6$: $D_2O$) δ 7.80-7.71 (m, 2H), 7.56 (d, J=5.20 Hz, 2H), 7.10 (d, J=7.60 Hz, 2H), 6.87 (s, 2H), 4.88 (bs, 1H), 3.48-3.30 (m, 2H), 2.90 (s, 1.6H), 2.78 (s, 1.4H), 2.01-1.85 (m, 5H); MS: m/z 391.2 (M+1);

$[α]_D^{22.5}$ (+) 73.6, (MeOH, c=0.1).

Example 19: Preparation N-{4-[(1H-1,3-benzodiazol-2-yl)amino]-4-[3-(trifluoromethyl)phenyl]butyl}acetamide

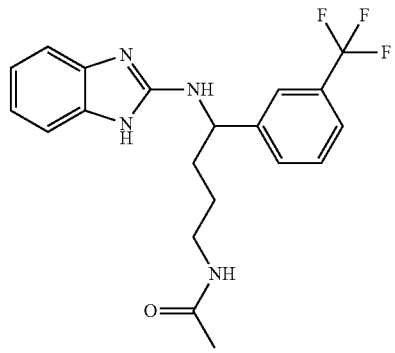 [SMILES: CC(=O)NCCCC(Nc1nc2ccccc2[nH]1)c1cccc(C(F)(F)F)c1]

Step 1: Preparation of tert-butyl N-{3-cyano-1-[3-(trifluoromethyl)phenyl]propyl} carbamate

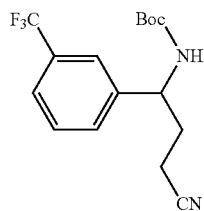

To a solution of tert-butyl N-[3-(methanesulfonyloxy)-1-[3-(trifluoromethyl)phenyl]propyl]carbamate (from Example 14, step 4) (25 g, 63 mmol) in N,N-dimethylformamide (200 mL), was added sodium cyanide (3.67 g, 75 mmol) and heated at 70° C. for 16 h. The reaction mixture was quenched with water and extracted with ethyl acetate (2×200 mL) and dried over sodium sulphate, filtered and concentrated to afford crude product (20 g), which was purified by silica gel (230-400 mesh) column chromatography eluting with 20% ethylacetate in hexane to afford tert-butyl N-{3-cyano-1-[3-(trifluoromethyl)phenyl]propyl}carbamate (13 g) as a colourless gum.

$^1$H NMR (400 MHz, DMSO-$d_6$) δ 7.66-7.56 (m, 5H), 4.67 (t, J=7.60 Hz, 1H), 2.45 (t, J=10.80 Hz, 2H), 1.99-1.92 (m, 2H), 1.41 (s, 9H);

MS: m/z 229.1 [(M+1)-Boc].

Step 2: Preparation of tert-butyl N-{4-amino-1-[3-(trifluoromethyl)phenyl]butyl}carbamate hydrochloride

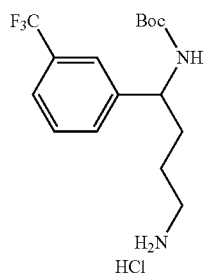

To a solution of tert-butyl N-{3-cyano-1-[3-(trifluoromethyl)phenyl]propyl}carbamate (from step 1) (6.5 g, 20 mmol) in ethanol (750 mL) were added Conc. HCl (1.8 mL, 20 mmol), Pd/C (10%, 4.2 g) and hydrogenated at 355.5 psi at 50° C. for 18 h. The reaction mixture was filtered and concentrated to afford tert-butyl N-{4-amino-1-[3-(trifluoromethyl)phenyl]butyl}carbamate hydrochloride (6 g) as yellowish gum.

MS: m/z 333.2 (M+1).

Step 3: Preparation of tert-butyl N-{4-acetamido-1-[3-(trifluoromethyl)phenyl]butyl}carbamate

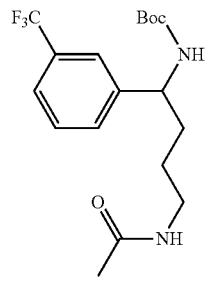 [SMILES: CC(=O)NCCCC(NC(=O)OC(C)(C)C)c1cccc(C(F)(F)F)c1]

To a solution of tert-butyl N-{4-amino-1-[3-(trifluoromethyl)phenyl]butyl}carbamate hydrochloride (from step 2) (4.5 g, 12.2 mmol) in dichloromethane (120 mL) was added triethylamine (5.1 mL, 36.6 mmol) followed by acetic anhydride (1.4 mL, 14.6 mmol) at 0° C. and then stirred at room temperature for 3 h. The reaction mixture was quenched with ice cold water, extracted with dichloromethane (200 mL), washed with brine solution, dried over sodium sulphate, filtered and concentrated to afford crude product (4 g) as a gum. This was purified by silica gel (230-400 mesh) column chromatography eluting with 4% methanol in chloroform to afford tert-butyl N-{4-acetamido-1-[3-(trifluoromethyl)phenyl]butyl}carbamate (1.5 g) as a colourless gum.

$^1$H NMR (400 MHz, DMSO-$d_6$) δ 7.80 (d, J=5.2 Hz, 1H), 7.66 (s, 1H), 7.59-7.50 (m, 4H), 4.56 (d, J=6.40 Hz, 1H), 3.02 (q, J=9.60 Hz, 2H), 1.77 (s, 3H), 1.59 (q, J=6.80 Hz, 2H), 1.44-1.43 (m, 2H), 1.36 (s, 9H);

MS: m/z 275.1[(M+1)-Boc]

Step 4: Preparation of N-{4-amino-4-[3-(trifluoromethyl)phenyl]butyl}acetamide; trifluoroacetic acid

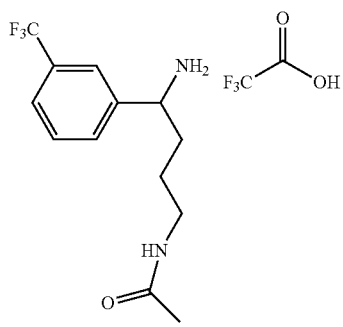 [SMILES: CC(=O)NCCCC(N)c1cccc(C(F)(F)F)c1 ; O=C(O)C(F)(F)F]

To a solution of tert-butyl N-{4-acetamido-1-[3-(trifluoromethyl)phenyl]butyl}carbamate (from step 3) (1.5 g, 4 mmol) in dichloromethane (20 mL) was added trifluoroacetic acid (1.84 mL, 24 mmol) and the reaction mixture was stirred at room temperature for 16 h. The reaction mixture was concentrated to afford N-{4-amino-4-[3-(trifluoromethyl)phenyl]butyl}acetamide; trifluoroacetic acid (1.5 g) as a colourless gum.

$^1$H NMR (400 MHz, DMSO-$d_6$) δ 8.38 (bs, 3H), 7.87 (t, J=5.20 Hz, 2H), 7.78 (d, J=7.60 Hz, 2H), 7.71 (d, J=7.60 Hz, 1H), 4.41 (t, J=4.40 Hz, 1H), 3.02 (q, J=5.20 Hz, 2H), 1.99-1.79 (m, 5H), 1.18-1.11 (m, 2H);

MS: m/z 275.1 (M+1).

Step 5: Preparation of N-{4-isothiocyanato-4-[3-(trifluoromethyl)phenyl]butyl}acetamide

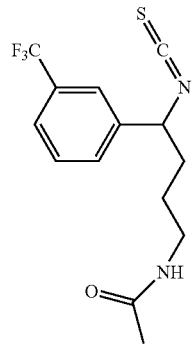 [SMILES: CC(=O)NCCCC(N=C=S)c1cccc(C(F)(F)F)c1]

To a solution of N-{4-amino-4-[3-(trifluoromethyl)phenyl]butyl}acetamide; trifluoroacetic acid (from step 4) (1.5 g, 3.86 mmol) in dichloromethane (150 mL) was added 10% aqueous sodium bicarbonate solution (100 mL) followed by thiophosgene (0.6 ml, 7.82 mmol) at 0° C. and then stirred at room temperature for 1 h. The reaction mixture was extracted with dichloromethane (2×100 mL), dried over sodium sulphate, filtered and concentrated to afford N-{4-isothiocyanato-4-[3-(trifluoromethyl)phenyl]butyl}acetamide (1.05 g) as a reddish gum.

$^1$H NMR (400 MHz, DMSO-$d_6$) δ 7.86 (s, 1H), 7.74-7.68 (m, 4H), 5.31 (q, J=5.36 Hz, 1H), 3.05 (q, J=2.60 Hz, 2H), 1.98-1.87 (m, 2H), 1.76 (s, 3H), 1.51-1.42 (m, 2H);

MS: m/z 317.0 (M+1).

Step 6: Preparation of N-(4-{[(2-aminophenyl)carbamothioyl]amino}-4-[3-(trifluoromethyl)phenyl]butyl)acetamide

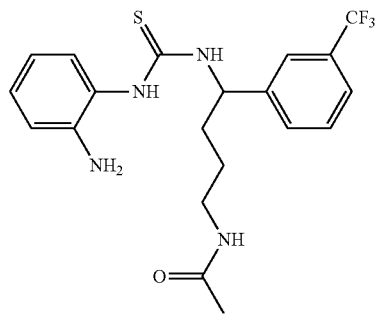 [SMILES: CC(=O)NCCCC(NC(=S)Nc1ccccc1N)c1cccc(C(F)(F)F)c1]

A mixture of N-{4-isothiocyanato-4-[3-(trifluoromethyl)phenyl]butyl}acetamide (from step 5) (1.25 g, 3.9 mmol) and 1,2-phenylene diamine (commercially available) (0.42 g, 3.9 mmol) in dichloromethane (120 mL) was stirred at room temperature for 12 h. The reaction mixture was concentrated to afford crude product (1.7 g) as a gum, which was purified by silica gel (230-400 mesh) column chromatography eluting with 3% methanol in chloroform to afford N-(4-{[(2-aminophenyl)carbamothioyl]amino}-4-[3-(trifluoromethyl)phenyl]butyl)acetamide (1 g) as a brown gum.

MS: m/z 425.1 (M+1).

Example 19, Step 7: Preparation of N-{4-[(1H-1,3-benzodiazol-2-yl)amino]-4-[3-(trifluoromethyl)phenyl]butyl}acetamide

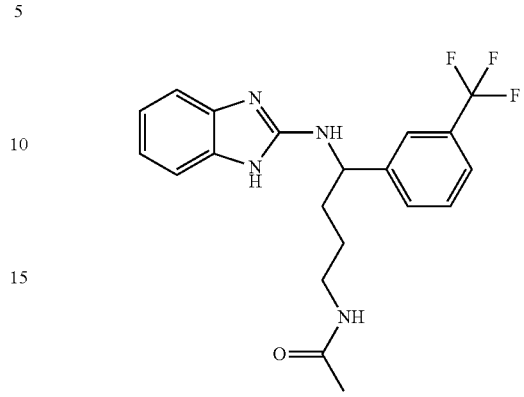

To a solution of N-(4-{[(2-aminophenyl)carbamothioyl]amino}-4-[3-(trifluoromethyl)phenyl]butyl)acetamide (from step 6) (1 g, 2.3 mmol) in methanol (30 mL) was added iodoacetic acid (0.66 g, 3.5 mmol) and refluxed for 1 h. The reaction mixture was evaporated to afford the crude product (1 g), which was purified by silica gel (230-400 mesh) column chromatography using 3% methanol in chloroform to afford N-{4-[(1H-1,3-benzodiazol-2-yl)amino]-4-[3-(trifluoromethyl)phenyl]butyl}acetamide (0.55 g) as a yellowish solid.

$^1$H NMR (400 MHz, AcOH-$d_4$) δ 7.77 (d, J=10.24 Hz, 2H), 7.63-7.55 (m, 2H), 7.37 (q, J=3.00 Hz, 2H), 7.22 (q, J=3.16 Hz, 2H), 4.99 (q, J=5.64 Hz, 1H), 3.41-3.31 (m, 2H), 2.14-1.95 (m, 5H), 1.72 (t, J=7.00 Hz, 2H).

MS: m/z 391.2 (M+1).

The above compound was resolved into its enantiomers by chiral SFC (Condition: YMC cellulose c; 30:70 [(0.5% DEA in IPA): $CO_2$], Flow rate 70 mL/min).

Example 19a: (−)-N-{4-[(1H-1,3-benzodiazol-2-yl)amino]-4-[3-(trifluoromethyl)phenyl]butyl}acetamide The (−) enantiomer was the first to elute off the column.

$^1$H NMR (400 MHz, AcOH-$d_4$) δ 7.77 (d, J=10.24 Hz, 2H), 7.63-7.55 (m, 2H), 7.37 (q, J=3.00 Hz, 2H), 7.22 (q, J=3.16 Hz, 2H), 4.99 (q, J=5.64 Hz, 1H), 3.41-3.31 (m, 2H), 2.14-1.95 (m, 5H), 1.72 (t, J=7.00 Hz, 2H);

MS: m/z 391.2 (M+1);

$[\alpha]_D^{23.7}$ (−) 59, (MeOH, c=0.1).

Example 19b: (+)-N-{4-[(1H-1,3-benzodiazol-2-yl)amino]-4-[3-(trifluoromethyl)phenyl]butyl}acetamide The (+) enantiomer was the second to elute off the column.

$^1$H NMR (400 MHz, AcOH-$d_4$) δ 7.77 (d, J=10.24 Hz, 2H), 7.63-7.55 (m, 2H), 7.37 (q, J=3.00 Hz, 2H), 7.22 (q, J=3.16 Hz, 2H), 4.99 (q, J=5.64 Hz, 1H), 3.41-3.31 (m, 2H), 2.14-1.95 (m, 5H), 1.72 (t, J=7.00 Hz, 2H);

MS: m/z 391.2 (M+1);

$[\alpha]_D^{23.8}$ (+) 60, (MeOH, c=0.1).

Example 20: Preparation of N-{4-[(5-fluoro-1H-1,3-benzodiazol-2-yl)amino]-4-[3-(trifluoromethyl)phenyl]butyl}acetamide

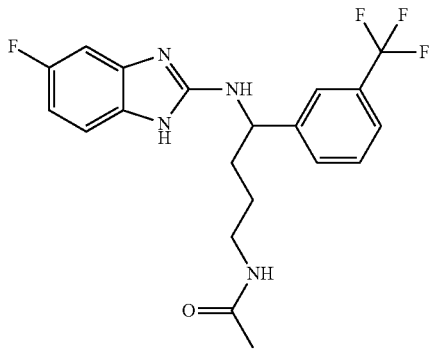 [SMILES: CC(=O)NCCCC(Nc1nc2cc(F)ccc2[nH]1)c1cccc(C(F)(F)F)c1]

Step 1: Preparation of N-(4-{[(2-amino-5-fluorophenyl)carbamothioyl]amino}-4-[3-(trifluoromethyl)phenyl]butyl)acetamide

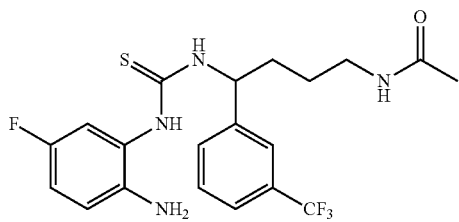 [SMILES: CC(=O)NCCCC(NC(=S)Nc1cc(F)ccc1N)c1cccc(C(F)(F)F)c1]

A mixture of N-{4-isothiocyanato-4-[3-(trifluoromethyl)phenyl]butyl}acetamide (from Example 19, step 5) (0.9 g, 3.0 mmol) and 4-fluorobenzene-1, 2-diamine (commercially available) (0.3 g, 2.0 mmol) in dichloromethane (20 mL) was stirred at ambient temperature for 12 h. The reaction mixture was concentrated to afford a crude product (1 g) as a gum, which was purified by silica gel (60-120 mesh) column chromatography eluting with 7% methanol in chloroform to afford N-(4-{[(2-amino-5-fluorophenyl)carbamothioyl]amino}-4-[3-(trifluoromethyl)phenyl]butyl)acetamide (0.8 g) as a brownish solid.
MS: m/z 443.2 (M+1).

Example 20, Step 2: Preparation of N-{4-[(5-fluoro-1H-1,3-benzodiazol-2-yl)amino]-4-[3-(trifluoromethyl)phenyl]butyl}acetamide

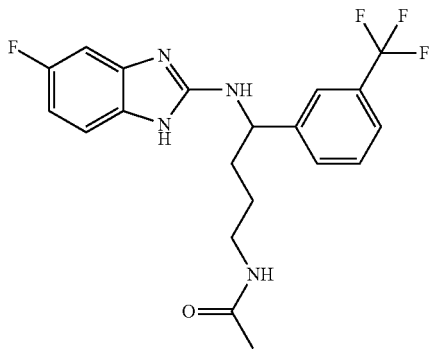 [SMILES: CC(=O)NCCCC(Nc1nc2cc(F)ccc2[nH]1)c1cccc(C(F)(F)F)c1]

To a stirred solution of N-(4-{[(2-amino-5-fluorophenyl)carbamothioyl]amino}-4-[3-(trifluoromethyl)phenyl]butyl)acetamide (from step 1) (0.8 g, 1.8 mmol) in methanol (20 mL) was added iodoacetic acid (0.5 g, 2.7 mmol) and the mixture was refluxed for 2 h. The reaction mixture was evaporated to afford the crude product (0.7 g) which was purified by silica gel (60-120 mesh) column chromatography using 7% methanol in chloroform as eluent to afford N-{4-[(5-fluoro-1H-1,3-benzodiazol-2-yl)amino]-4-[3-(trifluoromethyl)phenyl]butyl}acetamide (0.5 g) as an off-white solid.
$^1$H NMR (400 MHz, AcOH-$d_4$) δ 7.77 (d, 2H, J=9.2 Hz), 7.65-7.56 (m, 2H), 7.35 (dd, 1H, J=8.8, 4.0 Hz), 7.18 (dd, 1H, J=8.2, 1.6 Hz), 7.01-6.95 (m, 1H), 4.98 (dd, 1H, J=9.0, 6.0 Hz), 3.44-3.34 (m, 2H), 2.12 (s, 3H), 2.10-2.06 (m, 1H), 1.97 (t, 1H, J=8.0 Hz), 1.76-1.69 (m, 2H).
MS: m/z 409.2 (M+1).

Example 21: Preparation of N-{3-[(1H-1,3-benzodiazol-2-yl)amino]-3-[3-(trifluoromethyl)phenyl]butyl}acetamide

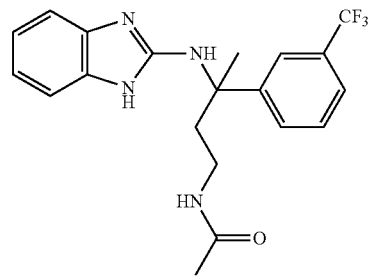 [SMILES: CC(=O)NCCC(C)(Nc1nc2ccccc2[nH]1)c1cccc(C(F)(F)F)c1]

Step 1: Preparation of 2-methyl-N-[(1E)-1-[3-(trifluoromethyl)phenyl]ethylidene] propane-2-sulfinamide

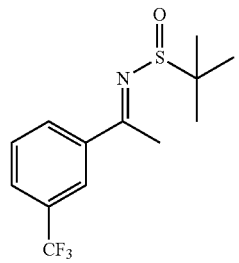 [SMILES: C/C(=N\S(=O)C(C)(C)C)c1cccc(C(F)(F)F)c1]

A mixture of 1-(3-(trifluoromethyl) phenyl)ethan-1-one (commercially available) (50.00 g, 265.74 mmol), 2-methylpropane-2-sulfinamide (32.21 g, 265.75 mmol) and titanium (IV) ethoxide (121.24 g, 531.49 mmol) in tetrahydrofuran (500 mL) was refluxed for 12 h. A solution of aq. NaHCO$_3$ (100 mL) was added to the reaction mixture, stirred for 10 mins and extracted with ethyl acetate (3×50 mL). The combined organic extracts were dried over anhydrous sodium sulphate and evaporated to dryness to afford 2-methyl-N-[(1E)-1-[3-(trifluoromethyl)phenyl]ethylidene] propane-2-sulfinamide (66.0 g) as a gum.
$^1$H NMR (400 MHz, DMSO-$d_6$) δ 8.21 (d, 1H, J=6.92 Hz), 8.17 (s, 1H), 7.94 (d, 1H, J=6.92 Hz), 7.76 (t, 1H, J=7.72 Hz), 2.79 (s, 3H), 1.24 (s, 9H);
MS: m/z 292.1 (M+1).

Step 2: Preparation of methyl 3-[(2-methylpropane-2-sulfinyl)amino]-3-[3-(trifluoromethyl)phenyl]butanoate

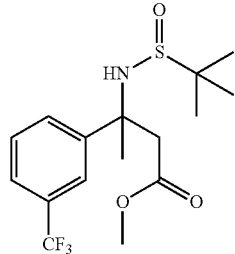 [SMILES: COC(=O)CC(C)(NS(=O)C(C)(C)C)c1cccc(C(F)(F)F)c1]

A mixture of activated Zn (116.70 g, 1784.94 mmol) and CuCl (22.09 g, 223.13 mmol) in tetrahydrofuran (250 mL) was heated at 60° C. for 30 mins and to this was slowly added methyl 2 bromoacetate (85.0 g, 557.78 mmol). The reaction mixture was cooled to 0° C. and a solution of 2-methyl-N-[(1E)-1-[3-(trifluoromethyl)phenyl]ethylidene]propane-2-sulfinamide (from step 1) (65.0 g, 223.11 mmol) in tetrahydrofuran (250 mL) was added and stirred for 1 h at 0° C. The reaction mixture was quenched with saturated ammonium chloride solution (1000 ml), extracted with ethyl acetate (3×100 mL). The combined organic extracts were dried over anhydrous sodium sulphate and evaporated to dryness to afford the methyl 3-[(2-methylpropane-2-sulfinyl)amino]-3-[3-(trifluoromethyl)phenyl]butanoate (81 g) as a gum.

MS: m/z 366.1 (M+1).

Step 3: Preparation of 3-[(2-methylpropane-2-sulfinyl)amino]-3-[3-(trifluoromethyl)phenyl]butanoic acid

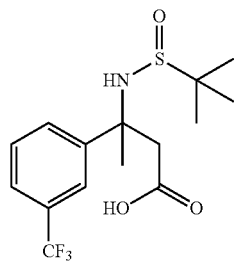 [SMILES: CC(CC(=O)O)(NS(=O)C(C)(C)C)c1cccc(C(F)(F)F)c1]

To a suspension of methyl 3-[(2-methylpropane-2-sulfinyl)amino]-3-[3-(trifluoromethyl)phenyl]butanoate (from step 2) (10 g, 27.36 mmol) in tetrahydrofuran (50 mL) and water (10 mL) was added lithium hydroxide (1.14 g, 27.35 mmol). The reaction mixture was stirred at room temperature for 24 h. The reaction mixture was evaporated to remove tetrahydrofuran and the residue was neutralised with citric acid solution (75 mL) and extracted with ethyl acetate (3×100 mL). The combined organic extracts were dried over anhydrous sodium sulphate and evaporated to dryness to afford 3-[(2-methylpropane-2-sulfinyl)amino]-3-[3-(trifluoromethyl)phenyl]butanoic acid (7.5 g) as a colourless gum.

$^1$H NMR (400 MHz, DMSO-d$_6$/D$_2$O) δ 7.74 (s, 2H), 7.60-7.60 (m, 2H), 3.16 (d, 1H, J=16.4 Hz), 2.88 (d, 1H, J=16.36 Hz), 1.71 (s, 3H), 1.14 (s, 9H);

MS: m/z 352.1 (M+1).

Step 4: Preparation of N-{4-hydroxy-2-[3-(trifluoromethyl)phenyl]butan-2-yl}-2-methylpropane-2-sulfinamide

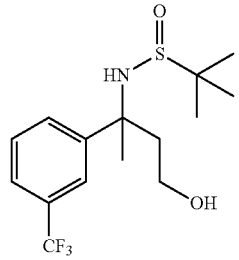 [SMILES: CC(CCO)(NS(=O)C(C)(C)C)c1cccc(C(F)(F)F)c1]

To a mixture of 3-[(2-methylpropane-2-sulfinyl)amino]-3-[3-(trifluoromethyl)phenyl]butanoic acid (from step 3) (7.5 g, 21.34 mmol) in tetrahydrofuran (30 mL) was added borane dimethyl sulphide complex (6.48 g, 85.38 mmol) at 0° C. The reaction mixture was stirred at room temperature for 12 h. The reaction mixture was quenched with methanol (20 mL) at 10° C. and concentrated to afford N-{4-hydroxy-2-[3-(trifluoromethyl)phenyl]butan-2-yl}-2-methylpropane-2-sulfinamide (4.0 g) as a colourless gum.

MS: m/z 338 (M+1).

Step 5: Preparation of 3-[(2-methylpropane-2-sulfinyl)amino]-3-[3-(trifluoromethyl)phenyl]butyl methanesulfonate

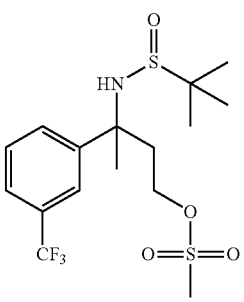 [SMILES: CC(CCOS(C)(=O)=O)(NS(=O)C(C)(C)C)c1cccc(C(F)(F)F)c1]

To a suspension of N-{4-hydroxy-2-[3-(trifluoromethyl)phenyl]butan-2-yl}-2-methylpropane-2-sulfinamide (from step 4) (5.0 g, 14.81 mmol) in dichloromethane (20 mL) was added triethylamine (1.5 g, 14.82 mmol) and methanesulphonyl chloride (1.6 g, 14.81 mmol) at 0° C. for 2 h. The reaction mass was added to ice cooled water and extracted with dichloromethane (3×20 mL). The combined organic extracts were dried over anhydrous sodium sulphate and evaporated to dryness to afford 3-[(2-methylpropane-2-sulfinyl)amino]-3-[3-(trifluoromethyl)phenyl]butyl methanesulfonate (5.5 g) as a colourless gum.

$^1$H NMR (400 MHz, DMSO-d$_6$) δ 7.79 (d, 2H, J=9.60 Hz), 7.66-7.58 (m, 2H), 5.58 (s, 1H), 4.14 (m, 2H), 3.09 (s, 3H), 2.38 (m, 2H), 1.70 (s, 3H), 1.15 (s, 9H);

MS: m/z 416.1 (M+1).

Step 6: Preparation of N-{4-azido-2-[3-(trifluoromethyl)phenyl]butan-2-yl}-2-methylpropane-2-sulfinamide

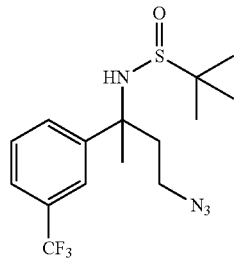 [SMILES: CC(CCN=[N+]=[N-])(NS(=O)C(C)(C)C)c1cccc(C(F)(F)F)c1]

A mixture of 3-[(2-methylpropane-2-sulfinyl)amino]-3-[3-(trifluoromethyl)phenyl]butyl methanesulfonate (from step 5) (5.3 g, 12.75 mmol) and sodium azide (0.82 g, 12.75 mmol) in N,N-dimethylformamide (150 mL) was stirred at 80° C. for 6 h. The reaction mixture was added to ice cooled water and extracted with ethyl acetate (3×20 mL). The combined organic extracts were dried over anhydrous sodium sulphate and evaporated to dryness to afford N-{4-azido-2-[3-(trifluoromethyl)phenyl]butan-2-yl}-2-methylpropane-2-sulfinamide (4.5 g) as a brownish gum.

$^1$H NMR (400 MHz, DMSO-$d_6$) δ 7.77 (d, 2H, J=8.00 Hz), 7.62-7.56 (m, 2H), 5.53 (s, 1H) 3.21 (m, 2H), 2.21 (m, 2H), 1.69 (s, 3H), 1.20 (s, 9H);

MS: m/z 363 (M+1);

IR: 2095.7 cm$^{-1}$.

Step 7: Preparation of N-{4-amino-2-[3-(trifluoromethyl)phenyl]butan-2-yl}-2-methylpropane-2-sulfinamide

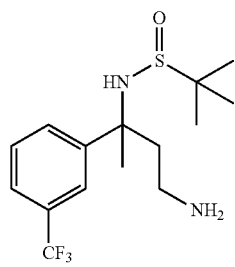 [SMILES: CC(CCN)(NS(=O)C(C)(C)C)c1cccc(C(F)(F)F)c1]

To a suspension of N-{4-azido-2-[3-(trifluoromethyl)phenyl]butan-2-yl}-2-methylpropane-2-sulfinamide (from step 6) (2.7 g, 7.44 mmol) in methanol (200 ml) was added Pd/C (20% w/w) (0.54 g) and the mixture was hydrogenated (under balloon pressure) at room temperature for 24 h. The reaction mixture was filtered through a celite bed, evaporated to remove the methanol to afford N-{4-amino-2-[3-(trifluoromethyl)phenyl]butan-2-yl}-2-methylpropane-2-sulfinamide (1.0 g) as a gum.

$^1$H NMR (400 MHz, DMSO-$d_6$) δ 7.79 (s, 1H), 7.75 (d, 1H, J=7.20 Hz), 7.63-7.57 (m, 2H), 6.59 (s, 1H), 4.10 (s, 2H), 2.72-2.67 (m, 2H), 2.10-2.03 (m, 1H), 1.91-1.84 (m, 1H), 1.61 (s, 3H), 1.15 (s, 9H);

MS: m/z 337.1 (M+1).

Step 8: Preparation of N-{3-[(2-methylpropane-2-sulfinyl)amino]-3-[3-(trifluoromethyl)phenyl]butyl}acetamide

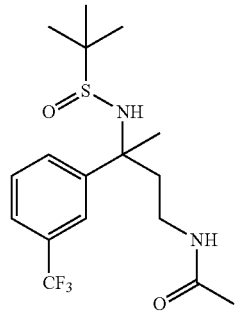 [SMILES: CC(=O)NCCC(C)(NS(=O)C(C)(C)C)c1cccc(C(F)(F)F)c1]

To a suspension of N-{4-amino-2-[3-(trifluoromethyl)phenyl]butan-2-yl}-2-methylpropane-2-sulfinamide (from step 7) (1.0 g, 2.97 mmol) in dichloromethane was added acetic anhydride (0.36 g, 3.56 mmol) at 28° C. and stirred for 4 h. The reaction mixture was concentrated to afford a crude product (0.9 g) as a gum, which was purified by silica gel (60-120 mesh) column chromatography eluting with 4% methanol in chloroform to afford N-{3-[(2-methylpropane-2-sulfinyl)amino]-3-[3-(trifluoromethyl)phenyl]butyl}acetamide (0.7 g) as a colourless gum.

MS: m/z 379.1 (M+1).

Step 9: Preparation of N-{3-amino-3-[3-(trifluoromethyl)phenyl]butyl}acetamide hydrochloride

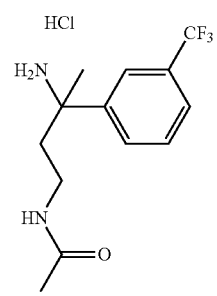 [SMILES: Cl ; CC(=O)NCCC(C)(N)c1cccc(C(F)(F)F)c1]

To a suspension of N-{3-[(2-methylpropane-2-sulfinyl)amino]-3-[3-(trifluoromethyl)phenyl]butyl}acetamide (from step 8) (0.7 g, 1.84 mmol) in dichloromethane (15 mL), cooled at 0° C., was added HCl 4 M solution in dioxane (3.5 ml) and the mixture was stirred at room temperature for 2 h. The reaction mixture was evaporated to dryness to afford N-{3-amino-3-[3-(trifluoromethyl)phenyl]butyl}acetamide hydrochloride (0.5 g) as an off-white solid.

MS: m/z 275.1 (M+1).

Step 10: Preparation of N-{3-isothiocyanato-3-[3-(trifluoromethyl)phenyl]butyl}acetamide

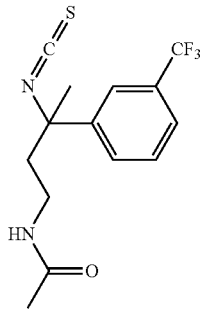

To a suspension of N-{3-amino-3-[3-(trifluoromethyl)phenyl]butyl}acetamide hydrochloride (from step 9) (0.5 g, 1.82 mmol) in dichloromethane (10 mL), cooled at 0° C., was added thiophosgene (0.20 mL, d=1.5 g/mL, 2.73 mmol) followed by 10% aqueous sodium bicarbonate solution (10 mL). The reaction mixture was stirred at room temperature for 1 h, diluted with 10% aqueous sodium bicarbonate solution (20 mL) and extracted with dichloromethane (3×25 mL). The combined organic extracts were dried over anhydrous sodium sulphate and evaporated to dryness to afford N-{3-isothiocyanato-3-[3-(trifluoromethyl)phenyl]butyl}acetamide (0.5 g) as a red gum.

MS: m/z 317.1 (M+1).

Step 11: Preparation of N-(3-{[(2-aminophenyl)carbamothioyl]amino}-3-[3-(trifluoromethyl)phenyl]butyl)acetamide

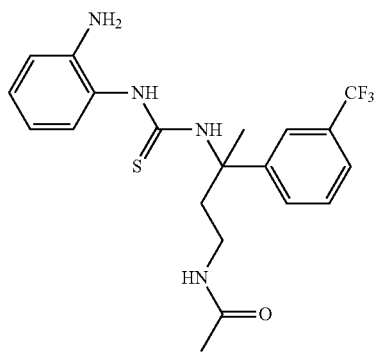 [SMILES: CC(=O)NCCC(C)(NC(=S)Nc1ccccc1N)c1cccc(C(F)(F)F)c1]

A mixture of N-{3-isothiocyanato-3-[3-(trifluoromethyl)phenyl]butyl}acetamide (from step 10) (0.3 g, 0.94 mmol) and 1,2-phenylene diamine (commercially available) (0.103 g, 0.95 mmol) in dichloromethane (20 mL) was stirred at room temperature for 12 h. The reaction mixture was concentrated to afford a crude product (0.4 g) as a gum. This was purified by silica gel (60-120 mesh) column chromatography eluting with 5% methanol in chloroform to afford N-(3-{[(2-aminophenyl)carbamothioyl]amino}-3-[3-(trifluoromethyl)phenyl]butyl)acetamide (0.160 g) as a brownish gum.

$^1$H NMR (400 MHz, DMSO-$d_6$:$D_2O$) δ 7.74 (s, 1H), 7.61-7.59 (m, 2H), 7.54 (s, 2H), 7.01-6.94 (m, 1H), 6.74 (d, 1H, J=8.00 Hz), 6.57-6.54 (m, 1H), 3.10-2.98 (m, 2H), 2.12 (m, 1H), 1.63-1.73 (m, 1H), 1.75 (s, 3H), 1.24 (s, 3H); MS: m/z 425.4 (M+1).

Example 21, Step 12: Preparation of N-{3-[(1H-1,3-benzodiazol-2-yl)amino]-3-[3-(trifluoromethyl)phenyl]butyl}acetamide

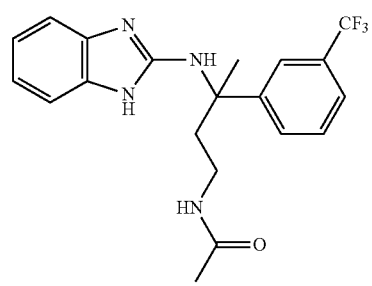 [SMILES: CC(=O)NCCC(C)(Nc1nc2ccccc2[nH]1)c1cccc(C(F)(F)F)c1]

To a solution of N-(3-{[(2-aminophenyl)carbamothioyl]amino}-3-[3-(trifluoromethyl)phenyl]butyl)acetamide (from step 11) (0.160 g, 0.37 mmol) in methanol (20 mL) was added iodoacetic acid (84.0 mg, 0.45 mmol) and the mixture was refluxed for 2 h. The reaction mixture was evaporated to afford the crude product (0.11 g) which was purified by silica gel (60-120 mesh) column chromatography using 5% methanol in chloroform as eluent to afford N-{3-[(1H-1,3-benzodiazol-2-yl)amino]-3-[3-(trifluoromethyl)phenyl]butyl}acetamide (65.0 mg) as an off-white solid.

$^1$H NMR (400 MHz, AcOH-$d_4$) δ 7.85 (d, J=6.40 Hz, 2H), 7.69-7.59 (m, 2H), 7.32 (dd, J=3.20, 6.00 Hz, 2H), 7.22 (dd, J=3.20, 6.40 Hz, 2H), 3.41-3.37 (m, 2H), 2.59-2.52 (m, 1H), 2.44-2.37 (m, 1H), 1.93 (s, 3H), 1.85 (s, 3H); MS: m/z 391.1 (M+1).

Example 22: Preparation of N-{3-[(1H-1,3-benzodiazol-2-yl)amino]-3-[3-(trifluoromethoxy)phenyl]propyl}acetamide

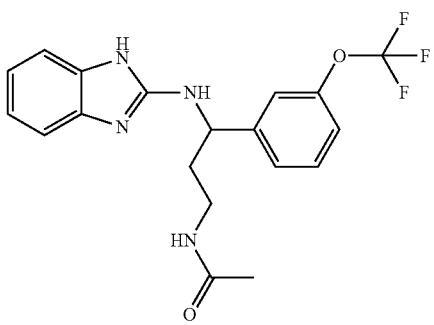 [SMILES: CC(=O)NCCC(Nc1nc2ccccc2[nH]1)c1cccc(OC(F)(F)F)c1]

Step 1: Preparation of 3-amino-3-[3-(trifluoromethoxy)phenyl]propanoic acid

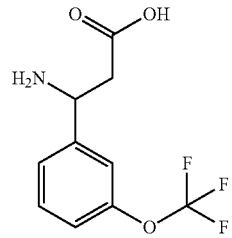 [SMILES: NC(CC(=O)O)c1cccc(OC(F)(F)F)c1]

A mixture of malonic acid (32.8 g, 316 mmol), ammonium formate (33.2 g, 526 mmol) and 3-(trifluoromethoxy)benzaldehyde (commercially available) (50 g, 263 mmol) in ethanol (500 mL) was refluxed for 12 h. The reaction mixture was evaporated to remove ethanol and the residue was triturated with acetone (5×500 mL) and the residual solid was filtered and dried to afford 3-amino-3-[3-(trifluoromethoxy)phenyl]propanoic acid (28 g) as white solid. $^1$HNMR (400 MHz, DMSO-$d_6$) δ 7.46 (dd, 3H, J=11.2, 7.6 Hz), 7.26 (d, 1H, J=8.0 Hz), 4.30 (t, 1H, J=7.6 Hz), 2.37 (d, 2H, J=1.6 Hz);

MS: m/z 250.1 (M+1).

Step 2: Preparation of 3-{[(tert-butoxy)carbonyl]amino}-3-[3-(trifluoromethoxy)phenyl] propanoic acid

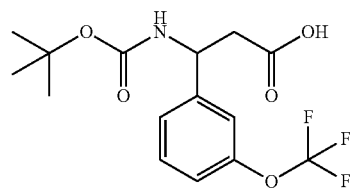 [SMILES: CC(C)(C)OC(=O)NC(CC(=O)O)c1cccc(OC(F)(F)F)c1]

To a stirred suspension of 3-amino-3-[3-(trifluoromethoxy)phenyl]propanoic acid (from step 1) (10 g, 40.00 mmol) in t-BuOH (100 mL) was added NaOH (1.52 g, 39 mmol) solution with water (100 mL) at 0° C. and it was stirred for 10 min. Then Boc-anhydride (12.7 g, 59.0 mmol) was added portion wise and the mixture was stirred at ambient temperature for 18 h. The reaction mixture was concentrated and the pH was adjusted to pH=5-6 with citric acid and extracted with ethyl acetate (3×100 mL). The combined organic extracts were dried over anhydrous sodium sulphate and evaporated to afford 3-{[(tert-butoxy)carbonyl]amino}-3-[3-(trifluoromethoxy)phenyl]propanoic acid (13 g) as a colourless gum which was used in the next step without further purification.

MS: m/z 350.1 (M+1).

Step 3: Preparation of tert-butyl N-{3-hydroxy-1-[3-(trifluoromethoxy)phenyl]propyl} carbamate

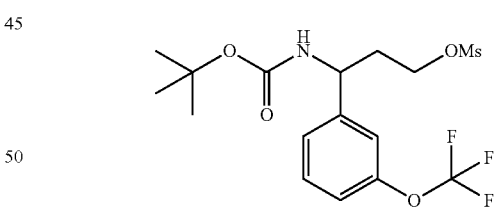

To a suspension of 3-{[(tert-butoxy)carbonyl]amino}-3-[3-(trifluoromethoxy)phenyl]propanoic acid (from step 2) (200 g, 573 mmol) in THF (1000 mL) was added TEA (238 mL, d=0.726 g/cm$^3$, 1718 mmol) and isobutyl chloroformate (117.30 g, 859 mmol) at 0° C. and stirred at 0° C. for 4 h. The solid that formed was filter off at 0° C. and the residue was washed with THF (50 mL). The combined filtrate was added to a cooled mixture of NaBH$_4$ (43.32 g, 1145.12 mmol) in water (200 mL). The reaction mixture was slowly warmed to ambient temperature and stirred for 30 h. The reaction was quenched with ice cold water (1000 mL) and extracted with ethyl acetate (2×1000 mL) and the combined organic layer was washed with brine (250 mL), dried over Na$_2$SO$_4$, filtered and concentrated to afford a liquid (300 g). This was purified by column chromatography using 35% ethyl acetate in petroleum ether as eluent, to afford tert-butyl N-{3-hydroxy-1-[3-(trifluoromethoxy)phenyl]propyl}carbamate (200 g) as pale yellow liquid.

$^1$H NMR (400 MHz, DMSO-$d_6$) δ 7.47 (t, 2H, J=8.0 Hz), 7.29 (d, 1H, J=8.0 Hz), 7.21 (t, 2H, J=8.0 Hz), 4.64 (dd, 1H, J=14.0, 7.2 Hz), 4.53 (t, 1H, J=4.8 Hz), 3.39 (dd, 1H, J=10.4, 5.2 Hz), 3.29 (dd, 1H, J=10.8, 5.2 Hz), 1.80 (dd, 1H, J=11.2, 5.6 Hz), 1.70 (dd, 1H, J=13.2, 6.8 Hz), 1.35 (s, 9H); MS: m/z 236.1 [(M+1)-Boc]

Step 4: Preparation of tert-butyl N-[3-(methanesulfonyloxy)-1-[3-(trifluoromethoxy)phenyl]propyl] carbamate To a solution of tert-butyl N-{3-hydroxy-1-[3-(trifluoromethoxy)phenyl]propyl}carbamate (10 g, 30.0 mmol) (from step 3) in dichloromethane (100 mL), was added TEA (6.8 ml, d=0.726 g/cm$^3$, 48.87 mmol) at 0° C., followed by mesyl chloride (5 mL, d=1.48 g/cm$^3$, 64.6 mmol). The reaction mixture was allowed to attain ambient temperature and stirred for 2 h. The reaction mixture was diluted with water (100 mL) and extracted with dichloromethane (2×100 mL) and evaporated to afford tert-butyl N-[3-(methanesulfonyloxy)-1-[3-(trifluoromethoxy)phenyl]propyl]carbamate (12.0 g) as brown liquid, which was used in the next step without further purification.

$^1$H NMR (400 MHz, DMSO-$d_6$) δ 7.60 (d, 1H, J=8.4 Hz), 7.49 (t, 1H, J=8.0 Hz), 7.34 (d, 1H, J=7.6 Hz), 7.26 (t, 2H,

J=8.0 Hz), 4.66 (t, 1H, J=7.6 Hz), 4.22 (dd, 1H, J=6.4, 12.0 Hz), 4.14 (dd, 1H, J=10.0, 4.8 Hz), 3.16 (s, 3H), 2.04 (dd, 2H, J=9.6, 3.2 Hz), 1.36 (s, 9H);
MS: m/z 313.1 [(M+1)-Boc].

Step 5: Preparation of tert-butyl N-{3-azido-1-[3-(trifluoromethoxy)phenyl]propyl} carbamate

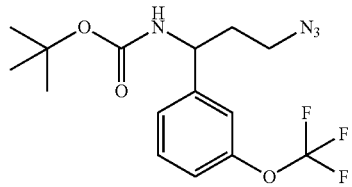 [SMILES: CC(C)(C)OC(=O)NC(CCN=[N+]=[N-])c1cccc(OC(F)(F)F)c1]

To a suspension of tert-butyl N-[3-(methanesulfonyloxy)-1-[3-(trifluoromethoxy)phenyl]propyl]carbamate (from step 4) (20 g, 48.0 mmol) in DMF (50 mL) was added sodium azide (7.8 g, 120 mmol) and the mixture was stirred at 50° C. for 5 h. The reaction mixture was concentrated to remove DMF and diluted with water (100 mL). The aqueous layer was extracted with ethyl acetate (3×100 mL). Combined organic layer was dried over sodium sulphate, filtered and concentrated to afford a crude product (20 g) as a gum, which was purified by silica gel (230-400 mesh) column chromatography eluting with 3% methanol in DCM to afford tert-butyl N-{3-azido-1-[3-(trifluoromethoxy)phenyl]propyl}carbamate (13 g) as an off-white solid.
$^1$H NMR (400 MHz, DMSO-$d_6$) δ 7.47 (t, 1H, J=8.0 Hz), 7.33 (d, 2H, J=8.0 Hz), 7.25 (t, 2H, J=8.0 Hz), 4.63 (dd, 1H, J=14.2, 8.8 Hz), 3.34 (dd, 2H, J=12.2, 6.0 Hz), 1.85 (dd, 2H, J=13.4, 7.2 Hz), 1.37 (s, 9H); MS: m/z 260.1 [(M+1)-Boc].

Step 6: Preparation of 3-azido-1-[3-(trifluoromethoxy)phenyl]propan-1-amine hydrochloride

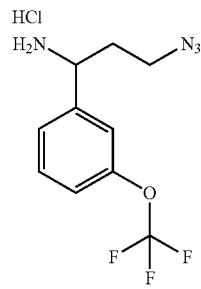

To a suspension of tert-butyl tert-butyl N-{3-azido-1-[3-(trifluoromethoxy)phenyl]propyl}carbamate (from step 5) (13 g, 36.0 mmol) in dioxane (5 mL) cooled to 0° C. was added HCl in Dioxane (4M, 50 mL). The mixture was then warmed to ambient temperature and stirred for 1 h. The reaction mixture was concentrated to afford 3-azido-1-[3-(trifluoromethoxy)phenyl]propan-1-amine hydrochloride (10 g) as a white solid.

$^1$H NMR (400 MHz, DMSO-$d_6$/$D_2$O) δ 7.6-7.54 (m, 3H), 7.41 (d, 1H, J=1.2 Hz), 4.41 (dd, 1H, J=8.8, 5.6 Hz), 3.36 (dd, 1H, J=7.2, 10.8 Hz), 3.20 (dd, 1H, J=6.4, 13.6 Hz), 2.22 (dd, 1H, J=7.6, 14.0 Hz), 2.05 (t, 1H, J=8.8 Hz); MS: m/z 261.1 (M+1).

Step 7: Preparation of 1-(3-azido-1-isothiocyanato-propyl)-3-(trifluoromethoxy)benzene

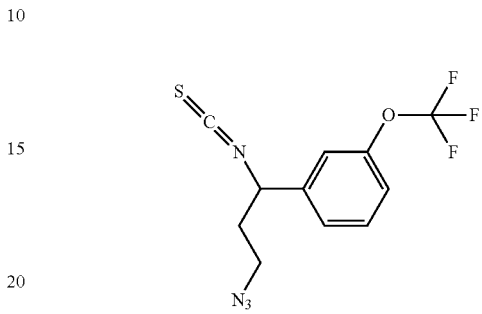

To a suspension of 3-azido-1-[3-(trifluoromethoxy)phenyl]propan-1-amine hydrochloride (from step 6) (10 g, 34.0 mmol) in dichloromethane (150 mL), cooled at 0° C., was added thiophosgene (3.8 mL, d=1.5 g/cm$^3$, 51.0 mmol) followed by 10% aqueous sodium bicarbonate solution (50 mL). The reaction mixture was then stirred at ambient temperature. After 1 h, the reaction mixture was diluted with 10% aqueous sodium bicarbonate solution (50 mL) and extracted with dichloromethane (2×100 mL). The combined organic extracts were dried over anhydrous sodium sulphate and evaporated to dryness to afford the product 1-(3-azido-1-isothiocyanatopropyl)-3-(trifluoromethoxy)benzene (10 g) as a red gum which was used in the next step without further purification.
$^1$H NMR (400 MHz, DMSO-$d_6$) δ 7.60 (t, 1H, J=1.2 Hz), 7.50 (s, 1H), 7.39 (d, 1H, J=8.0 Hz), 7.31 (s, 1H), 5.33 (dd, 1H, J=5.2, 9.2 Hz), 3.47 (t, 2H, J=6.80 Hz), 2.22-2.19 (m, 1H) 2.17-2.09 (m, 1H);

Step 8: Preparation of 1-(2-aminophenyl)-3-{3-azido-1-[3-(trifluoromethoxy)phenyl]propyl}thiourea

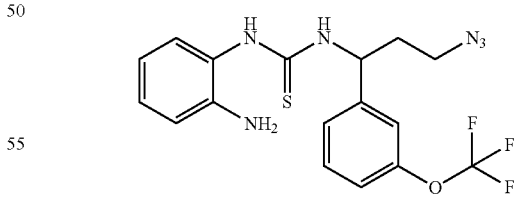

A mixture of 1-(3-azido-1-isothiocyanatopropyl)-3-(trifluoromethoxy)benzene (from step 7) (10 g, 33.0 mmol) and benzene-1, 2-diamine (3 g, 28.0 mmol) in dichloromethane (100 mL) was stirred at ambient temperature for 12 h. The reaction mixture was concentrated to afford 1-(2-aminophenyl)-3-{3-azido-1-[3-(trifluoromethoxy)phenyl]propyl}thiourea (13 g) as a brownish gum, which was used in the next step without further purification.
MS: m/z 411.1 (M+1).

Step 9: Preparation of N-{3-azido-1-[3-(trifluoromethoxy)phenyl]propyl}-1H-1,3-benzodiazol-2-amine

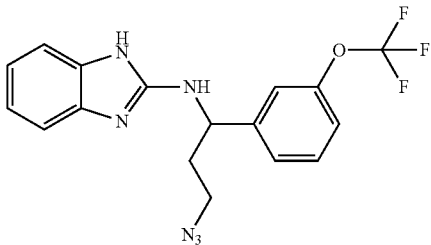 [SMILES: [N-]=[N+]=NCCC(Nc1nc2ccccc2[nH]1)c1cccc(OC(F)(F)F)c1]

To a solution of 1-(2-aminophenyl)-3-{3-azido-1-[3-(trifluoromethoxy)phenyl]propyl}thiourea (from step 8) (8 g, 19.0 mmol) in methanol (80 mL) was added iodoacetic acid (3.6 g, 19.0 mmol) and the mixture was refluxed for 2 h. The reaction mixture was evaporated to afford the crude product (9 g) which was purified by silica gel (230-400 mesh) column chromatography using 5% methanol in DCM as eluent to afford N-{3-azido-1-[3-(trifluoromethoxy)phenyl]propyl}-1H-1,3-benzodiazol-2-amine (6.5 g) as an off-brown solid.

$^1$H NMR (400 MHz, DMSO-d$_6$) δ 7.47-7.42 (m, 3H), 7.33 (dd, 2H, J=14.6, 8.0 Hz), 7.20 (dd, 1H, J=2.8, 2.6 Hz), 7.10 (t, 2H, J=4.4 Hz), 6.84 (dd, 2H, J=5.6, 3.2 Hz), 5.02-4.98 (m, 1H), 3.46-3.39 (m, 2H), 2.10 (dd, 1H, J=9.8, 8.0 Hz), 1.99 (dd, 1H, J=8.6, 3.6 Hz),

MS: m/z 377.1 (M+1).

Step 10: Preparation of N1-(1H-1,3-benzodiazol-2-yl)-1-[3-(trifluoromethoxy)phenyl]propane-1,3-diamine hydrochloride

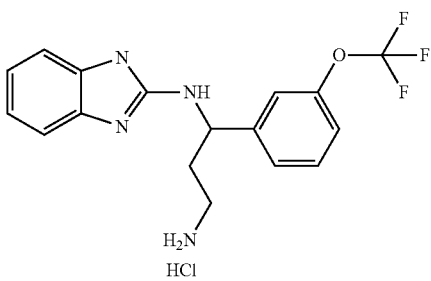 [SMILES: NCCC(Nc1nc2ccccc2[nH]1)c1cccc(OC(F)(F)F)c1 ; Cl]

To a solution of N-{3-azido-1-[3-(trifluoromethoxy)phenyl]propyl}-1H-1,3-benzodiazol-2-amine (from step 9) (7 g, 18.68 mmol) in methanol (200 mL) was added Pd/C (10%) (2 g). The reaction mixture was placed in an autoclave under hydrogen atmosphere at 71.12 Psi pressure for 15 h. The reaction mixture was filtered through a celite bed, washed with methanol (1500 mL) and 2 M con. HCl was added to the filtrate and evaporated to afford N1-(1H-1,3-benzodiazol-2-yl)-1-[3-(trifluoromethoxy)phenyl]propane-1,3-diamine hydrochloride (4 g) as brown solid, which was used in the next step without further purification.

$^1$H NMR (400 MHz, DMSO-d$_6$) δ 7.99 (d, 1H, J=8.0 Hz), 7.67 (d, 1H, J=7.2 Hz), 7.49-745 (m, 3H), 7.25 (d, 3H, J=5.6 Hz), 5.53 (s, 1H), 3.49 (d, 2H, J=15.2 Hz), 2.63 (d, 1H, J=16.4 Hz), 2.50 (d, 1H, J=31.2 Hz); MS: m/z 351.1 (M+1).

Example 22, Step 11: Preparation of N-{3-[(1H-1,3-benzodiazol-2-yl)amino]-3-[3-(trifluoromethoxy)phenyl]propyl}acetamide

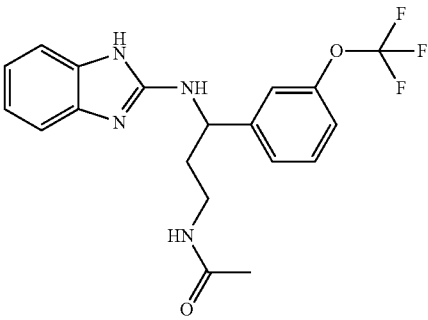 [SMILES: CC(=O)NCCC(Nc1nc2ccccc2[nH]1)c1cccc(OC(F)(F)F)c1]

To a suspension of N1-(1H-1,3-benzodiazol-2-yl)-1-[3-(trifluoromethoxy)phenyl]propane-1,3-diamine hydrochloride (from step 10) (1.0 g, 3.0 mmol) in DCM (20 mL) cooled to 0° C. was added triethylamine (0.71 mL, 5.0 mmol) and acetyl chloride (0.18 mL, 3.0 mmol). The mixture was then warmed to ambient temperature and stirred for 1 h. The reaction mixture was quenched with water (25 mL), extract with DCM (3×50 mL). The combined organic layer was dried over sodium sulphate, filtered and concentrated to afford the product (1.2 g) as a gum, which was purified by silica gel (230-400 mesh) column chromatography eluting with 7% methanol in DCM to afford N-{3-[(1H-1,3-benzodiazol-2-yl)amino]-3-[(trifluoromethoxy)phenyl]propyl}acetamideas (0.6 g) as an off-white solid.

$^1$H NMR (400 MHz, DMSO-d$_6$) δ 7.50-7.45 (m, 3H), 7.38 (dd, 2H, J=6.0, 3.2 Hz), 7.26-7.22 (m, 3H), 4.97 (dd, 1H, J=9.2, 4.8 Hz), 3.50 (dd, 2H, J=11.0, 6.0 Hz), 2.29-2.21 (m, 2H), 2.09 (s, 3H);

MS: m/z 393.1 (M+1).

The above product was resolved into its enantiomers by Chiral SFC (Condition: Chiralpak OXH 20 mM Ammonia in IPA Co-Solvent: 30% (flow rate: 3 ml/min).

Example 22a: (−)-N-{3-[(1H-1,3-benzodiazol-2-yl)amino]-3-[3-(trifluoromethoxy)phenyl]propyl}acetamide The (−) enantiomer was the first to elute off the column.

$^1$H NMR (400 MHz, AcOH-d$_4$) δ 7.50 (d, 1H, J=3.2 Hz), 7.47 (s, 1H), 7.44 (s, 1H) 7.37 (t, 2H, J=3.2 Hz), 7.23 (dd, 3H, J=6.0, 2.0 Hz), 4.96 (dd, 1H, J=8.80, 4.80 Hz), 3.49 (dd, 2H, J=11.6, 6.0 Hz), 2.21 (dd, 2H, J=17.2, 6.4 Hz), 2.02 (s, 3H);

MS: m/z 393.2 (M+1);

$[α]_D^{27.6}$=(−) 95.05° (MeOH, c=0.10).

Example 22b: (+)-N-{3-[(1H-1,3-benzodiazol-2-yl)amino]-3-[3-(trifluoromethoxy)phenyl]propyl}acetamide The (+) enantiomer was the second to elute off the column.

$^1$H NMR (400 MHz, AcOH-d$_4$) δ 7.50 (d, 1H, J=5.2 Hz), 7.47 (s, 1H), 7.44 (s, 1H), 7.37 (dd, 2H, J=5.8, 3.2 Hz), 7.23 (dd, 3H, J=5.8, 3.2 Hz), 4.95 (t, 1H, J=5.2 Hz), 3.48 (t, 2H, J=6.4 Hz), 2.20 (t, 2H, J=5.2 Hz), 2.02 (s, 3H);

MS: m/z 393.2 (M+1);

$[α]_D^{27.6}$=(+) 74.77° (MeOH, c=0.10).

We claim:

1. A compound of formula (I)

wherein
- n is an integer selected from 1, 2, 3, and 4;
- when n is 1, 2, 3 or 4, the methylene, ethylene, propylene or butylene chain is optionally substituted with a group selected from $C_{1-6}$ alkyl optionally substituted with a halogen; and halogen;
- m is an integer selected from 0 and 1;
- R1-R4 are independently a group selected from H, halogen, CN, $C_{1-6}$ alkyl, $C_{1-6}$ alkylene-OH, $C_{1-6}$ alkoxy, $OCF_3$, $C_{1-6}$ alkylene-O—$C_{1-6}$ alkyl, $C_{1-6}$ alkylene-S—$C_{1-6}$ alkyl, $C_{3-7}$cycloalkyl, $NR^cC(=O)$—$C_{1-6}$alkyl wherein $R^c$ is selected from H and $C_{1-6}$ alkyl, and $C_{1-6}$ alkylene-$NR^aR^b$, wherein $R^a$ and $R^b$ are independently a group selected from H, $C_{1-6}$ alkyl, $C_{1-6}$ alkylene-OH, $C_{1-6}$alkylene-O—$C_{1-6}$ alkyl, $C(=O)$—$C_{1-6}$alkyl, $C(=O)$—$C_{1-6}$alkoxy, $C(=O)$—$C_{1-6}$alkyl-CN, $C(=O)$—$C_{1-6}$alkyl-OH, $C(=O)$—$C_{1-6}$alkylene-S—$C_{1-6}$ alkyl, $C(=O)$—O—$C_{1-6}$alkylene-O—$C_{1-6}$ alkyl, $C(=O)$—O—$C_{1-6}$alkyl-CN, $C(=O)$—O—$C_{1-6}$alkyl-OH, $C(=O)$—O—$C_{1-6}$ alkylene-S—$C_{1-6}$ alkyl, $C(=O)$—$NHC_{1-6}$ alkyl, $C(=O)$—$NHC_{1-6}$ alkylene-O—$C_{1-6}$ alkyl, $C(=O)$—$NHC_{1-6}$alkylene-S—$C_{1-6}$ alkyl, $C(=O)$—$NHC_{1-6}$alkyl-CN, $C(=O)$—$NHC_{1-6}$alkyl-OH, $C(=O)$—$N(C_{1-6}alkyl)_2$, $SO_2$—$C_{1-6}$ alkyl, $SO_2$—$C_{1-6}$ alkylene-O—$C_{1-6}$ alkyl, $SO_2$—$C_{1-6}$ alkylene-S—$C_{1-6}$ alkyl, $SO_2$—$C_{1-6}$alkyl-CN, $SO_2$—$C_{1-6}$alkyl-OH, and $SO_2$—$C_{1-6}$alkyl-$N(C_{1-6}alkyl)_2$;
- R5-R9 are independently a group selected from H, halogen, $CH_2F$, $CHF_2$, $CF_3$, CN, $C_{1-6}$ alkyl, $C_{1-6}$alkylene-OH, OH, $C_{1-6}$alkoxy, $C_{1-6}$ alkylene-O—$C_{1-6}$ alkyl, $C_{1-6}$alkylene-S—$C_{1-6}$ alkyl, $C_{3-7}$cycloalkyl, $C(=O)$—O—$C_{1-6}$ alkyl, S—$C_{1-6}$ alkyl, $SCF_3$, $OCF_3$, $OCF_2H$, $OCFH_2$, $OC_{3-7}$cycloalkyl, $SC_{3-7}$cycloalkyl;
- R10 is a group selected from H, $C_{1-6}$ alkyl, $C_{1-6}$alkyl substituted with 1 to 3 Fluorine atoms, and $C_{3-4}$cycloalkyl;
- R11 is a group selected from $C_{1-6}$ alkyl, $C_{1-6}$ alkylene-OH; $C_{1-6}$ alkylene-O—$C_{1-6}$ alkyl, wherein $C_{1-6}$ alkylene is optionally substituted with a phenyl, and wherein $C_{1-6}$ alkyl is optionally substituted with a halogen; $C_{1-6}$ alkylene-S—$C_{1-6}$ alkyl; $C_{1-6}$ alkylene-CN; $C_{1-6}$alkylene-$C(=O)$—O—$C_{1-6}$ alkyl; $C_{1-6}$alkylene-O—$C(=O)$—NH—$C_{1-6}$ alkyl; $C_{3-7}$cycloalkyl; an aryl optionally substituted with a group selected from $C_{1-6}$ alkyl, halogen, CN, OH, and $C_{1-6}$ alkylene-OH; an aliphatic heterocycle optionally substituted with a group selected from $C_{1-6}$ alkyl, OH, and $C_{1-6}$ alkylene-OH; and a heteroaryl optionally substituted with a group selected from $C_{1-6}$ alkyl, halogen, CN, OH, and $C_{1-6}$ alkylene-OH;
- R12 is a group selected from H, and $C_{1-6}$ alkyl; or
- R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, wherein the monocyclic aliphatic heterocycle is optionally substituted at the two to six further carbon atoms with a group selected from $C_{1-6}$ alkyl; oxo; OH; $C_{1-6}$ alkylene-OH; $C(=O)$—$C_{1-6}$ alkyl; $C(=O)$—O—$C_{1-6}$ alkyl; $SO_2$—$C_{1-6}$ alkyl; $NR^kR^l$, wherein $R^k$ and $R^l$ are independently a group selected from H and $C_{1-6}$ alkyl; and $C_{1-6}$ alkylene-$NR^mR^n$, wherein $R^m$ and $R^n$ are independently a group selected from H and $C_{1-6}$ alkyl; or
- a pharmaceutically acceptable salt thereof.

2. The compound of claim 1, wherein m is 0.

3. The compound of claim 1, wherein n is selected from 1, 2 or 3.

4. The compound of claim 1, wherein n is selected from 2 and a $C_{1-6}$ alkyl is attached to the ethylene chain.

5. The compound of claim 1, wherein R1 is selected from H and $C_{1-6}$ alkylene-OH.

6. The compound of claim 1, wherein R1 is selected from H and $CH_2OH$.

7. The compound of claim 1, wherein R2 is selected from H and halogen.

8. The compound of claim 1, wherein R2 is selected from H and F.

9. The compound of claim 1, wherein R3 is selected from H and halogen.

10. The compound of claim 1, wherein R3 is selected from H.

11. The compound of claim 1, wherein R4 is selected from H and $C_{1-6}$ alkylene-OH.

12. The compound of claim 1, wherein R4 is selected from H.

13. The compound of claim 1, wherein R5 is selected from H.

14. The compound of claim 1, wherein R6 is selected from $CH_2F$, $CHF_2$, $CF_3$, and $OCF_3$.

15. The compound of claim 1, wherein R6 is selected from $CF_3$ and $OCF_3$.

16. The compound of claim 1, wherein R7 is selected from H.

17. The compound of claim 1, wherein R8 is selected from H, $CH_2F$, $CHF_2$, $CF_3$, and $OCF_3$.

18. The compound of claim 1, wherein R8 is selected from H.

19. The compound of claim 1, wherein R9 is selected from H.

20. The compound of claim 1, wherein R10 is a group selected from H and $C_{1-6}$ alkyl.

21. The compound of claim 1, wherein R10 is selected from H and $CH_3$.

22. The compound of claim 1, wherein R11 is selected from $C_{1-6}$ alkyl, $C_{1-6}$ alkylene-OH; $C_{1-6}$alkylene-O—$C_{1-6}$ alkyl; $C_{3-7}$cycloalkyl; an aryl optionally substituted with a group selected from halogen and CN; an aliphatic heterocycle; and a heteroaryl.

23. The compound of claim 1, wherein R11 is selected from $CH_3$, $CH_2CH_3$, $CH_2$—OH; $CH_2O$—$CH_3$; $C_{3-4}$cycloalkyl; a phenyl substituted with a group selected from fluoro and CN; a tetrahydropyranyl; an oxazolyl; an oxadiazolyl; a pyrimidyl; and a pyridyl.

24. The compound of claim 1, wherein R12 is selected from H and $CH_3$.

25. The compound of claim 1, wherein R11 and R12 together with the nitrogen to which R12 is linked and the carbonyl to which R11 is linked form a monocyclic 4-8 membered aliphatic heterocycle containing the nitrogen to which R12 is linked and the carbonyl to which R11 is linked and from two to six further carbon atoms, selected from a pyrrolidinyl-2-one.

26. The compound of claim 1, selected from:
N-{2-[(1H-1,3-benzodiazol-2-yl)amino]-2-[3-(trifluoromethyl)phenyl]ethyl}-1,2-oxazole-3-carboxamide,
N-{2-[(1H-1,3-benzodiazol-2-yl)amino]-2-[3-(trifluoromethyl)phenyl]ethyl}-cyclobutanecarboxamide,
N-{2-[(1H-1,3-benzodiazol-2-yl)amino]-2-[3-(trifluoromethyl)phenyl]ethyl}-cyclopropanecarboxamide,
N-{2-[(1H-1,3-benzodiazol-2-yl)amino]-2-[3-(trifluoromethyl)phenyl]ethyl}-1,2,4-oxadiazole-3-carboxamide,
N-{2-[(1H-1,3-benzodiazol-2-yl)amino]-2-[3-(trifluoromethyl)phenyl]ethyl}-pyrimidine-4-carboxamide,
N-{2-[(1H-1,3-benzodiazol-2-yl)amino]-2-[3-(trifluoromethyl)phenyl]ethyl}-pyridine-2-carboxamide,
N-{2-[(1H-1,3-benzodiazol-2-yl)amino]-2-[3-(trifluoromethyl)phenyl]ethyl}-3-cyanobenzamide,
N-{2-[(1H-1,3-benzodiazol-2-yl)amino]-2-[3-(trifluoromethyl)phenyl]ethyl}-oxane-4-carboxamide,
N-{2-[(1H-1,3-benzodiazol-2-yl)amino]-2-[3-(trifluoromethyl)phenyl]ethyl}-3-fluorobenz amide,
N-{2-[(1H-1,3-benzodiazol-2-yl)amino]-2-[3-(trifluoromethyl)phenyl]ethyl}-propanamide,
(−)-N-{2-[(1H-1,3-benzodiazol-2-yl)amino]-2-[3-(trifluoromethyl)phenyl]-ethyl}propanamide,
(+)-N-{2-[(1H-1,3-benzodiazol-2-yl)amino]-2-[3-(trifluoromethyl)phenyl]-ethyl}propanamide,
1-{2-[(1H-1,3-benzodiazol-2-yl)amino]-2-[3-(trifluoromethyl)phenyl]ethyl}-pyrrolidin-2-one,
N-[(2R)-2-[(1H-1,3-benzodiazol-2-yl)amino]-2-[3-(trifluoromethyl)phenyl]-ethyl]-2-methoxyacetamide,
N-[(2R)-2-[(1H-1,3-benzodiazol-2-yl)amino]-2-[3-(trifluoromethyl)phenyl]-ethyl]-2-hydroxyacetamide,
N-{3-[(1H-1,3-benzodiazol-2-yl)amino]-3-[3-(trifluoromethyl)phenyl]-propyl}acetamide,
(−)-N-{3-[(1H-1,3-benzodiazol-2-yl)amino]-3-[3-(trifluoromethyl)phenyl]-propyl}acetamide,
(+)-N-{3-[(1H-1,3-benzodiazol-2-yl)amino]-3-[3-(trifluoromethyl)phenyl]-propyl}acetamide,
N-(3-{[4-(hydroxymethyl)-1H-1,3-benzodiazol-2-yl]amino}-3-[3-(trifluoromethyl)phenyl]propyl)-1,2-oxazole-3-carboxamide,
N-{3-[(1H-1,3-benzodiazol-2-yl)amino]-3-[3-(trifluoromethyl)phenyl]-propyl}-2,2,2-trifluoroacetamide,
N-{4-[(1H-1,3-benzodiazol-2-yl)amino]-4-[3-(trifluoromethyl)phenyl]butan-2-yl}acetamide,
N-{3-[(1H-1,3-benzodiazol-2-yl)amino]-3-[3-(trifluoromethyl)phenyl]-propyl}-N-methylacetamide,
(−)-N-{3-[(1H-1,3-benzodiazol-2-yl)amino]-3-[3-(trifluoromethyl)phenyl]-propyl}-N-methylacetamide,
(+)-N-{3-[(1H-1,3-benzodiazol-2-yl)amino]-3-[3-(trifluoromethyl)phenyl]-propyl}-N-methylacetamide,
N-{4-[(1H-1,3-benzodiazol-2-yl)amino]-4-[3-(trifluoromethyl)phenyl]-butyl}acetamide,
(−)-N-{4-[(1H-1,3-benzodiazol-2-yl)amino]-4-[3-(trifluoromethyl)phenyl]-butyl}acetamide,
(+)-N-{4-[(1H-1,3-benzodiazol-2-yl)amino]-4-[3-(trifluoromethyl)phenyl]-butyl}acetamide,
N-{4-[(5-fluoro-1H-1,3-benzodiazol-2-yl)amino]-4-[3-(trifluoromethyl)-phenyl]-butyl}-acetamide,
N-{3-[(1H-1,3-benzodiazol-2-yl)amino]-3-[3-(trifluoromethyl)phenyl]-butyl}acetamide,
N-{3-[(1H-1,3-benzodiazol-2-yl)amino]-3-[3-(trifluoromethoxy)phenyl]-propyl}acetamide,
(−)-N-{3-[(1H-1,3-benzodiazol-2-yl)amino]-3-[3-(trifluoromethoxy)phenyl]-propyl}-acetamide, and
(+)-N-{3-[(1H-1,3-benzodiazol-2-yl)amino]-3-[3-(trifluoromethoxy)phenyl]-propyl}-acetamide, or
a pharmaceutically acceptable salt thereof.

27. A pharmaceutical composition comprising the compound of claim 1, and optionally a pharmaceutically acceptable additive.

28. A method for treatment of a cardiac disease, disorder or condition in a mammal, wherein a therapeutically effective amount of at least one compound according to claim 1 is administered to a mammal in need of said treatment.

29. The method of claim 28, wherein said cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

30. The compound of claim 1, wherein R11 is a group selected from $C_{1-6}$ alkyl, $C_{1-6}$ alkylene-OH; $C_{1-6}$ alkylene-O—$C_{1-6}$alkyl, wherein $C_{1-6}$ alkylene is optionally substituted with a phenyl, and wherein $C_{1-6}$ alkyl is optionally substituted with a fluoro; $C_{1-6}$ alkylene-S—$C_{1-6}$ alkyl; $C_{1-6}$ alkylene-CN; $C_{1-6}$ alkylene-C(=O)—O—$C_{1-6}$ alkyl; $C_{1-6}$ alkylene-O—C(=O)—NH—$C_{1-6}$ alkyl; $C_{3-7}$cycloalkyl; an aryl optionally substituted with a group selected from $C_{1-6}$ alkyl, halogen, CN, OH, and $C_{1-6}$alkylene-OH; an aliphatic heterocycle optionally substituted with a group selected from $C_{1-6}$ alkyl, OH, and $C_{1-6}$ alkylene-OH; and a heteroaryl optionally substituted with a group selected from $C_{1-6}$ alkyl, halogen, CN, OH, and $C_{1-6}$ alkylene-OH.

31. A pharmaceutical composition comprising the compound of claim 1 and optionally a pharmaceutically acceptable carrier or excipient.

32. A method for treatment of a cardiac disease, disorder or condition in a human, wherein a therapeutically effective amount of at least one compound according to claim 1 is administered to a human in need of said treatment.

* * * * *